United States Patent

Swart et al.

(10) Patent No.: US 10,136,644 B2
(45) Date of Patent: Nov. 27, 2018

(54) FUNGICIDAL COMPOSITIONS

(71) Applicant: Syngenta Participations AG, Basel (CH)

(72) Inventors: Gina Mercia Swart, Basel (CH); Ulrich Johannes Haas, Stein (CH); Michael Oostendorp, Stein (CH); Hanno Christian Wolf, Stein (CH)

(73) Assignee: SYNGENTA PARTICIPATIONS AG, Basel (CH)

(*) Notice: Subject to any disclaimer, the term of this patent is extended or adjusted under 35 U.S.C. 154(b) by 0 days.

(21) Appl. No.: 15/432,952

(22) Filed: Feb. 15, 2017

(65) Prior Publication Data

US 2017/0156325 A1    Jun. 8, 2017

Related U.S. Application Data

(63) Continuation of application No. 14/416,775, filed as application No. PCT/EP2013/065480 on Jul. 23, 2013.

(30) Foreign Application Priority Data

Jul. 26, 2012 (EP) .................... 12177995

(51) Int. Cl.

| | | |
|---|---|---|
| *A01N 43/56* | (2006.01) | |
| *A01N 43/36* | (2006.01) | |
| *A01N 43/54* | (2006.01) | |
| *A01N 43/653* | (2006.01) | |
| *A01N 43/40* | (2006.01) | |
| *A01N 37/50* | (2006.01) | |
| *A01N 45/02* | (2006.01) | |
| *A01N 47/24* | (2006.01) | |

(52) U.S. Cl.
CPC ............. *A01N 43/56* (2013.01); *A01N 37/50* (2013.01); *A01N 43/36* (2013.01); *A01N 43/40* (2013.01); *A01N 43/54* (2013.01); *A01N 43/653* (2013.01); *A01N 45/02* (2013.01); *A01N 47/24* (2013.01)

(58) Field of Classification Search
CPC ........ A01N 37/50; A01N 43/36; A01N 43/40; A01N 43/54; A01N 43/653; A01N 45/02; A01N 47/24
See application file for complete search history.

(56) References Cited

U.S. PATENT DOCUMENTS

| | | |
|---|---|---|
| 8,349,877 B2 | 1/2013 | Brix et al. |
| 9,155,303 B2 | 10/2015 | Walter et al. |

FOREIGN PATENT DOCUMENTS

| | | |
|---|---|---|
| WO | 2007/115765 A1 | 10/2007 |
| WO | 2008/110274 A2 | 9/2008 |
| WO | 2001/048120 A | 4/2011 |
| WO | 2011/048120 | 4/2011 |
| WO | 2012/041874 | 4/2012 |

OTHER PUBLICATIONS

International Search Report for International Patent Application No. PCT/EP2013/065480 dated Sep. 18, 2013.
Gisi, U., Phytopathology, vol. 86; 1996; p. 1273-79.
Colby, S.R., Calculating synergistic and antagonistic responses of herbicide combinations, Weeds; 1967; p. 20-22.

*Primary Examiner* — Sarah Pihonak
(74) *Attorney, Agent, or Firm* — Dinsmore & Shohl LLP; Toni-Junell Herbert

(57) ABSTRACT

A composition suitable for control of diseases caused by phytopathogens comprising a mixture of a compound of formula I

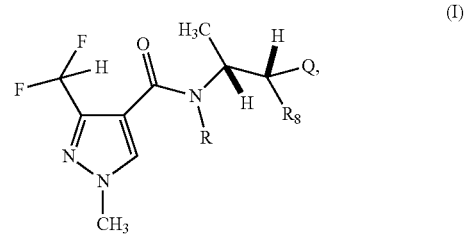

with two compounds selected from compounds known for their fungicidal activity; and a method of controlling diseases on useful plants.

3 Claims, No Drawings

FUNGICIDAL COMPOSITIONS

RELATED APPLICATION INFORMATION

This application is a continuation of U.S. patent application Ser. No. 14/416,775 filed on 23 Jan. 2015 which is a 371 of International Application No. PCT/EP2013/065480, filed 23 Jul. 2013, which claims priority to 12177995.3, filed 26 Jul. 2012, the contents of which are incorporated herein by reference herein.

The present invention relates to novel fungicidal compositions for the treatment of phytopatho-genic diseases of useful plants, especially phytopathogenic fungi, and to a method of controlling phytopathogenic diseases on useful plants.

It is known from WO2008/148570, WO 2010/063700, WO 2010/084078 and WO 2008/151828 that certain pyrazolyl-carboxamide derivatives have biological activity against phytopathogenic fungi. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects. In order to overcome this problem, binary mixtures of pyrazolyl-carboxamides with certain fungicides have been provided in WO 2012/041874.

It has now been found that the addition of a specific further fungicide to compositions comprising the binary mixtures disclosed in WO 2012/041874 leads to novel ternary fungicidal compositions with advantageous properties.

There is therefore proposed in accordance with the invention a novel composition suitable for the control of diseases caused by phytopathogens comprising as component (A) a compound of formula I

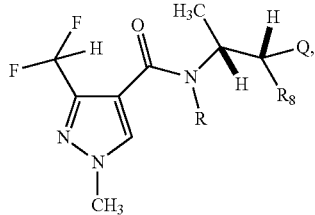
(I)

wherein
R is hydrogen or methoxy;
Q is

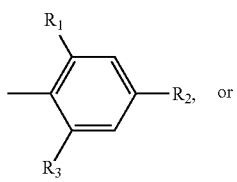
(Q₁)

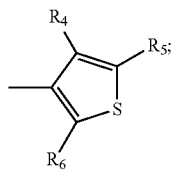
(Q₂)

wherein
$R_1$ is hydrogen, halogen or $C_1$-$C_6$alkyl;
$R_2$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—$C_1$-$C_4$alkyl, $C_1$-$C_6$haloalkyl, $C_1$-$C_6$haloalkoxy, $C_2$-$C_6$haloalkenyl, or $C_2$-$C_6$haloalkenyloxy;
$R_3$ is hydrogen, halogen or $C_1$-$C_6$alkyl; with the proviso that at least one of $R_1$, $R_2$ and $R_3$ is different from hydrogen;
$R_4$, $R_5$ and $R_6$, independently from each other, are hydrogen, halogen or -≡-$R_7$; with the proviso that at least one of $R_4$, $R_5$ and $R_6$ is different from hydrogen;
$R_7$ is hydrogen, $C_1$-$C_6$alkyl, $C_1$-$C_6$haloalkyl or $C_1$-$C_4$alkoxyalkyl; and
$R_8$ is hydrogen or methoxy;
and agrochemically acceptable salts, stereoisomers, diastereoisomers, enantiomers and tautomers of those compounds;
and
as component (B) a compound selected from the group consisting of azoxystrobin (47), dimoxystrobin (226), fluoxastrobin (382), kresoxim-methyl (485), metominostrobin (551), orysastrobin, picoxystrobin (647), pyraclostrobin (690), trifloxystrobin (832), a compound of formula B-1.1

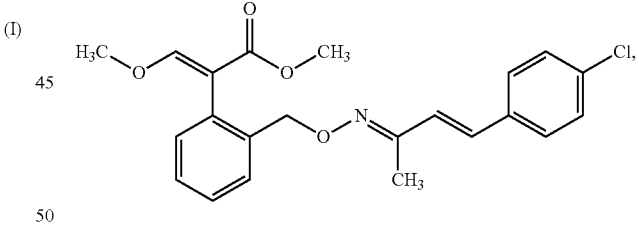
(B-1.1)

azaconazole (40), bromuconazole (96), cyproconazole (207), difenoconazole (247), diniconazole (267), diniconazole-M (267), epoxiconazole (298), fenbuconazole (329), fluquinconazole (385), flusilazole (393), flutriafol (397), hexaconazole (435), imazalil (449), imibenconazole (457), ipconazole (468), metconazole (525), myclobutanil (564), oxpoconazole (607), pefurazoate (618), penconazole (619), prochloraz (659), propiconazole (675), prothioconazole (685), simeconazole (731), tebuconazole (761), tetraconazole (778), triadimefon (814), triadimenol (815), triflumizole (834), triticonazole (842), diclobutrazol (1068), etaconazole (1129), furconazole (1198), furconazole-cis (1199) and quinconazole (1378); aldimorph (CAS Reg. No. 91315-15-0), dodemorph (288), fenpropimorph (344), tridemorph (830), fenpropidin (343), spiroxamine (740), piperalin (648), a compound of formula B-3.1

(B-3.1)

cyprodinil (208), mepanipyrim (508), pyrimethanil (705), anilazine (878), benalaxyl (56), benalaxyl-M, benodanil (896), benomyl (62), benthiavalicarb, benthiavalicarb-isopropyl (68), biphenyl (81), bitertanol (84), blasticidin-S (85), bordeaux mixture (87), boscalid (88), bupirimate (98), cadmium chloride, captafol (113), captan (114), carbendazim (116), carbon disulfide (945), carboxin (120), carpropamid (122), cedar leaf oil, chinomethionat (126), chloroneb (139), chlorothalonil (142), chlozolinate (149), cinnamaldehyde, copper, copper ammoniumcarbonate, copper hydroxide (169), copper octanoate (170), copper oleate, copper sulphate (87), cyazofamid (185), cycloheximide (1022), cymoxanil (200), dichlofluanid (230), dichlone (1052), dichloropropene (233), diclocymet (237), diclomezine (239), dicloran (240), diethofencarb (245), diflumetorim (253), dimethirimol (1082), dimethomorph (263), dinocap (270), dithianon (279), dodine (289), edifenphos (290), ethaboxam (304), ethirimol (1133), etridiazole (321), famoxadone (322), fenamidone (325), fenaminosulf (1144), fenamiphos (326), fenarimol (327), fenfuram (333), fenhexamid (334), fenoxanil (338), fenpiclonil (341), fentin acetate (347), fentin chloride, fentin hydroxide (347), ferbam (350), ferimzone (351), fluazinam (363), fludioxonil (368), flusulfamide (394), flutolanil (396), folpet (400), formaldehyde (404), fosetyl-aluminium (407), fthalide (643), fuberidazole (419), furalaxyl (410), furametpyr (411), flyodin (1205), fuazatine (422), hexachlorobenzene (434), hymexazole, iminoctadine tris(albesliate) (CAS Reg. No: 99257-43-9), iodocarb (3-Iodo-2-propynyl butyl carbamate), iprobenfos (IBP) (469), iprodione (470), iprovalicarb (471), isoprothiolane (474), kasugamycin (483), mancozeb (496), maneb (497), manganous dimethyldithiocarbamate, mefenoxam (Metalaxyl-M) (517), mepronil (510), mercuric chloride (511), mercury, metalaxyl (516), methasulfocarb (528), metiram (546), metrafenone, nabam (566), neem oil (hydrophobic extract), nuarimol (587), octhilinone (590), ofurace (592), oxadixyl (601), oxine copper (605), oxolinic acid (606), oxycarboxin (608), oxytetracycline (611), paclobutrazole (612), paraffin oil (628), paraformaldehyde, pencycuron (620), pentachloronitrobenzene (716), pentachlorophenol (623), penthiopyrad, perfurazoate, phosphoric acid, polyoxin (654), polyoxin D zinc salt (654), potassium bicarbonate, probenazole (658), procymidone (660), propamocarb (668), propineb (676), proquinazid (682), prothiocarb (1361), pyrazophos (693), pyrifenox (703), pyroquilon (710), quinoxyfen (715), quintozene (PCN(B) (716), silthiofam (729), sodium bicarbonate, sodium diacetate, sodium propionate, streptomycin (744), sulphur (754), TCMTB, tecloftalam, tecnazene (TCN(B) (767), thiabendazole (790), thifluzamide (796), thiophanate (1435), thiophanate-methyl (802), thiram (804), tolclofos-methyl (808), tolylfluanid (810), triazoxide (821), trichoderma harzianum (825), triclazole (828), triforine (838), triphenyltin hydroxide (347), validamycin (846), vinclozolin (849), zineb (855), ziram (856), zoxamide (857), 1,1-bis(4-chlorophenyl)-2-ethoxyethanol (IUPAC-Name) (910), 2,4-dichlorophenyl benzenesulfonate (IUPAC-/Chemical Abstracts-Name) (1059), 2-fluoro-N-methyl-N-1-naphthylacetamide (IUPAC-Name) (1295), 4-chlorophenyl phenyl sulfone (IUPAC-Name) (981), a compound of formula B-5.1

(B-5.1)

a compound of formula B-5.2

(B-5.2)

a compound of formula B-5.3

(B-5.3)

a compound of formula B-5.4

(B-5.4)

a compound of formula B-5.5

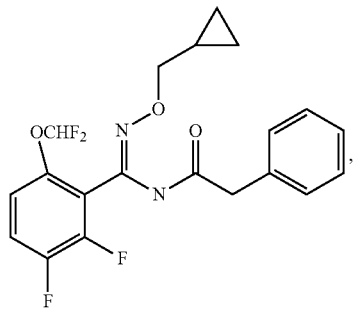

(B-5.5)

a compound of formula B-5.6

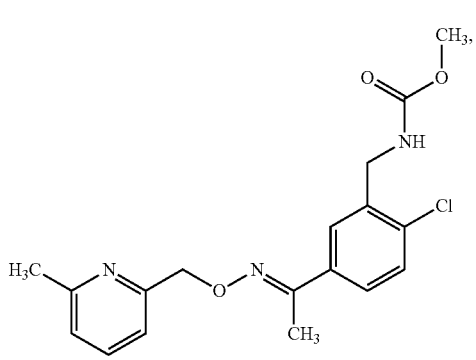

(B-5.6)

a compound of formula B-5.7

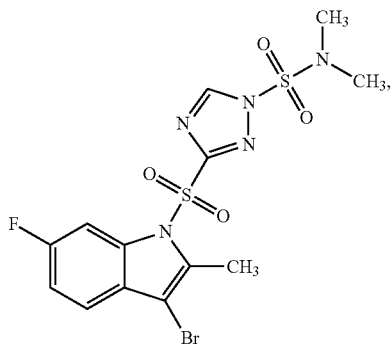

(B-5.7)

3-difluoromethyl-1-methyl-1H-pyrazole-4-carboxylic acid (2-bicyclopropyl-2-yl-phenyl)-amide (compound B-5.8), 3-difluoromethyl-1-methyl-1H-pyrazole-4-carboxylic acid (9-isopropyp-1,2,3,4-tetrahydro-1,4-methano-naphthalen-5-yl)-amide (compound B-5.9), 1,3-dimethyl-5-fluoro-1H-pyrazole-4-carboxylic acid [2-(1,3-dimethylbutyl)phenyl]-amide (compound B-5.10), 3-difluoromethyl-1-methyl-1H-pyrazole-4-carboxylic acid (3',4'-dichloro-5-fluoro-1,1'-biphenyl-2-yl)-amide (compound B-5.11, bixafen), N-{2-[3-chloro-5-(trifluoromethyl)pyridin-2-yl]ethyl}-2-(trifluoromethyl)benzamid (compound B-5.12, fluopyram), 3-difluoromethyl-1-methyl-1H-pyrazole-4-carboxylic acid N-[2-(1,1,2,2-tetrafluoroethoxy) phenyl]-amide (compound B-5.13), 3-difluoromethyl-1-methyl-1H-pyrazole-4-carboxylic acid N-[2-(1,1,2,3,3,3-hexafluoropropoxy)phenyl]-amide (compound B-5.14), 3-difluoromethyl-1-methyl-1H-pyrazole-4-carboxylic acid N-[2-(2-chloro-1,1,2-trifluoroethoxy)phenyl]-amide (compound B-5.15), 3-difluoromethyl-1-methyl-1H-pyrazole-4-carboxylic acid N-(4'-trifluoromethyl-biphen-2-yl)-amide (compound B-5.16), 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18), acibenzolar-S-methyl (6), chlormequat chloride (137), ethephon (307), mepiquat chloride (509) and trinexapac-ethyl (841), abamectin (1), clothianidin (165), emamectin benzoate (291), imidacloprid (458), tefluthrin (769), thiamethoxam (792), glyphosate (419), a compound of formula V

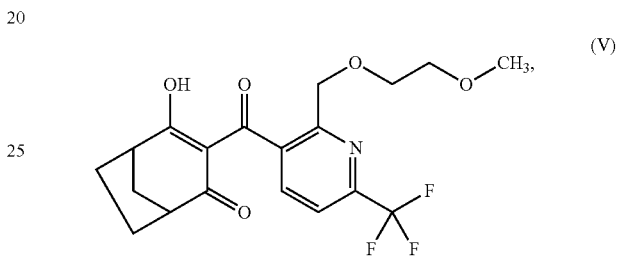

(V)

fomesafen, isopyrazam, sedaxane, the compound of formula (VI)

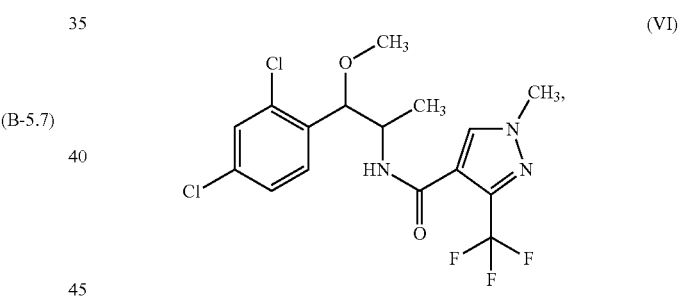

(VI)

the compound of formula (VII)

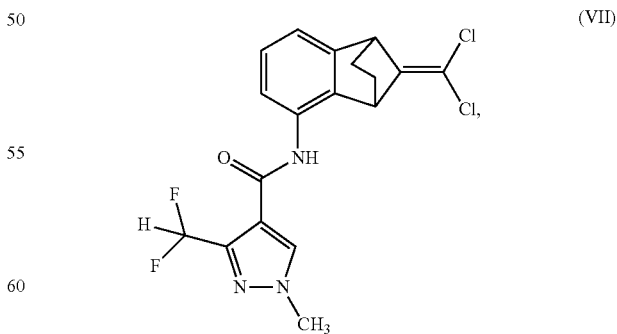

(VII)

1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone, 1-[4-[4-[5-(2,6-difluorophenyl)-4,5-dihydro-1,2-oxazol-3-yl]-1,3-thiazol- 2-yl]piperidin-1-yl]-2-[5-methyl-3-(trifluoromethyl)-1H-pyrazol-1-yl]ethanone, fluxapyroxad, phosphorous acid, phosphorous acid sodium salt and phosphorous acid ammonium salt;

and as component (C) a compound selected from the group consisting of the compound of formula VII, fluxapyroxad, bixafen, penthiopyrad, fluopyram, boscalid, isopyrazam, propiconazole, cyproconazole, difenoconazole, prothioconazole, thiabendazole azoxystrobin, thiophanate methyl, iminoctadine tris(albesilate), tebuconazole, pyraclostrobin, trifloxystrobin, fludioxonil, cyprodinil and fluazinam; with the exception of the mixtures comprising a compound of formula I+azoxystrobin+cyproconazole and with the proviso that in each composition component (B) is different from component (C).

According to the present invention, preferred salts of glyphosate are the potassium, isopropylammonium, sodium, trimesium, ammonium and diammonium salts. Preferred salts of glufosinate are disclosed in U.S. Pat. No. 4,168,963, a preferred salt is the ammonium salt.

The compounds of formula I wherein $R_8$ is hydrogen can occur in the two enantiomeric forms of formula Ia and Ib:

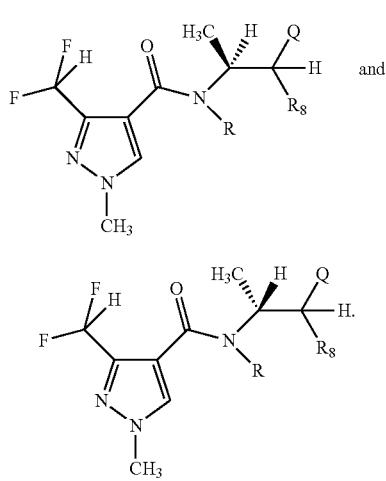

The invention encompasses both enantiomeric forms of the compounds of formula I. The compounds of formula I and their preparation are described in WO 2010/063700, WO 2010/084078 and WO 2008/151828.

It has been found that the use of components (B) and (C) in combination with component (A) surprisingly and substantially may enhance the effectiveness of the latter against fungi, and vice versa. Additionally, the method of the invention is effective against a wider spectrum of such fungi that can be combated with the active ingredients of this method, when used solely.

In general, the weight ratio of component (A) to the mixture of components (B) and (C) is from 1000:1 to 1:1000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In a preferred embodiment of the invention, the ratios by weight of component (A) to the mixture of components (B) and (C) are 4:1 to 1:4.

In a preferred embodiment of the invention, ratios by weight of component (B) to component (C) are from 2:1 to 1:6.

It has been found, surprisingly, that certain weight ratios of component (A) to the mixture of component (B) and (C) are able to give rise to synergistic activity. Therefore, a further aspect of the invention are compositions, wherein component (A) and the mixture of component (B) and (C) are present in the composition in amounts producing a synergistic effect. This synergistic activity is apparent from the fact that the fungicidal activity of the composition comprising component (A) the mixture of component (B) and (C) is greater than the sum of the fungicidal activities of component (A) and of the mixture of component (B) and (C). This synergistic activity extends the range of action of component (A) and the mixture of component (B) and (C) in two ways. Firstly, the rates of application of component (A) and the mixture of component (B) and (C) are lowered whilst the action remains equally good, meaning that the active ingredient mixture still achieves a high degree of phytopathogen control even where the two individual components have become totally ineffective in such a low application rate range. Secondly, there is a substantial broadening of the spectrum of phytopathogens that can be controlled.

A synergistic effect exists whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient (A) using p ppm of active ingredient

Y=% action by active ingredients (B+C) using q ppm of active ingredient.

Or:

X=% action by active ingredient (A+B) using p ppm of active ingredient

Y=% action by active ingredient (C) using q ppm of active ingredient.

Or:

X=% action by active ingredient (A+C) using p ppm of active ingredient

Y=% action by active ingredient (B) using q ppm of active ingredient.

According to COLBY, the expected (additive) action of active ingredients (A)+(B+C) or (A+B)+(C) or (A+C)+(B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

Synergism can also be calculated by using the following formula:

$$E \text{ (expected value)} = X+Y+Z-[(X\ Y)+(X\ Z)+(Y\ Z)/100]+[X\ Y\ Z/10000]$$

X, Y, Z=% action by active ingredient (A), (B) and (C) alone using p ppm of active ingredient.

However, besides the actual synergistic action with respect to fungicidal activity, the compositions according to the invention can also have further surprising advantageous properties. Examples of such advantageous properties that may be mentioned are: more advantageuos degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

Some compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention can be applied to the phytopathogenic microorganisms, the useful plants, the locus thereof, the propagation material thereof, storage goods or technical materials threatened by microorganism attack.

The compositions according to the invention may be applied before or after infection of the useful plants, the propagation material thereof, storage goods or technical materials by the microorganisms.

A further aspect of the present invention is a method of controlling diseases on useful plants or on propagation material thereof caused by phytopathogens, which comprises applying to the useful plants, the locus thereof or propagation material thereof a composition according to the invention. Preferred is a method, which comprises applying to the useful plants or to the locus thereof a composition according to the invention, more preferably to the useful plants. Further preferred is a method, which comprises applying to the propagation material of the useful plants a composition according to the invention.

The components (B) and (C) are known. Where the components (B) and (C) are included in "The Pesticide Manual" [The Pesticide Manual - A World Compendium; Thirteenth Edition; Editor: C. D. S. Tomlin; The British Crop Protection Council], they are described therein under the entry number given in round brackets hereinabove for the particular component (B) and (C); for example, the compound "abamectin" is described under entry number (1). Most of the components (B) and (C) are referred to hereinabove by a so-called "common name", the relevant "ISO common name" or another "common name" being used in individual cases. If the designation is not a "common name", the nature of the designation used instead is given in round brackets for the particular component (B) and (C) respectively; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed.

The following components (B) and (C) are registered under a CAS-Reg. No. aldimorph (CAS 91315-15-0); arsenates (CAS 1327-53-3); benalaxyl -M (CAS 98243-83-5); benthiavalicarb (CAS 413615-35-7); cadmium chloride (CAS 10108-64-2); cedar leaf oil (CAS 8007-20-3); cinnamaldehyde (CAS: 104-55-2); copper ammoniumcarbonate (CAS 33113-08-5); copper oleate (CAS 1120-44-1); iodocarb (3-Iodo-2-propynyl butyl carbamate) (CAS 55406-53-6); hymexazole (CAS 10004-44-1); manganous dimethyldithiocarbamate (CAS 15339-36-3); mercury (CAS 7487-94-7; 21908-53-2; 7546-30-7); metrafenone (CAS 220899-03-6); neem oil (hydrophobic extract) (CAS 8002-65-1); orysastrobin CAS 248593-16-0); paraformaldehyde (CAS 30525-89-4); penthiopyrad (CAS 183675-82-3); phosphoric acid (CAS 7664-38-2); potassium bicarbonate (CAS 298-14-6); sodium bicarbonate (CAS 144-55-8); sodium diacetate (CAS 127-09-3); sodium propionate (CAS 137-40-6); TCMTB (CAS 21564-17-0); and tolyfluanid (CAS 731-27-1).

Compound B-1.1 ("enestrobin") is described in EP-0-936-213; compound B-3.1 ("flumorph") in U.S. Pat. No. 6,020,332, CN-1-167-568, CN-1-155-977 and in EP-0-860-438; compound B-5.1 ("mandipropamid") in WO 01/87822; compound B-5.2 in WO 98/46607; compound B-5.3 ("fluopicolide") in WO 99/42447; compound B-5.4 ("cyflufenamid") in WO 96/19442; compound B-5.5 in WO 99/14187; compound B-5.6 ("pyribencarb") is registered under CAS-Reg. No. 325156-49-8; compound B-5.7 ("amisulbrom" or "ambromdole") is registered under CAS-Reg. No. 348635-87-0; compound B-5.8 (3-difluoromethyl-1-methyl-1H-pyrazole-4-carboxylic acid (2-bicyclopropyl-2-yl-phenyl)-amide) is described in WO 03/74491; compound B-5.9 (3-difluoromethyl-1-methyl-1H-pyrazole-4-carboxylic acid (9-isopropyp-1,2,3,4-tetrahydro-1,4-methano-naphthalen-5-yl)-amide) is described in WO 04/35589 and in WO 06/37632; compound B-5.10 (1,3-dimethyl-5-fluoro-1H-pyrazole-4-carboxylic acid [2-(1,3-dimethylbutyl)phenyl]- amide) is described in WO 03/10149; compound B-5.11 (3-difluoromethyl-1-methyl-1H-pyrazole-4-carboxylic acid (3',4'-dichloro-5-fluoro-1,1'-biphenyl-2-yl)-amide; "bixafen") is registered under CAS-Reg. No.: 581809-46-3 and described in WO 03/70705; compound B-5.12 (N-{2-[3-Chloro-5-(trifluoromethyl)pyridin-2-yl]ethyl}-2-(trifluoromethyl)benzamid; "fluopyram") is registered under CAS-Reg. No: 658066-35-4 and described in WO 04/16088; compounds B-5.13, B-5.14 and B-5.15 are described in WO 2007/17450; compounds B-5.16, B-5.17 and B-5.18 are described in WO 2006/120219. The compound of formula B-7.1 is described in WO 03/015519, the compound of formula B-7.2 is described in WO 2004/067528, the compound of formula B-7.3 is described in WO 2007/115644. The compound of formula V is described in WO 2001/094339. Isopyrazam (3-(difluoromethyl)-1-methyl-N-[1,2,3,4-tetrahydro-9-(1-methylethyl)-1,4-methanonaphthalen-5-yl]-1H-pyrazole-4-carboxamide) is described in WO 2004/035589, in WO 2006/037632 and in EP 1556385 and is registered under the CAS-Reg. 881685-58-1. Sedaxane (N-[2-[1,1'-bicyclopropyl]-2-ylphenyl]-3-(difluoromethyl)-1-methyl-1H-pyrazole-4-carboxamide) is described in WO 2003/074491 and is registered under the CAS-Reg. 874967-67-6; The compound of formula (VI) is described in WO 2008/014870; and the compounds of formula (VII) (solatenol, 3-difluoromethyl-1-methyl-1H-pyrazole-4-carboxylic acid (9-dichloromethylene-1,2,3,4-tetrahydro-1,4-methanonaphthalen-5-yl)-amide) is described in WO 2007/048556. Fomesafen is registered under the CAS-Reg. No. 72178-02-0. 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone and 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone (CAS-Reg. No.: 1003318-67-9) are both disclosed in WO 2010/123791, WO 2008/013925, WO 2008/013622 and WO 2011/051243 page 20), 3-difluoromethyl-1-methyl-1H-pyrazole-4-carboxylic acid (3',4',5'-trifluoro-biphenyl-2-yl)-amide (fluxapyroxad) is disclosed in WO 2006/087343.

Throughout this document the expression "composition" means the various mixtures or combinations of components (A) and the mixture of (B) and (C), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) and (C) is not essential for working the present invention.

As components (A) are compounds of formula I preferred, wherein Q is $Q_1$, wherein $R_1$, $R_2$ and $R_3$ are preferably halogen, in particular chloro; R is methoxy and $R_8$ is hydrogen.

Preferred components (A) are listed in the following Table 1:

TABLE 1

Compounds of formula Ic:

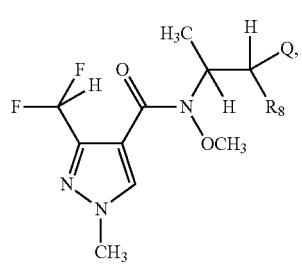

(Ic)

wherein Q is

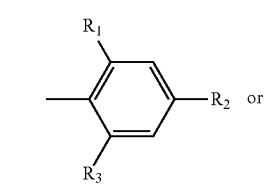

($Q_1$)

or

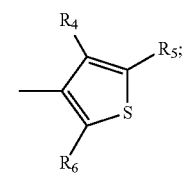

($Q_2$)

| Compound No. | $R_1$ | $R_2$ | $R_3$ | Q | $R_4$ | $R_5$ | $R_6$ | $R_8$ |
|---|---|---|---|---|---|---|---|---|
| 1.001 | Cl | Cl | Cl | $Q_1$ | — | — | — | H |
| 1.002 | Cl | H | Cl | $Q_1$ | — | — | — | H |
| 1.003 | Cl | Cl | H | $Q_1$ | — | — | — | H |
| 1.004 | Cl | Br | Cl | $Q_1$ | — | — | — | H |
| 1.005 | Br | Br | Br | $Q_1$ | — | — | — | H |
| 1.006 | H | Cl | H | $Q_1$ | — | — | — | H |
| 1.007 | H | Br | H | $Q_1$ | — | — | — | H |
| 1.008 | H | $CF_3$ | H | $Q_1$ | — | — | — | H |
| 1.009 | — | — | — | $Q_2$ | Cl | Cl | Cl | H |
| 1.010 | — | — | — | $Q_2$ | Cl | H | Cl | H |
| 1.011 | — | — | — | $Q_2$ | H | Cl | Cl | H |
| 1.012 | — | — | — | $Q_2$ | Cl | Cl | Br | H |
| 1.013 | — | — | — | $Q_2$ | Cl | H | Br | H |
| 1.014 | — | — | — | $Q_2$ | H | Cl | Br | H |
| 1.015 | — | — | — | $Q_2$ | H | Cl | H | H |
| 1.016 | — | — | — | $Q_2$ | Cl | H | H | H |
| 1.017 | Cl | Cl | Cl | $Q_1$ | — | — | — | $OCH_3$ |
| 1.018 | Cl | H | Cl | $Q_1$ | — | — | — | $OCH_3$ |
| 1.019 | Cl | Cl | H | $Q_1$ | — | — | — | $OCH_3$ |
| 1.020 | Cl | Br | Cl | $Q_1$ | — | — | — | $OCH_3$ |
| 1.021 | Br | Br | Br | $Q_1$ | — | — | — | $OCH_3$ |
| 1.022 | H | Cl | H | $Q_1$ | — | — | — | $OCH_3$ |
| 1.023 | H | Br | H | $Q_1$ | — | — | — | $OCH_3$ |
| 1.024 | H | $CF_3$ | H | $Q_1$ | — | — | — | $OCH_3$ |
| 1.025 | — | — | — | $Q_2$ | Cl | Cl | Cl | $OCH_3$ |
| 1.026 | — | — | — | $Q_2$ | Cl | H | Cl | $OCH_3$ |
| 1.027 | — | — | — | $Q_2$ | H | Cl | Cl | $OCH_3$ |
| 1.028 | — | — | — | $Q_2$ | Cl | Cl | Br | $OCH_3$ |
| 1.029 | — | — | — | $Q_2$ | Cl | H | Br | $OCH_3$ |
| 1.030 | — | — | — | $Q_2$ | H | Cl | Br | $OCH_3$ |
| 1.031 | — | — | — | $Q_2$ | H | Cl | H | $OCH_3$ |
| 1.032 | — | — | — | $Q_2$ | Cl | H | H | $OCH_3$ |

Further preferred components (A) are listed in the following Table 2:

TABLE 2

Compounds of formula Id:

(Id)

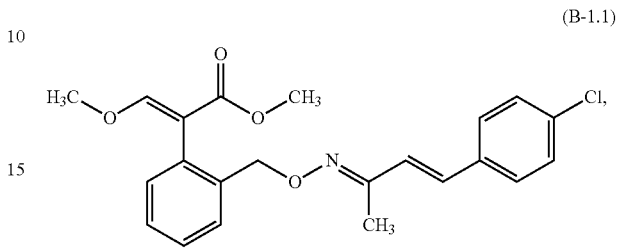

wherein
Q is (Q₁)

(Q₂)

| Compound No. | R₁ | R₂ | R₃ | Q | R₄ | R₅ | R₆ | R₈ |
|---|---|---|---|---|---|---|---|---|
| 2.001 | Cl | Cl | Cl | Q₁ | — | — | — | H |
| 2.002 | Cl | H | Cl | Q₁ | — | — | — | H |
| 2.003 | Cl | Cl | H | Q₁ | — | — | — | H |
| 2.004 | Cl | Br | Cl | Q₁ | — | — | — | H |
| 2.005 | Br | Br | Br | Q₁ | — | — | — | H |
| 2.006 | H | Cl | H | Q₁ | — | — | — | H |
| 2.007 | H | Br | H | Q₁ | — | — | — | H |
| 2.008 | H | CF₃ | H | Q₁ | — | — | — | H |
| 2.009 | — | — | — | Q₂ | Cl | Cl | Cl | H |
| 2.010 | — | — | — | Q₂ | Cl | H | Cl | H |
| 2.011 | — | — | — | Q₂ | H | Cl | Cl | H |
| 2.012 | — | — | — | Q₂ | Cl | Cl | Br | H |
| 2.013 | — | — | — | Q₂ | Cl | H | Br | H |
| 2.014 | — | — | — | Q₂ | H | Cl | Br | H |
| 2.015 | — | — | — | Q₂ | H | Cl | H | H |
| 2.016 | — | — | — | Q₂ | Cl | H | H | H |
| 2.017 | Cl | Cl | Cl | Q₁ | — | — | — | OCH₃ |
| 2.018 | Cl | H | Cl | Q₁ | — | — | — | OCH₃ |
| 2.019 | Cl | Cl | H | Q₁ | — | — | — | OCH₃ |
| 2.020 | Cl | Br | Cl | Q₁ | — | — | — | OCH₃ |
| 2.021 | Br | Br | Br | Q₁ | — | — | — | OCH₃ |
| 2.022 | H | Cl | H | Q₁ | — | — | — | OCH₃ |
| 2.023 | H | Br | H | Q₁ | — | — | — | OCH₃ |
| 2.024 | H | CF₃ | H | Q₁ | — | — | — | OCH₃ |
| 2.025 | — | — | — | Q₂ | Cl | Cl | Cl | OCH₃ |
| 2.026 | — | — | — | Q₂ | Cl | H | Cl | OCH₃ |
| 2.027 | — | — | — | Q₂ | H | Cl | Cl | OCH₃ |
| 2.028 | — | — | — | Q₂ | Cl | Cl | Br | OCH₃ |
| 2.029 | — | — | — | Q₂ | Cl | H | Br | OCH₃ |
| 2.030 | — | — | — | Q₂ | H | Cl | Br | OCH₃ |
| 2.031 | — | — | — | Q₂ | H | Cl | H | OCH₃ |
| 2.032 | — | — | — | Q₂ | Cl | H | H | OCH₃ |

The following binary mixtures of components (A) with components (B) are preferred and are defined as members of the group P (the abbreviation "TX" means: "one compound selected from the group consisting of the compounds specifically described in Tables 1 and 2 of the present invention"):

Group P:
azoxystrobin (47)+TX, dimoxystrobin (226)+TX, fluoxastrobin (382)+TX, kresoxim-methyl (485)+TX, metominostrobin (551)+TX, orysastrobin+TX, picoxystrobin (647)+TX, pyraclostrobin (690), trifloxystrobin (832)+TX, a compound of formula B-1.1+TX (B-1.1)

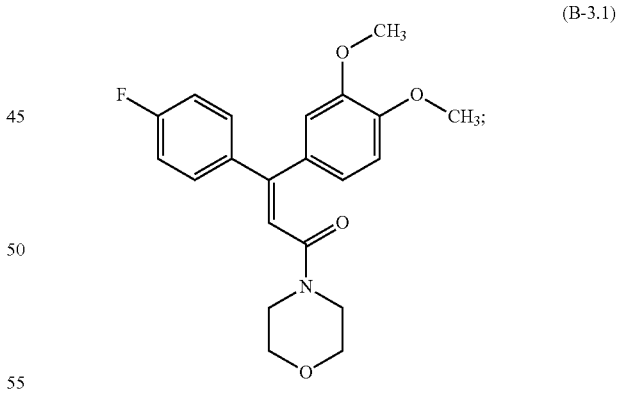

azaconazole (40)+TX, bromuconazole (96)+TX, cyproconazole (207)+TX, difenoconazole (247)+TX, diniconazole (267)+TX, diniconazole-M (267)+TX, epoxiconazole (298)+TX, fenbuconazole (329)+TX, fluquinconazole (385)+TX, flusilazole (393)+TX, flutriafol (397)+TX, hexaconazole (435)+TX, imazalil (449)+TX, imibenconazole (457)+TX, ipconazole (468)+TX, metconazole (525)+TX, myclobutanil (564)+TX, oxpoconazole (607)+TX, pefurazoate (618)+TX, penconazole (619)+TX, prochloraz (659)+TX, propiconazole (675)+TX, prothioconazole (685)+TX, simeconazole (731)+TX, tebuconazole (761)+TX, tetraconazole (778)+TX, triadimefon (814)+TX, triadimenol (815)+TX, triflumizole (834)+TX, triticonazole (842)+TX, diclobutrazol (1068)+TX, etaconazole (1129)+TX, furconazole (1198)+TX, furconazole-cis (1199)+TX, quinconazole (1378)+TX, aldimorph+TX, dodemorph (288)+TX, fenpropimorph (344)+TX, tridemorph (830)+TX, fenpropidin (343)+TX, spiroxamine (740)+TX, piperalin (648)+TX, a compound of formula B-3.1+

(B-3.1)

+TX, cyprodinil (208)+TX, mepanipyrim (508)+TX, pyrimethanil (705)+TX; anilazine (878)+TX, arsenates+TX, benalaxyl (56)+TX, benalaxyl-M+TX, benodanil (896)+TX, benomyl (62)+TX, benthiavalicarb+TX, benthiavalicarb-isopropyl (68)+TX, biphenyl (81)+TX, bitertanol (84)+TX, blasticidin-S (85)+TX, bordeaux mixture (87)+TX, boscalid (88)+TX, bupirimate (98)+TX, cadmium chloride+TX, captafol (113)+TX, captan (114)+TX, carbendazim (116)+TX, carbon disulfide (945)+TX, carboxin (120)+TX, carpropamid (122)+TX, cedar leaf oil+TX, chinomethionat (126)+TX, chloroneb (139)+TX, chlorothalonil (142)+TX, chlozolinate (149)+TX, cinnamaldehyde+TX, copper+TX, copper ammoniumcarbonate+TX, copper hydroxide (169)+TX, copper octanoate (170)+TX, copper oleate+TX, copper sulphate (87)+TX, cyazofamid (185)+TX, cycloheximide (1022)+TX, cymoxanil (200)+TX, dichlofluanid (230)+TX, dichlone (1052)+TX, dichloropropene (233)+TX, diclocymet (237)+TX, diclomezine (239)+TX, dicloran (240)+TX, diethofencarb (245)+TX, diflumetorim (253)+TX, dimethirimol (1082)+TX, dimethomorph (263)+TX, dinocap (270)+TX, dithianon (279)+TX, dodine (289)+TX, edifenphos (290)+TX, ethaboxam (304)+TX, ethirimol (1133)+TX, etridiazole (321)+TX, famoxadone (322)+TX, fenamidone (325)+TX, fenaminosulf (1144)+TX, fenamiphos (326)+TX, fenarimol (327)+TX, fenfuram (333)+TX, fenhexamid (334)+TX, fenoxanil (338)+TX, fenpiclonil (341)+TX, fentin acetate (347)+TX, fentin chloride+TX, fentin hydroxide (347)+TX, ferbam (350)+TX, ferimzone (351)+TX, fluazinam (363)+TX, fludioxonil (368)+TX, flusulfamide (394)+TX, flutolanil (396)+TX, folpet (400)+TX, formaldehyde (404)+TX, fosetyl-aluminium (407)+TX, fthalide (643)+TX, fuberidazole (419)+TX, furalaxyl (410)+TX, furametpyr (411)+TX, flyodin (1205)+TX, fuazatine (422)+TX, hexachlorobenzene (434)+TX, hymexazole+TX, iminoctadine tris(albesliate) [99257-43-9]+TX, iodocarb (3-Iodo-2-propynyl butyl carbamate)+TX, iprobenfos (IBP) (469)+TX, iprodione (470)+TX, iprovalicarb (471)+TX, isoprothiolane (474)+TX, kasugamycin (483)+TX, mancozeb (496)+TX, maneb (497)+TX, manganous dimethyldithiocarbamate+TX, mefenoxam (Metalaxyl-M) (517)+TX, mepronil (510)+TX, mercuric chloride (511)+TX, mercury+TX, metalaxyl (516)+TX, methasulfocarb (528)+TX, metiram (546)+TX, metrafenone+TX, nabam (566)+TX, neem oil (hydrophobic extract)+TX, nuarimol (587)+TX, octhilinone (590)+TX, ofurace (592)+TX, oxadixyl (601)+TX, oxine copper (605)+TX, oxolinic acid (606)+TX, oxycarboxin (608)+TX, oxytetracycline (611)+TX, paclobutrazole (612)+TX, paraffin oil (628)+TX, paraformaldehyde+TX, pencycuron (620)+TX, pentachloronitrobenzene (716)+TX, pentachlorophenol (623)+TX, penthiopyrad+TX, perfurazoate+TX, phosphoric acid+TX, polyoxin (654)+TX, polyoxin D zinc salt (654)+TX, potassium bicarbonate+TX, probenazole (658)+TX, procymidone (660)+TX, propamocarb (668)+TX, propineb (676)+TX, proquinazid (682)+TX, prothiocarb (1361)+TX, pyrazophos (693)+TX, pyrifenox (703)+TX, pyroquilon (710)+TX, quinoxyfen (715)+TX, quintozene (PCN(B) (716)+TX, silthiofam (729)+TX, sodium bicarbonate+TX, sodium diacetate+TX, sodium propionate+TX, streptomycin (744)+TX, sulphur (754)+TX, TCMTB+TX, tecloftalam+TX, tecnazene (TCN(B) (767)+TX, thiabendazole (790)+TX, thifluzamide (796)+TX, thiophanate (1435)+TX, thiophanate-methyl (802)+TX, thiram (804)+TX, tolclofos-methyl (808)+TX, tolylfluanid (810)+TX, triazoxide (821)+TX, trichoderma harzianum (825)+TX, tricyclazole (828)+TX, triforine (838)+TX, triphenyltin hydroxide (347)+TX, validamycin (846)+TX, vinclozolin (849)+TX, zineb (855)+TX, ziram (856)+TX, zoxamide (857)+TX, 1+TX,1-bis(4-chlorophenyl)-2-ethoxyethanol (IUPAC-Name) (910)+TX, 2,4-dichlorophenyl benzenesulfonate (IUPAC-/Chemical Abstracts-Name) (1059)+TX, 2-fluoro-N-methyl-N-1-naphthylacetamide (IUPAC-Name) (1295)+TX, 4-chlorophenyl phenyl sulfone (IUPAC-Name) (981)+TX, a compound of formula B-5.1+TX, a compound of formula B-5.2+TX, a compound of formula B-5.3+TX, a compound of formula B-5.4+TX, a compound of formula B-5.5+TX, a compound of formula B-5.6+TX, a compound of formula B-5.7+TX, compound B-5 5.8+TX, compound B-5.9+TX, compound B-5.10+TX, bixafen+TX, fluopyram+TX, compound B-5.13+TX, compound B-5.14+TX, compound B-5.15+TX, compound B-5.16+TX, compound B-5.17+TX and compound B-5.18+TX, acibenzolar-S-methyl (6)+TX, chlormequat chloride (137)+TX, ethephon (307)+TX, mepiquat chloride (509)+TX, trinexapac-ethyl (841)+TX, abamectin (1)+TX, clothianidin (165)+TX, emamectin benzoate (291)+TX, imidacloprid (458)+TX, tefluthrin (769)+TX, thiamethoxam (792)+TX, and glyphosate (419)+TX, a compound of formula V

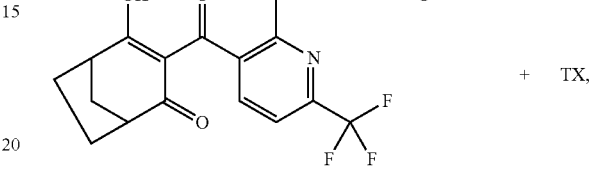

fomesafen+TX, isopyrazam+TX, sedaxane+TX, the compound of formula (VI)+TX

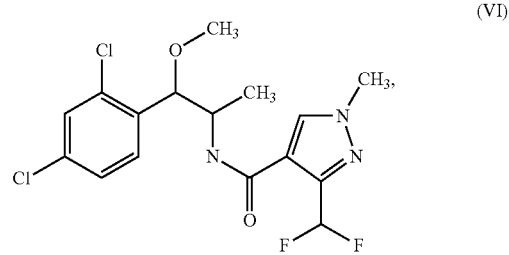 [SMILES: COC(c1ccc(Cl)cc1Cl)C(C)NC(=O)c1cn(C)nc1C(F)F]

the compound of formula (VII)+TX

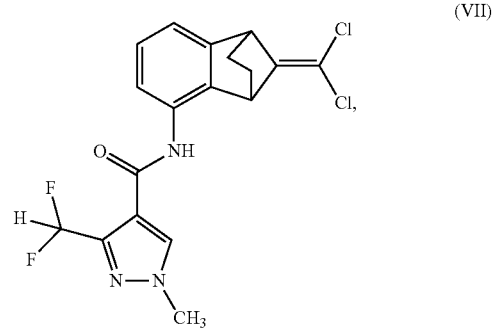 [SMILES: Cn1cc(C(=O)Nc2cccc3c2C2CCC3C2=C(Cl)Cl)c(C(F)F)n1]

1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, fluxapyroxad+TX, phosphorous acid+TX, phosphorous acid sodium salt+TX and phosphorous acid ammonium salt+TX.

Especially preferred compositions according to the present invention are defined in the following Table 3 as embodiments E1 to E21. The term TX1 means "one mixture selected from the group P". The compositions wherein component (B) from the group P is identical to component (C) are excluded. The compositions comprising a compound of formula I according to tables 1 and 2+azoxystrobin+cyproconazole are excluded.

TABLE 3 preferred mixtures according to this invention:

| Embodiment | Component C | | |
|---|---|---|---|
| E1 | compound of formula VII | + | TX1 |
| E2 | fluxapyroxad | + | TX1 |
| E3 | bixafen | + | TX1 |
| E4 | penthiopyrad | + | TX1 |
| E5 | fluopyram | + | TX1 |
| E6 | boscalid | + | TX1 |
| E7 | isopyrazam | + | TX1 |
| E8 | propiconazole | + | TX1 |
| E9 | cyproconazole | + | TX1 |
| E10 | difenoconazole | + | TX1 |
| E11 | prothioconazole | + | TX1 |
| E12 | iminoctadine tris(albesilate) | + | TX1 |
| E13 | thiabendazole | + | TX1 |
| E14 | azoxystrobin | + | TX1 |
| E15 | thiophanate methyl | + | TX1 |
| E16 | tebuconazole | + | TX1 |
| E17 | trifloxystrobin | + | TX1 |
| E18 | pyraclostrobin | + | TX1 |
| E19 | fludioxonil | + | TX1 |
| E20 | cyprodinil | + | TX1 |
| E21 | fluazinam | + | TX1 |

For example, embodiment E1 consists of the following ternary mixtures: azoxystrobin (47)+TX+the compound of formula VII, dimoxystrobin (226)+TX+the compound of formula VII, fluoxastrobin (382)+TX+the compound of formula VII, kresoxim-methyl (485)+TX+the compound of formula VII, metominostrobin (551)+TX+the compound of formula VII, orysastrobin+TX+the compound of formula VII, picoxystrobin (647)+TX+the compound of formula VII, pyraclostrobin (690)+TX+the compound of formula VII, trifloxystrobin (832)+TX+the compound of formula VII, a compound of formula B-1.1

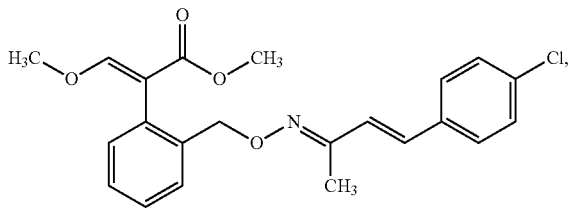

(B-1.1)

+TX+the compound of formula VII, azaconazole (40)+TX+the compound of formula VII, bromuconazole (96)+TX+the compound of formula VII, cyproconazole (207)+TX+the compound of formula VII, difenoconazole (247)+TX+the compound of formula VII, diniconazole (267)+TX+the compound of formula VII, diniconazole-M (267)+TX+the compound of formula VII, epoxiconazole (298)+TX+the compound of formula VII, fenbuconazole (329)+TX+the compound of formula VII, fluquinconazole (385)+TX+the compound of formula VII, flusilazole (393)+TX+the compound of formula VII, flutriafol (397)+TX+the compound of formula VII, hexaconazole (435)+TX+the compound of formula VII, imazalil (449)+TX+the compound of formula VII, imibenconazole (457)+TX+the compound of formula VII, ipconazole (468)+TX+the compound of formula VII, metconazole (525)+TX+the compound of formula VII, myclobutanil (564)+TX+the compound of formula VII, oxpoconazole (607)+TX+the compound of formula VII, pefurazoate (618)+TX+the compound of formula VII, penconazole (619)+TX+the compound of formula VII, prochloraz (659)+TX+the compound of formula VII, propiconazole (675)+TX+the compound of formula VII, prothioconazole (685)+TX+the compound of formula VII, simeconazole (731)+TX+the compound of formula VII, tebuconazole (761)+TX+the compound of formula VII, tetraconazole (778)+TX+the compound of formula VII, triadimefon (814)+TX+the compound of formula VII, triadimenol (815)+TX+the compound of formula VII, triflumizole (834)+TX+the compound of formula VII, triticonazole (842)+TX+the compound of formula VII, diclobutrazol (1068)+TX+the compound of formula VII, etaconazole (1129)+TX+the compound of formula VII, furconazole (1198)+TX+the compound of formula VII, furconazole-cis (1199)+TX+the compound of formula VII, quinconazole (1378)+TX+the compound of formula VII, aldimorph+TX+the compound of formula VII, dodemorph (288)+TX+the compound of formula VII, fenpropimorph (344)+TX+the compound of formula VII, tridemorph (830)+TX+the compound of formula VII, fenpropidin (343)+TX+the compound of formula VII, spiroxamine (740)+TX+the compound of formula VII, piperalin (648)+TX+the compound of formula VII, a compound of formula B-3.1

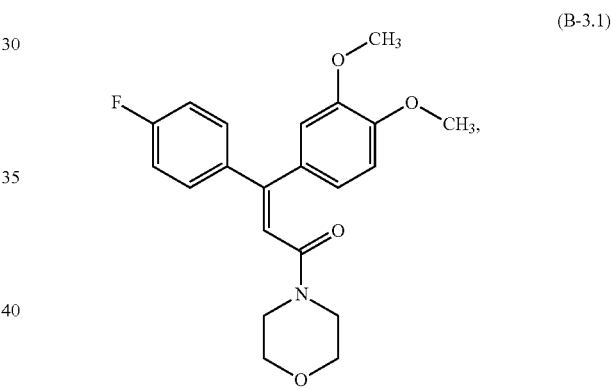

(B-3.1)

+TX+the compound of formula VII, cyprodinil (208)+TX+the compound of formula VII, mepanipyrim (508)+TX+the compound of formula VII, pyrimethanil (705)+TX+the compound of formula VII, anilazine (878)+TX+the compound of formula VII, arsenates+TX+the compound of formula VII, benalaxyl (56)+TX+the compound of formula VII, benalaxyl-M+TX+the compound of formula VII, benodanil (896)+TX+the compound of formula VII, benomyl (62)+TX+the compound of formula VII, benthiavalicarb+TX+the compound of formula VII, benthiavalicarb-isopropyl (68)+TX+the compound of formula VII, biphenyl (81)+TX+the compound of formula VII, bitertanol (84)+TX+the compound of formula VII, blasticidin-S (85)+TX+the compound of formula VII, bordeaux mixture (87)+TX+the compound of formula VII, boscalid (88)+TX+the compound of formula VII, bupirimate (98)+TX+the compound of formula VII, cadmium chloride+TX+the compound of formula VII, captafol (113)+TX+the compound of formula VII, captan (114)+TX+the compound of formula VII, carbendazim (116)+TX+the compound of formula VII, carbon disulfide (945)+TX+the compound of formula VII, carboxin (120)+TX+the compound of formula VII, carpropamid (122)+TX+the compound of formula VII, cedar leaf oil+TX+the compound of formula VII, chinomethionat (126)+TX+the compound of formula VII, chloroneb (139)+TX+the compound of formula VII, chlorothalonil (142)+TX+the compound of formula VII, chlozolinate (149)+TX+the compound of formula VII, cinnamaldehyde+TX+the compound of formula VII, copper+TX+the compound of formula VII, copper ammoniumcarbonate+TX+the compound of formula VII, copper hydroxide (169)+TX+the compound of formula VII, copper octanoate (170)+TX+the compound of formula VII, copper oleate+TX+the compound of formula VII, copper sulphate (87)+TX+the compound of formula VII, cyazofamid (185)+TX+the compound of formula VII, cycloheximide (1022)+TX+the compound of formula VII, cymoxanil (200)+TX+the compound of formula VII, dichlofluanid (230)+TX+the compound of formula VII, dichlone (1052)+TX+the compound of formula VII, dichloropropene (233)+TX+the compound of formula VII, diclocymet (237)+TX+the compound of formula VII, diclomezine (239)+TX+the compound of formula VII, dicloran (240)+TX+the compound of formula VII, diethofencarb (245)+TX+the compound of formula VII, diflumetorim (253)+TX+the compound of formula VII, dimethirimol (1082)+TX+the compound of formula VII, dimethomorph (263)+TX+the compound of formula VII, dinocap (270)+TX+the compound of formula VII, dithianon (279)+TX+the compound of formula VII, dodine (289)+TX+the compound of formula VII, edifenphos (290)+TX+the compound of formula VII, ethaboxam (304)+TX+the compound of formula VII, ethirimol (1133)+TX+the compound of formula VII, etridiazole (321)+TX+the compound of formula VII, famoxadone (322)+TX+the compound of formula VII, fenamidone (325)+TX+the compound of formula VII, fenaminosulf (1144)+TX+the compound of formula VII, fenamiphos (326)+TX+the compound of formula VII, fenarimol (327)+TX+the compound of formula VII, fenfuram (333)+TX+the compound of formula VII, fenhexamid (334)+TX+the compound of formula VII, fenoxanil (338)+TX+the compound of formula VII, fenpiclonil (341)+TX+the compound of formula VII, fentin acetate (347)+TX+the compound of formula VII, fentin chloride+TX+the compound of formula VII, fentin hydroxide (347)+TX+the compound of formula VII, ferbam (350)+TX+the compound of formula VII, ferimzone (351)+TX+the compound of formula VII, fluazinam (363)+TX+the compound of formula VII, fludioxonil (368)+TX+the compound of formula VII, flusulfamide (394)+TX+the compound of formula VII, flutolanil (396)+TX+the compound of formula VII, folpet (400)+TX+the compound of formula VII, formaldehyde (404)+TX+the compound of formula VII, fosetyl-aluminium (407)+TX+the compound of formula VII, fthalide (643)+TX+the compound of formula VII, fuberidazole (419)+TX+the compound of formula VII, furalaxyl (410)+TX+the compound of formula VII, furametpyr (411)+TX+the compound of formula VII, flyodin (1205)+TX+the compound of formula VII, fuazatine (422)+TX+the compound of formula VII, hexachlorobenzene (434)+TX+the compound of formula VII, hymexazole+TX+the compound of formula VII, iminoctadine tris (albesliate) (CAS Reg. No. 99257-43-9)+TX+the compound of formula VII, iodocarb (3-Iodo-2-propynyl butyl carbamate)+TX+the compound of formula VII, iprobenfos (IBP) (469)+TX+the compound of formula VII, iprodione (470)+TX+the compound of formula VII, iprovalicarb (471)+TX+the compound of formula VII, isoprothiolane (474)+TX+the compound of formula VII, kasugamycin (483)+TX+the compound of formula VII, mancozeb (496)+TX+the compound of formula VII, maneb (497)+TX+the compound of formula VII, manganous dimethyldithiocarbamate+TX+the compound of formula VII, mefenoxam (Metalaxyl-M) (517)+TX+the compound of formula VII, mepronil (510)+TX+the compound of formula VII, mercuric chloride (511)+TX+the compound of formula VII, mercury+TX+the compound of formula VII, metalaxyl (516)+TX+the compound of formula VII, methasulfocarb (528)+TX+the compound of formula VII, metiram (546)+TX+the compound of formula VII, metrafenone+TX+the compound of formula VII, nabam (566)+TX+the compound of formula VII, neem oil (hydrophobic extract)+TX+the compound of formula VII, nuarimol (587)+TX+the compound of formula VII, octhilinone (590)+TX+the compound of formula VII, ofurace (592)+TX+the compound of formula VII, oxadixyl (601)+TX+the compound of formula VII, oxine copper (605)+TX+the compound of formula VII, oxolinic acid (606)+TX+the compound of formula VII, oxycarboxin (608)+TX+the compound of formula VII, oxytetracycline (611)+TX+the compound of formula VII, paclobutrazole (612)+TX+the compound of formula VII, paraffin oil (628)+TX+the compound of formula VII, paraformaldehyde+TX+the compound of formula VII, pencycuron (620)+TX+the compound of formula VII, pentachloronitrobenzene (716)+TX+the compound of formula VII, pentachlorophenol (623)+TX+the compound of formula VII, penthiopyrad+TX+the compound of formula VII, perfurazoate+TX+the compound of formula VII, phosphoric acid+TX+the compound of formula VII, polyoxin (654)+TX+the compound of formula VII, polyoxin D zinc salt (654)+TX+the compound of formula VII, potassium bicarbonate+TX+the compound of formula VII, probenazole (658)+TX+the compound of formula VII, procymidone (660)+TX+the compound of formula VII, propamocarb (668)+TX+the compound of formula VII, propineb (676)+TX+the compound of formula VII, proquinazid (682)+TX+the compound of formula VII, prothiocarb (1361)+TX+the compound of formula VII, pyrazophos (693)+TX+the compound of formula VII, pyrifenox (703)+TX+the compound of formula VII, pyroquilon (710)+TX+the compound of formula VII, quinoxyfen (715)+TX+the compound of formula VII, quintozene (PCN(B) (716)+TX+the compound of formula VII, silthiofam (729)+TX+the compound of formula VII, sodium bicarbonate+TX+the compound of formula VII, sodium diacetate+TX+the compound of formula VII, sodium propionate+TX+the compound of formula VII, streptomycin (744)+TX+the compound of formula VII, sulphur (754)+TX+the compound of formula VII, TCMTB+TX+the compound of formula VII, tecloftalam+TX+the compound of formula VII, tecnazene (TCN(B) (767)+TX+the compound of formula VII, thiabendazole (790)+TX+the compound of formula VII, thifluzamide (796)+TX+the compound of formula VII, thiophanate (1435)+TX+the compound of formula VII, thiophanate-methyl (802)+TX+the compound of formula VII, thiram (804)+TX+the compound of formula VII, tolclofos-methyl (808)+TX+the compound of formula VII, tolylfluanid (810)+TX+the compound of formula VII, triazoxide (821)+TX+the compound of formula VII, trichoderma harzianum (825)+TX+the compound of formula VII, tricyclazole (828)+TX+the compound of formula VII, triforine (838)+TX+the compound of formula VII, triphenyltin hydroxide (347)+TX+the compound of formula VII, validamycin (846)+TX+the compound of formula VII, vinclozolin (849)+TX+the compound of formula VII, zineb (855)+TX+the compound of formula VII, ziram (856)+TX+the compound of formula VII, zoxamide (857)+TX+the compound of formula VII, 1+TX+the compound of formula VII, 1-bis (4-chlorophenyl)-2-ethoxyethanol (IUPAC-Name) (910)+TX+the compound of formula VII, 2+TX+the compound of formula VII, 2,4-dichlorophenyl benzenesulfonate (IUPAC-/Chemical Abstracts-Name) (1059)+TX+the compound of formula VII, 2-fluoro-N-methyl-N-1-naphthylacetamide (IUPAC-Name) (1295)+TX+the compound of formula VII, 4-chlorophenyl phenyl sulfone (IUPAC-Name) (981)+TX+the compound of formula VII, a compound of formula B-5.1+TX+the compound of formula VII, a compound of formula B-5.2+TX+the compound of formula VII, a compound of formula B-5.3+TX+the compound of formula VII, a compound of formula B-5.4+TX+the compound of formula VII, a compound of formula B-5.5+TX+the compound of formula VII, a compound of formula B-5.6+TX+the compound of formula VII, a compound of formula B-5.7+TX+the compound of formula VII, the compound B-5.8+TX+the compound of formula VII, the compound B-5.9+TX+the compound of formula VII, compound B-5.10+TX+the compound of formula VII, bixafen+TX+the compound of formula VII, fluopyram+TX+the compound of formula VII, the compound B-5.13+TX+the compound of formula VII, the compound B-5.14+TX+the compound of formula VII, the compound B-5.15+TX+the compound of formula VII, the compound B-5.16+TX+the compound of formula VII, the compound B-5.17+TX+the compound of formula VII, the compound B-5.18+TX+the compound of formula VII, acibenzolar-S-methyl (6)+TX+the compound of formula VII, chlormequat chloride (137)+TX+the compound of formula VII, ethephon (307)+TX+the compound of formula VII, mepiquat chloride (509)+TX+the compound of formula VII, trinexapac-ethyl (841)+TX+the compound of formula VII, abamectin (1)+TX+the compound of formula VII, clothianidin (165)+TX+the compound of formula VII, emamectin benzoate (291)+TX+the compound of formula VII, imidacloprid (458)+TX+the compound of formula VII, tefluthrin (769)+TX+the compound of formula VII, thiamethoxam (792)+TX+the compound of formula VII, glyphosate (419)+TX+the compound of formula VII, a compound of formula V

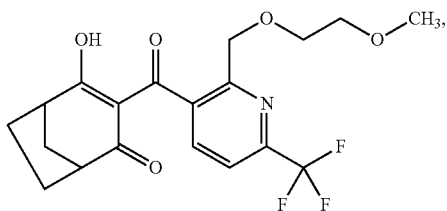 [SMILES: COCCOCc1nc(C(F)(F)F)ccc1C(=O)C1=C(O)C2CCC(C2)C1=O]

(V)+TX+the compound of formula VII, fomesafen+TX+the compound of formula VII, isopyrazam+TX+the compound of formula VII, sedaxane+TX+the compound of formula VII,
the compound of formula (VI)

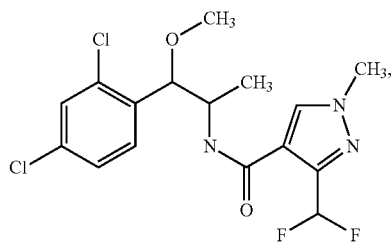

+TX+the compound of formula VII, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX+the compound of formula VII, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX+the compound of formula VII, fluxapyroxad+TX+the compound of formula VII, phosphorous acid +TX+the compound of formula VII, phosphorous acid sodium salt+TX+the compound of formula VII and phosphorous acid ammonium salt+TX+the compound of formula VII.

The active ingredient combinations (A)+(B)+(C) can additionally contain phosphorous acid (IUPAC name phosphonic acid) and salts of phosphorous acid, particularly the sodium, potassium and ammonium salt. Phosphorous acid and salts of phosphorous acid, particularly the sodium, potassium and ammonium salt can also be mixed with components (A)+(B) and (A)+(C). The mixture of components (A)+(B)+(C) with phosphorous acid and salts of phosphorous acid, particularly the sodium, potassium and ammonium salt represents a further embodiment of the invention.

A preferred component (A) is the compound No. 1.001 (3-(difluoromethyl)-N-methoxy-1-methyl-N-[1-methyl-2-(2,4,6-trichlorophenyl)ethyl]pyrazole-4-carboxamide). Preferred pre-mixtures which comprise component (A) and component (B) ready to mix with component (C) are selected from the group consisting of
the compound No. 1.001+the compound of formula VII
the compound No. 1.001+isopyrazam
the compound No. 1.001+difenoconazole
the compound No. 1.001+azoxystrobin
the compound No. 1.001+prothioconazole
the compound No. 1.001+tebuconazole
the compound No. 1.001+pyraclostrobin
the compound No. 1.001+trifloxystrobin
the compound No. 1.001+fludioxonil and
the compound No. 1.001+cyprodinil.

Preferred components (C) for the mixture with pre-mixtures of components (A) and (B) mentioned above are selected from the group consisting of the compound of formula VII, fluxapyroxad, bixafen, penthiopyrad, fluopyram, boscalid, isopyrazam, propiconazole, cyproconazole, difenoconazole, prothioconazole, thiabendazole azoxystrobin, thiophanate methyl and iminoctadine tris(albesilate), with the proviso that in each composition component (B) is different from component (C).

Especially preferred components (C) for the mixture with pre-mixtures of components (A) and (B) mentioned above are selected from the group consisting of isopyrazam, difenoconazole, azoxystrobin, prothioconazole, tebuconazole, pyraclostrobin, trifloxystrobin, fludioxonil, cyprodinil and fluazinam, with the proviso that in each composition component (B) is different from component (C).

Especially preferred embodiments of the present invention are are selected from the following mixtures of active ingredients:
the compound No. 1.001+the compound of formula VII+ isopyrazam;
the compound No. 1.001+the compound of formula VII+ difenoconazole;
the compound No. 1.001+the compound of formula VII+ azoxystrobin;
the compound No. 1.001+the compound of formula VII+ prothioconazole;

the compound No. 1.001+the compound of formula VII+ tebuconazole;
the compound No. 1.001+the compound of formula VII+ pyraclostrobin;
the compound No. 1.001+the compound of formula VII+ trifloxystrobin;
the compound No. 1.001+the compound of formula VII+ fludioxonil;
the compound No. 1.001+the compound of formula VII+ cyprodinil;
the compound No. 1.001+the compound of formula VII+ fluazinam;
the compound No. 1.001+isopyrazam+difenoconazole;
the compound No. 1.001+isopyrazam+azoxystrobin;
the compound No. 1.001+isopyrazam+prothioconazole;
the compound No. 1.001+isopyrazam+tebuconazole;
the compound No. 1.001+isopyrazam+pyraclostrobin;
the compound No. 1.001+isopyrazam+trifloxystrobin;
the compound No. 1.001+isopyrazam+fludioxonil;
the compound No. 1.001+isopyrazam+cyprodinil;
the compound No. 1.001+isopyrazam+fluazinam;
the compound No. 1.001+difenoconazole+azoxystrobin;
the compound No. 1.001+difenoconazole+prothioconazole;
the compound No. 1.001+difenoconazole+tebuconazole;
the compound No. 1.001+difenoconazole+pyraclostrobin;
the compound No. 1.001+difenoconazole+trifloxystrobin;
the compound No. 1.001+difenoconazole+fludioxonil;
the compound No. 1.001+difenoconazole+cyprodinil;
the compound No. 1.001+difenoconazole+fluazinam;
the compound No. 1.001+azoxystrobin+prothioconazole;
the compound No. 1.001+azoxystrobin+tebuconazole;
the compound No. 1.001+azoxystrobin+pyraclostrobin;
the compound No. 1.001+azoxystrobin+trifloxystrobin;
the compound No. 1.001+azoxystrobin+fludioxonil;
the compound No. 1.001+azoxystrobin+cyprodinil;
the compound No. 1.001+azoxystrobin+fluazinam;
the compound No. 1.001+prothioconazole+tebuconazole;
the compound No. 1.001+prothioconazole+pyraclostrobin;
the compound No. 1.001+prothioconazole+trifloxystrobin;
the compound No. 1.001+prothioconazole+fludioxonil;
the compound No. 1.001+prothioconazole+cyprodinil;
the compound No. 1.001+prothioconazole+fluazinam;
the compound No. 1.001+tebuconazole+pyraclostrobin;
the compound No. 1.001+tebuconazole+trifloxystrobin;
the compound No. 1.001+tebuconazole+fludioxonil;
the compound No. 1.001+tebuconazole+cyprodinil;
the compound No. 1.001+tebuconazole+fluazinam;
the compound No. 1.001+pyraclostrobin+trifloxystrobin;
the compound No. 1.001+pyraclostrobin+fludioxonil;
the compound No. 1.001+pyraclostrobin+cyprodinil;
the compound No. 1.001+pyraclostrobin+fluazinam;
the compound No. 1.001+trifloxystrobin+fludioxonil;
the compound No. 1.001+trifloxystrobin+cyprodinil;
the compound No. 1.001+trifloxystrobin+fluazinam;
the compound No. 1.001+fludioxonil+cyprodinil;
the compound No. 1.001+fludioxonil+fluazinam; and
the compound No. 1.001+cyprodinil+fluazinam.

The active ingredient combinations are effective against harmful microorganisms, such as microorganisms, that cause phytopathogenic diseases, in particular against phytopathogenic fungi and bacteria.

The active ingredient combinations are effective especially against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Phakopsora, Puccinia, Ustilago, Tilletia); Fungi imperfecti (also known as Deuteromycetes; e.g. Botrytis, Helminthosporium, Rhynchosporium, Fusarium, Septoria, Cercospora, Alternaria, Pyricularia and Pseudocercosporella); Oomycetes (e.g. Phytophthora, Peronospora, Pseudoperonospora, Albugo, Bremia, Pythium, Pseudosclerospora, Plasmopara).

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins, for example insecticidal proteins from Bacillus cereus or Bacillus popliae; or insecticidal proteins from Bacillus thuringiensis, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a CryIIIB (b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein CryI F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer. Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Useful plants of elevated interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

A further aspect of the instant invention is a method of protecting natural substances of plant and/or animal origin, which have been taken from the natural life cycle, and/or their processed forms against attack of fungi, which comprises applying to said natural substances of plant and/or animal origin or their processed forms a combination of components (A) and (B) and (C) in a synergistically effective amount.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

The combinations according the present invention can prevent disadvantageous effects such as decay, discoloration or mold.

A preferred embodiment is a method of protecting natural substances of plant origin, which have been taken from the natural life cycle, and/or their processed forms against attack of fungi, which comprises applying to said natural substances of plant and/or animal origin or their processed forms a combination of components (A) and (B) and (C) in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components (A) and (B) and (C) in a synergistically effective amount.

The combinations of the present invention may also be used in the field of protecting industrial material against attack of fungi. According to the instant invention, the term "industrial material" denotes non-live material which have been prepared for use in industry. For example, industrial materials which are intended to be protected against attack of fungi can be glues, sizes, paper, board, textiles, carpets, leather, wood, constructions, paints, plastic articles, cooling lubricants, aqueous hydraulic fluids and other materials which can be infested with, or decomposed by, microorganisms. Cooling and heating systems, ventilation and air conditioning systems and parts of production plants, for example cooling-water circuits, which may be impaired by multiplication of microorganisms may also be mentioned from amongst the materials to be protected. The combinations according the present invention can prevent disadvantageous effects such as decay, discoloration or mold.

The combinations of the present invention may also be used in the field of protecting technical material against attack of fungi. According to the instant invention, the term "technical material" includes paper; carpets; constructions; cooling and heating systems; ventilation and air conditioning systems and the like. The combinations according the present invention can prevent disadvantageous effects such as decay, discoloration or mold.

The combinations according to the present invention are particularly effective against powdery mildews; rusts; leafspot species; early blights and molds; especially against *Septoria, Puccinia, Erysiphe, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The combinations according to the present invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gäumannomyces graminis , Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The combinations according to the present invention are furthermore particularly effective against post harvest diseasese such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum,*

*Penicilium solitum*, *Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

It has been found that the use of components (B) and (C) in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

The active ingredient mixture of the compounds of formula I selected from table 1 and 2 with active ingredients (B+C) described above comprises a compound selected from table 1 and 2 and an active ingredient as described above preferably in a mixing ratio of from 1000:1 to 1:1000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In a preferred embodiment of the invention, the ratios by weight of component (A) selected from table 1 and 2 to the mixture of components (B) and (C) are 4:1 to 1:4.

In a preferred embodiment of the invention, ratios by weight of component (B) to component (C) are from 2:1 to 1:6.

The mixtures comprising a compound of formula I selected from table 1 and 2 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from table 1 and the active ingredients as described above is not essential for working the present invention.

The synergistic activity of the combination is apparent from the fact that the fungicidal activity of the composition of (A)+(B)+(C) is greater than the sum of the fungicidal activities of (the mixture of A+B) and (C), or (the mixture of A+C) and (B) or (A) and (B) and (C).

The method of the invention comprises applying to the useful plants, the locus thereof or propagation material thereof in admixture or separately, a synergistically effective aggregate amount of a component (A) and a component (B) and a component (C).

Some of said combinations according to the invention have a systemic action and can be used as foliar, soil and seed treatment fungicides.

With the combinations according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The combinations of the present invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the fungi, the useful plants, the locus thereof, the propagation material thereof, the natural substances of plant and/or animal origin, which have been taken from the natural life cycle, and/or their processed forms, or the industrial materials threatened by fungus attack with a combination of components (A) and (B) and (C), preferably in a synergistically effective amount.

The combinations according to the invention may be applied before or after infection of the useful plants, the propagation material thereof, the natural substances of plant and/or animal origin, which have been taken from the natural life cycle, and/or their processed forms, or the industrial materials by the fungi.

The combinations according to the invention are particularly useful for controlling the following plant diseases:
*Alternaria* species in fruit and vegetables,
*Ascochyta* species in pulse crops,
*Botrytis cinerea* in strawberries, tomatoes, sunflower, pulse crops, vegetables and grapes,
*Cercospora arachidicola* in peanuts,
*Cochliobolus sativus* in cereals,
*Colletotrichum* species in pulse crops,
*Erysiphe species* in cereals,
*Erysiphe cichoracearum* and *Sphaerotheca fuliginea* in cucurbits,
*Fusarium* species in cereals and maize,
*Gäumannomyces graminis* in cereals and lawns,
*Helminthosporium* species in maize, rice and potatoes,
*Hemileia vastatrix* on coffee,
*Microdochium* species in wheat and rye,
*Phakopsora* species in soybean,
*Puccinia* species in cereals, broadleaf crops and perrenial plants,
*Pseudocercosporella* species in cereals,
*Phragmidium mucronatum* in roses,
*Podosphaera* species in fruits,
*Pyrenophora* species in barley,
*Pyricularia oryzae* in rice,
*Ramularia collo*-cygni in barley,
*Rhizoctonia* species in cotton, soybean, cereals, maize, potatoes, rice and lawns,
*Rhynchosporium secalis* in barley and rye,
*Sclerotinia* species in lawns, lettuce, vegetables and oil seed rape,
*Septoria* species in cereals, soybean and vegetables,
*Sphacelotheca reilliana* in maize,
*Tilletia* species in cereals,

*Uncinula necator, Guignardia bidwellii* and *Phomopsis viticola* in vines,
*Urocystis occulta* in rye,
*Ustilago* species in cereals and maize,
*Venturia* species in fruits,
*Monilinia* species on fruits,
*Penicillium* species on citrus and apples.

The combinations according to the invention are preventively and/or curatively valuable active ingredients in the field of pest control, even at low rates of application, which have a very favorable biocidal spectrum and are well tolerated by warm-blooded species, fish and plants. The active ingredients according to the invention which are partially known for their insecticidal action act against all or individual developmental stages of normally sensitive, but also resistant, animal pests, such as insects or representatives of the order Acarina. The insecticidal or acaricidal activity of the combinations according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order *Acarina*, for example,

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order *Anoplura*, for example,

*Haematopinus* spp., *Linognathus* spp., *Pediculus* spp., *Pemphigus* spp. and *Phylloxera* spp.;
from the order *Coleoptera*, for example, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;
from the order *Diptera*, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order *Heteroptera*, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order *Homoptera*, for example,

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphum* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;*
from the order *Hymenoptera*, for example,

*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;
from the order *Isoptera*, for example,

*Reticulitermes* spp.;
from the order *Lepidoptera*, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis*spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order *Mallophaga*, for example,

*Damalinea* spp. and *Trichodectes* spp.;
from the order *Orthoptera*, for example,

*Blatta* spp., *Blattella* spp., *Gryllotalpa* spp., *Leucophaea maderae, Locusta* spp., *Periplaneta* spp. and *Schistocerca* spp.;
from the order *Psocoptera*, for example,

*Liposcelis* spp.;
from the order *Siphonaptera*, for example,

*Ceratophyllus* spp., *Ctenocephalides* spp. and *Xenopsylla cheopis;*
from the order *Thysanoptera*, for example,

*Frankliniella* spp., *Hercinothrips* spp., *Scirtothrips aurantii, Taeniothrips* spp., *Thrips palmi* and *Thrips tabaci;*
from the order *Thysanura*, for example,

*Lepisma saccharina;*
nematodes, for example root knot nematodes, stem eelworms and foliar nematodes;
especially *Heterodera* spp., for example *Heterodera schachtii, Heterodora avenae* and *Heterodora trifolii;* *Globodera* spp., for example *Globodera rostochiensis;* *Meloidogyne* spp., for example *Meloidogyne incoginita* and *Meloidogyne javanica;* *Radopholus* spp., for example *Radopholus similis;* *Pratylenchus,* for example *Pratylenchus neglectans* and *Pratylenchus penetrans;* *Tylenchulus,* for example *Tylenchulus semipenetrans;* *Longidorus, Trichodorus, Xiphinema, Ditylenchus, Aphelenchoides* and *Anguina;* cruciferflea beetles (*Phyllotreta* spp.);
root maggots (*Delia* spp.) and
cabbage seedpod weevil (*Ceutorhynchus* spp.).

The combinations according to the invention can be used for controlling, i. e. containing or destroying, animal pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these animal pests.

When applied to the useful plants the compound of formula I is applied at a rate of 5 to 2000 g a.i./ha, particularly 10 to 1000 g a.i./ha, e.g. 50, 75, 100 or 200 g a.i./ha, in association with 1 to 5000 g a.i./ha, particularly 2 to 2000 g a.i./ha, e.g. 100, 250, 500, 800, 1000, 1500 g a.i./ha of component (B) and (C), depending on the class of chemical employed as component (B) and (C).

In agricultural practice the application rates of the combination according to the invention depend on the type of effect desired, and typically range from 20 to 4000 g of total combination per hectare.

When the combinations of the present invention are used for treating seed, rates of 0.001 to 50 g of a compound of formula I per kg of seed, preferably from 0.01 to 10g per kg of seed, and 0.001 to 50 g of a compound of component (B), per kg of seed, preferably from 0.01 to 10 g per kg of seed, are generally sufficient.

The invention also provides fungicidal compositions comprising a combination of components (A) and (B) and (C) as mentioned above in a synergistically effective amount, together with an agriculturally acceptable carrier, and optionally a surfactant. In said compositions, the weight ratio of (A) to (B+C) is preferably between 1000:1 and 1:1000. In a preferred embodiment of the invention, the ratios by weight in said compositions of component (A) to the mixture of components (B) and (C) are 4:1 to 1:4. In a preferred embodiment of the invention, ratios by weight of component (B) to component (C) in said compositions are from 2:1 to 1:6.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention, "active ingredient" denoting a mixture of compound I and compounds of component (B+C) in a specific mixing ratio.

FORMULATION EXAMPLES

| Wettable powders | a) | b) | c) |
|---|---|---|---|
| active ingredient [I:comp (B + C) = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [I:comp (B) = 1:3(a), 1:2(b), 1:1(c)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient (I:comp (B + C) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [I:comp (B + C) = 1:6(a), 1:2(b), 1:10(c)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient (I:comp (B + C) = 2:1) | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient (I:comp (B + C) = 1:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:comp (B + C) = 1:8) | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient (I:comp (B + C) = 1:8) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I and a compound of components (B+C), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients.

The medium capsule diameter is 8-15 microns.

The resulting formulation is applied to seeds as an aqueous suspension in an apparatus suitable for that purpose.

Biological Examples

Liquid culture tests in well plates:

Mycelia fragments or conidia suspensions of a fungus, prepared either freshly from liquid cultures of the fungus or from cryogenic storage, were directly mixed into nutrient broth. DMSO solutions of the test compound (max. 10 mg/ml) was diluted with 0.025% Tween20 by factor 50 and 10 µl of this solution was pipetted into a microtiter plate (96-well format). The nutrient broth containing the fungal spores/mycelia fragments was then added to give an end concentration of the tested compound. The test plates were incubated in the dark at 24° C. and 96% rh. The inhibition of fungal growth was determined photometrically and visually after 2-4 days, depending on the pathosystem, and percent antifungal activity relative to the untreated check was calculated.

*Alternaria solani*/Liquid Culture:

*Conidia* of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically and visually 2-3 day after application.

*Botryotinia fuckeliana* (*Botrytis cinerea*)/Liquid Culture:

*Conidia* of the fungus from cryogenic storage were directly mixed into nutrient broth (Vogels broth). After placing a (DMSO) solution of test compound into a microtiter plate (96-well format), the nutrient broth containing the fungal spores was added. The test plates were incubated at 24° C. and the inhibition of growth was determined photometrically and visually 3 days after application.

*Fusarium culmorum*/Liquid Culture:

Conidia of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically and visually 3 days after application.

*Gaeumannomyces graminis*/Liquid Culture:

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically and visually 3-4 days after application.

*Monographella nivalis* (*Microdochium nivale*)/Liquid Culture:

Conidia of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically and visually 3-4 days after application.

*Mycosphaerella graminicola* (*Septoria tritici*)/Liquid Culture:

Conidia of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically and visually 4 days after application.

*Thanatephorus cucumeris* (*Rhizoctonia solani*)/Liquid Culture:

Mycelia fragments of a newly grown liquid culture of the fungus were directly mixed into nutrient broth (PDB potato dextrose broth). After placing a (DMSO) solution of the test compounds into a microtiter plate (96-well format), the nutrient broth containing the fungal material was added. The test plates were incubated at 24° C. and the inhibition of growth was determined photometrically and visually 3-4 days after application.

The results are shown in the following tables.

TABLE B1

The abbreviations are defined as follows:
1.001 = compound No. 1.001
STL = compound of formula VII
IZM = isopyrazam

| Solution of 1.001 ppm | Solution of STL + IZM (1:2) ppm | | observed % activity | exp. action (colby) |
|---|---|---|---|---|
| | ppm | ppm | | |
| B1.1: *Gaeumannomyces graminis*: | | | | |
| 0.2000 | | | 7 | |
| | 0.0165 | 0.0335 | 73 | |
| 0.2000 | 0.0165 | 0.0335 | 100 | 75 |

TABLE B1-continued

The abbreviations are defined as follows:
1.001 = compound No. 1.001
STL = compound of formula VII
IZM = isopyrazam

| Solution of 1.001 ppm | Solution of STL + IZM (1:2) ppm | | observed % activity | exp. action (colby) |
|---|---|---|---|---|
| | ppm | ppm | | |
| B1.2: *Alternaria solani*: | | | | |
| 0.0008 | | | 4 | |
| 0.0016 | | | 32 | |
| 0.0016 | | | 32 | |
| 0.0031 | | | 64 | |
| | 0.0001 | 0.0003 | 0 | |
| | 0.0003 | 0.0005 | 0 | |
| | 0.0005 | 0.0010 | 0 | |
| | 0.0010 | 0.0021 | 0 | |
| | 0.0021 | 0.0042 | 0 | |
| | 0.0041 | 0.0084 | 22 | |
| 0.0008 | 0.0001 | 0.0003 | 20 | 4 |
| 0.0008 | 0.0010 | 0.0021 | 49 | 4 |
| 0.0016 | 0.0001 | 0.0003 | 44 | 32 |
| 0.0016 | 0.0003 | 0.0005 | 46 | 32 |
| 0.0016 | 0.0005 | 0.0010 | 61 | 32 |
| 0.0016 | 0.0010 | 0.0021 | 49 | 32 |
| 0.0016 | 0.0021 | 0.0042 | 72 | 32 |
| 0.0031 | 0.0005 | 0.0010 | 71 | 64 |
| 0.0031 | 0.0010 | 0.0021 | 75 | 64 |
| 0.0031 | 0.0021 | 0.0042 | 78 | 64 |
| 0.0031 | 0.0041 | 0.0084 | 87 | 72 |
| B1.3: *Monographella nivalis*: | | | | |
| 0.0125 | | | 0 | |
| 0.0250 | | | 5 | |
| 0.0500 | | | 45 | |
| 0.2000 | | | 78 | |
| | 0.0083 | 0.0168 | 0 | |
| | 0.0165 | 0.0335 | 1 | |
| | 0.0330 | 0.0670 | 34 | |
| 0.0125 | 0.0165 | 0.0335 | 30 | 1 |
| 0.0250 | 0.0165 | 0.0335 | 41 | 6 |
| 0.0250 | 0.0330 | 0.0670 | 83 | 37 |
| 0.0500 | 0.0083 | 0.0168 | 59 | 45 |
| 0.0500 | 0.0165 | 0.0335 | 53 | 46 |
| 0.0500 | 0.0330 | 0.0670 | 75 | 64 |
| 0.2000 | 0.0165 | 0.0335 | 87 | 79 |
| B1.4: *Rhizoctonia solani*: | | | | |
| 0.0125 | | | 0 | |
| 0.0250 | | | 6 | |
| 0.1000 | | | 0 | |
| | 0.0083 | 0.0168 | 1 | |
| | 0.0165 | 0.0335 | 88 | |
| 0.0125 | 0.0165 | 0.0335 | 100 | 88 |
| 0.0250 | 0.0083 | 0.0168 | 59 | 7 |
| 0.0250 | 0.0165 | 0.0335 | 100 | 89 |
| 0.1000 | 0.0083 | 0.0168 | 51 | 1 |
| B1.5: *Septoria tritici*: | | | | |
| 0.0016 | | | 52 | |
| | 0.0010 | 0.0021 | 5 | |
| | 0.0021 | 0.0042 | 2 | |
| 0.0016 | 0.0010 | 0.0021 | 79 | 55 |
| 0.0016 | 0.0021 | 0.0042 | 71 | 53 |

TABLE B2

The abbreviations are defined as follows:
1.001 = compound No. 1.001
STL = compound of formula VII
DFZ = difenoconazole

| Solution of 1.001 ppm | Solution of STL + DFZ (3:5) ppm | | observed % activity | expected action (colby) |
|---|---|---|---|---|
| B2.1: *Gaeumannomyces graminis* | | | | |
| 0.0125 | | | 0 | |
| 0.0250 | | | 4 | |
| 0.0500 | | | 0 | |
| 0.1000 | | | 0 | |
|  | 0.0188 | 0.0313 | 44 | |
| 0.0125 | 0.0188 | 0.0313 | 89 | 44 |
| 0.0250 | 0.0188 | 0.0313 | 71 | 46 |
| 0.0500 | 0.0188 | 0.0313 | 64 | 44 |
| 0.1000 | 0.0188 | 0.0313 | 49 | 44 |
| B2.2: *Alternaria solani* | | | | |
| 0.0016 | | | 39 | |
|  | 0.0001 | 0.0002 | 0 | |
|  | 0.0003 | 0.0005 | 1 | |
|  | 0.0012 | 0.0020 | 4 | |
|  | 0.0023 | 0.0039 | 1 | |
| 0.0016 | 0.0001 | 0.0002 | 50 | 39 |
| 0.0016 | 0.0003 | 0.0005 | 48 | 39 |
| 0.0016 | 0.0012 | 0.0020 | 65 | 41 |
| 0.0016 | 0.0023 | 0.0039 | 66 | 39 |
| B2.3: *Monographella nivalis* | | | | |
| 0.0250 | | | 0 | |
| 0.0500 | | | 26 | |
|  | 0.0047 | 0.0078 | 9 | |
|  | 0.0094 | 0.0156 | 2 | |
|  | 0.0188 | 0.0313 | 12 | |
|  | 0.0375 | 0.0625 | 25 | |
| 0.0250 | 0.0375 | 0.0625 | 81 | 25 |
| 0.0500 | 0.0047 | 0.0078 | 72 | 33 |
| 0.0500 | 0.0094 | 0.0156 | 65 | 27 |
| 0.0500 | 0.0188 | 0.0313 | 42 | 35 |
| 0.0500 | 0.0375 | 0.0625 | 78 | 45 |

TABLE B3

The abbreviations are defined as follows:
1.001 = compound No. 1.001
STL = compound of formula VII
AZ = azoxystrobin

| Solution of 1.001 ppm | Solution of STL + AZ (1:2) ppm | | observed % activity | expected action (colby) |
|---|---|---|---|---|
| B3.1: *Gaeumannomyces graminis* | | | | |
| 0.0031 | | | 0 | |
| 0.0063 | | | 0 | |
| 0.0125 | | | 8 | |
| 0.0250 | | | 0 | |
| 0.0500 | | | 0 | |
|  | 0.0021 | 0.0042 | 12 | |
|  | 0.0041 | 0.0084 | 42 | |
| 0.0031 | 0.0041 | 0.0084 | 91 | 42 |
| 0.0063 | 0.0021 | 0.0042 | 38 | 12 |
| 0.0063 | 0.0041 | 0.0084 | 62 | 42 |
| 0.0125 | 0.0041 | 0.0084 | 90 | 47 |
| 0.0250 | 0.0021 | 0.0042 | 45 | 12 |
| 0.0250 | 0.0041 | 0.0084 | 93 | 42 |
| 0.0500 | 0.0041 | 0.0084 | 84 | 42 |
| B3.2: *Alternaria solani* | | | | |
| 0.0016 | | | 45 | |
| 0.0031 | | | 66 | |
|  | 0.0003 | 0.0005 | 3 | |
|  | 0.0005 | 0.0010 | 0 | |
|  | 0.0010 | 0.0021 | 0 | |
| 0.0016 | 0.0003 | 0.0005 | 67 | 47 |
| 0.0016 | 0.0010 | 0.0021 | 72 | 45 |
| 0.0031 | 0.0005 | 0.0010 | 81 | 66 |
| B3.3: *Fusarium culmorum* | | | | |
| 0.0250 | | | 19 | |
| 0.0500 | | | 48 | |
| 0.1000 | | | 55 | |
| 0.2000 | | | 59 | |
|  | 0.0165 | 0.0335 | 6 | |
|  | 0.0330 | 0.0670 | 0 | |
|  | 0.0660 | 0.1340 | 0 | |
|  | 0.0660 | 0.1340 | 0 | |
| 0.0250 | 0.0165 | 0.0335 | 30 | 24 |
| 0.0500 | 0.0330 | 0.0670 | 56 | 48 |
| 0.0500 | 0.0660 | 0.1340 | 62 | 48 |
| 0.1000 | 0.0660 | 0.1340 | 63 | 55 |
| 0.2000 | 0.0660 | 0.1340 | 69 | 59 |
| B3.4: *Monographella nivalis* | | | | |
| 0.0008 | | | 1 | |
|  | 0.0010 | 0.0021 | 60 | |
| 0.0008 | 0.0010 | 0.0021 | 77 | 61 |
| B3.5: *Septoria tritici* | | | | |
| 0.0016 | | | 42 | |
| 0.0031 | | | 83 | |
|  | 0.0010 | 0.0021 | 0 | |
|  | 0.0021 | 0.0042 | 4 | |
|  | 0.0041 | 0.0084 | 17 | |
| 0.0016 | 0.0010 | 0.0021 | 49 | 42 |
| 0.0016 | 0.0021 | 0.0042 | 65 | 45 |
| 0.0031 | 0.0041 | 0.0084 | 94 | 86 |

TABLE B4

The abbreviations are defined as follows:
1.001 = compound No. 1.001
STL = compound of formula VII
PTC = prothioconazole

| Solution of 1.001 ppm | Solution of STL + PTC (1:2) ppm | | observed % activity | expected action (colby) |
|---|---|---|---|---|
| B4.1: *Gaeumannomyces graminis* | | | | |
| 0.0125 | | | 0 | |
| 0.0250 | | | 0 | |
| 0.0500 | | | 0 | |
| 0.1000 | | | 0 | |
| 0.2000 | | | 12 | |
|  | 0.0165 | 0.0335 | 24 | |
|  | 0.0330 | 0.0670 | 88 | |
| 0.0125 | 0.0165 | 0.0335 | 79 | 24 |
| 0.0250 | 0.0330 | 0.0670 | 100 | 88 |
| 0.0500 | 0.0165 | 0.0335 | 88 | 24 |
| 0.1000 | 0.0165 | 0.0335 | 62 | 24 |
| 0.2000 | 0.0165 | 0.0335 | 74 | 33 |

TABLE B4-continued

The abbreviations are defined as follows:
1.001 = compound No. 1.001
STL = compound of formula VII
PTC = prothioconazole

| Solution of 1.001 ppm | Solution of STL + PTC (1:2) ppm | ppm | observed % activity | expected action (colby) |
|---|---|---|---|---|
| B4.2: *Alternaria solani*: | | | | |
| 0.0008 | | | 29 | |
| 0.0016 | | | 47 | |
| 0.0031 | | | 73 | |
| | 0.0001 | 0.0003 | 0 | |
| | 0.0010 | 0.0021 | 0 | |
| | 0.0021 | 0.0042 | 0 | |
| | 0.0041 | 0.0084 | 3 | |
| 0.0008 | 0.0010 | 0.0021 | 42 | 29 |
| 0.0016 | 0.0001 | 0.0003 | 63 | 47 |
| 0.0016 | 0.0021 | 0.0042 | 64 | 47 |
| 0.0031 | 0.0041 | 0.0084 | 86 | 74 |
| B4.3: *Monographella nivalis*: | | | | |
| 0.0500 | | | 15 | |
| 0.1000 | | | 64 | |
| | 0.0083 | 0.0168 | 4 | |
| | 0.0165 | 0.0335 | 0 | |
| 0.0500 | 0.0165 | 0.0335 | 83 | 15 |
| 0.1000 | 0.0083 | 0.0168 | 79 | 65 |

TABLE B5

The abbreviations are defined as follows:
1.001 = compound No. 1.001
STL = compound of formula VII
TCZ = tebuconazole

| Solution of 1.001 ppm | Solution of STL + TCZ (1:2) ppm | ppm | observed % activity | expected action (colby) |
|---|---|---|---|---|
| B5.1: *Gaeumannomyces graminis* | | | | |
| 0.0250 | | | 0 | |
| 0.0500 | | | 2 | |
| 0.1000 | | | 0 | |
| 0.2000 | | | 0 | |
| | 0.0165 | 0.0335 | 42 | |
| | 0.0330 | 0.0670 | 78 | |
| 0.0250 | 0.0165 | 0.0335 | 57 | 42 |
| 0.0250 | 0.0330 | 0.0670 | 100 | 78 |
| 0.0500 | 0.0330 | 0.0670 | 98 | 78 |
| 0.1000 | 0.0165 | 0.0335 | 61 | 42 |
| 0.1000 | 0.0330 | 0.0670 | 98 | 78 |
| 0.2000 | 0.0165 | 0.0335 | 68 | 42 |
| 0.2000 | 0.0330 | 0.0670 | 89 | 78 |
| B5.2: *Alternaria solani*: | | | | |
| 0.0008 | | | 3 | |
| 0.0016 | | | 36 | |
| 0.0031 | | | 75 | |
| | 0.0005 | 0.0010 | 0 | |
| | 0.0010 | 0.0021 | 0 | |
| | 0.0021 | 0.0042 | 0 | |
| 0.0008 | 0.0005 | 0.0010 | 31 | 3 |
| 0.0016 | 0.0010 | 0.0021 | 44 | 36 |
| 0.0016 | 0.0021 | 0.0042 | 64 | 36 |
| 0.0031 | 0.0010 | 0.0021 | 86 | 75 |
| B5.3: *Fusarium culmorum*: | | | | |
| 0.0250 | | | 9 | |
| 0.0500 | | | 39 | |
| | 0.0021 | 0.0042 | 2 | |
| | 0.0041 | 0.0084 | 1 | |

TABLE B5-continued

The abbreviations are defined as follows:
1.001 = compound No. 1.001
STL = compound of formula VII
TCZ = tebuconazole

| Solution of 1.001 ppm | Solution of STL + TCZ (1:2) ppm | ppm | observed % activity | expected action (colby) |
|---|---|---|---|---|
| | 0.0083 | 0.0168 | 4 | |
| 0.0250 | 0.0021 | 0.0042 | 32 | 11 |
| 0.0250 | 0.0041 | 0.0084 | 28 | 11 |
| 0.0500 | 0.0041 | 0.0084 | 52 | 40 |
| 0.0500 | 0.0083 | 0.0168 | 52 | 41 |
| B5.4: *Monographella nivalis*: | | | | |
| 0.0250 | | | 2 | |
| 0.0500 | | | 9 | |
| 0.1000 | | | 60 | |
| | 0.0083 | 0.0168 | 0 | |
| | 0.0165 | 0.0335 | 5 | |
| | 0.0330 | 0.0670 | 14 | |
| | 0.0660 | 0.1340 | 63 | |
| 0.0250 | 0.0165 | 0.0335 | 25 | 7 |
| 0.0250 | 0.0330 | 0.0670 | 53 | 16 |
| 0.0500 | 0.0083 | 0.0168 | 29 | 9 |
| 0.0500 | 0.0165 | 0.0335 | 41 | 13 |
| 0.0500 | 0.0330 | 0.0670 | 65 | 22 |
| 0.0500 | 0.0660 | 0.1340 | 84 | 66 |
| 0.1000 | 0.0083 | 0.0168 | 70 | 60 |
| 0.1000 | 0.0165 | 0.0335 | 76 | 62 |
| 0.1000 | 0.0330 | 0.0670 | 85 | 66 |
| B5.5: *Rhizoctonia solani*: | | | | |
| 0.0250 | | | 13 | |
| 0.0500 | | | 1 | |
| 0.1000 | | | 17 | |
| | 0.0330 | 0.0670 | 0 | |
| | 0.0660 | 0.1340 | 28 | |
| 0.0250 | 0.0330 | 0.0670 | 97 | 13 |
| 0.0500 | 0.0660 | 0.1340 | 87 | 29 |
| 0.1000 | 0.0660 | 0.1340 | 61 | 41 |
| B5.6: *Septoria tritici*: | | | | |
| 0.0008 | | | 27 | |
| 0.0016 | | | 45 | |
| 0.0031 | | | 82 | |
| | 0.0010 | 0.0021 | 0 | |
| | 0.0021 | 0.0042 | 5 | |
| | 0.0041 | 0.0084 | 0 | |
| 0.0008 | 0.0010 | 0.0021 | 36 | 27 |
| 0.0016 | 0.0010 | 0.0021 | 70 | 45 |
| 0.0016 | 0.0021 | 0.0042 | 60 | 47 |
| 0.0031 | 0.0041 | 0.0084 | 91 | 82 |

TABLE B6

The abbreviations are defined as follows:
1.001 = compound No. 1.001
STL = compound of formula VII
PYS = pyraclostrobin

| Solution of 1.001 ppm | Solution of STL + PYS (1:1) ppm | ppm | observed % activity | expected action (colby) |
|---|---|---|---|---|
| B6.1: *Gaeumannomyces graminis* | | | | |
| 0.0063 | | | 0 | |
| 0.0250 | | | 0 | |
| 0.1000 | | | 0 | |
| | 0.0125 | 0.0125 | 15 | |
| 0.0063 | 0.0125 | 0.0125 | 34 | 15 |
| 0.0250 | 0.0125 | 0.0125 | 46 | 15 |
| 0.1000 | 0.0125 | 0.0125 | 84 | 15 |

TABLE B6-continued

The abbreviations are defined as follows:
1.001 = compound No. 1.001
STL = compound of formula VII
PYS = pyraclostrobin

| Solution of 1.001 ppm | Solution of STL + PYS (1:1) ppm | ppm | observed % activity | expected action (colby) |
|---|---|---|---|---|
| B6.2: *Alternaria solani*: | | | | |
| 0.0016 | | | 35 | |
| 0.0031 | | | 71 | |
| | 0.0002 | 0.0002 | 0 | |
| | 0.0031 | 0.0031 | 0 | |
| | 0.0063 | 0.0063 | 0 | |
| 0.0016 | 0.0002 | 0.0002 | 45 | 35 |
| 0.0016 | 0.0031 | 0.0031 | 46 | 35 |
| 0.0031 | 0.0063 | 0.0063 | 80 | 71 |
| B6.3: *Monographella nivalis*: | | | | |
| 0.0016 | | | 0 | |
| 0.0031 | | | 3 | |
| | 0.0031 | 0.0031 | 4 | |
| | 0.0063 | 0.0063 | 78 | |
| 0.0016 | 0.0031 | 0.0031 | 28 | 4 |
| 0.0031 | 0.0063 | 0.0063 | 92 | 78 |
| B6.4: *Septoria tritici*: | | | | |
| 0.0008 | | | 11 | |
| 0.0016 | | | 53 | |
| 0.0031 | | | 89 | |
| | 0.0002 | 0.0002 | 3 | |
| | 0.0016 | 0.0016 | 3 | |
| | 0.0031 | 0.0031 | 2 | |
| | 0.0063 | 0.0063 | 1 | |
| 0.0008 | 0.0016 | 0.0016 | 28 | 14 |
| 0.0016 | 0.0002 | 0.0002 | 66 | 54 |
| 0.0016 | 0.0031 | 0.0031 | 69 | 54 |
| 0.0031 | 0.0063 | 0.0063 | 97 | 89 |

TABLE B7

The abbreviations are defined as follows:
1.001 = compound No. 1.001
STL = compound of formula VII
TFS = trifloxystrobin

| Solution of 1.001 ppm | Solution of STL + TFS (1:1) ppm | ppm | observed % activity | expected action (colby) |
|---|---|---|---|---|
| B7.1: *Gaeumannomyces graminis* | | | | |
| 0.0063 | | | 0 | |
| 0.0125 | | | 4 | |
| 0.0250 | | | 2 | |
| 0.0500 | | | 3 | |
| 0.1000 | | | 0 | |
| 0.2000 | | | 0 | |
| | 0.0125 | 0.0125 | 19 | |
| | 0.0250 | 0.0250 | 53 | |
| 0.0063 | 0.0125 | 0.0125 | 71 | 19 |
| 0.0125 | 0.0250 | 0.0250 | 92 | 55 |
| 0.0250 | 0.0250 | 0.0250 | 90 | 54 |
| 0.0500 | 0.0125 | 0.0125 | 44 | 21 |
| 0.0500 | 0.0250 | 0.0250 | 74 | 55 |
| 0.1000 | 0.0250 | 0.0250 | 92 | 53 |
| 0.2000 | 0.0250 | 0.0250 | 92 | 53 |
| B7.2: *Alternaria solani*: | | | | |
| 0.0016 | | | 28 | |
| 0.0031 | | | 66 | |
| | 0.0002 | 0.0002 | 4 | |
| | 0.0004 | 0.0004 | 0 | |
| | 0.0016 | 0.0016 | 0 | |
| | 0.0031 | 0.0031 | 0 | |
| | 0.0063 | 0.0063 | 5 | |
| 0.0016 | 0.0002 | 0.0002 | 41 | 31 |
| 0.0016 | 0.0004 | 0.0004 | 42 | 28 |
| 0.0016 | 0.0016 | 0.0016 | 43 | 28 |
| 0.0016 | 0.0031 | 0.0031 | 57 | 28 |
| 0.0031 | 0.0004 | 0.0004 | 75 | 66 |
| 0.0031 | 0.0031 | 0.0031 | 76 | 66 |
| 0.0031 | 0.0063 | 0.0063 | 81 | 68 |
| B7.3: *Fusarium culmorum*: | | | | |
| 0.0125 | | | 11 | |
| 0.0250 | | | 24 | |
| 0.0500 | | | 49 | |
| 0.1000 | | | 58 | |
| 0.2000 | | | 60 | |
| | 0.0031 | 0.0031 | 2 | |
| | 0.0063 | 0.0063 | 0 | |
| | 0.0125 | 0.0125 | 1 | |
| | 0.0250 | 0.0250 | 9 | |
| | 0.0500 | 0.0500 | 5 | |
| | 0.1000 | 0.1000 | 10 | |
| 0.0125 | 0.0250 | 0.0250 | 47 | 18 |
| 0.0250 | 0.0031 | 0.0031 | 38 | 25 |
| 0.0250 | 0.0063 | 0.0063 | 36 | 24 |
| 0.0250 | 0.0125 | 0.0125 | 35 | 24 |
| 0.0250 | 0.0250 | 0.0250 | 62 | 30 |
| 0.0250 | 0.0500 | 0.0500 | 69 | 28 |
| 0.0500 | 0.0063 | 0.0063 | 54 | 49 |
| 0.0500 | 0.0125 | 0.0125 | 62 | 49 |
| 0.0500 | 0.0250 | 0.0250 | 69 | 53 |
| 0.0500 | 0.0500 | 0.0500 | 77 | 52 |
| 0.0500 | 0.1000 | 0.1000 | 81 | 54 |
| 0.1000 | 0.0125 | 0.0125 | 65 | 58 |
| 0.1000 | 0.0250 | 0.0250 | 71 | 61 |
| 0.1000 | 0.0500 | 0.0500 | 75 | 60 |
| 0.1000 | 0.1000 | 0.1000 | 82 | 62 |
| 0.2000 | 0.0250 | 0.0250 | 75 | 63 |
| 0.2000 | 0.0500 | 0.0500 | 76 | 62 |
| 0.2000 | 0.1000 | 0.1000 | 83 | 64 |
| B7.4: *Rhizoctonia solani*: | | | | |
| 0.0125 | | | 3 | |
| 0.0250 | | | 8 | |
| | 0.0125 | 0.0125 | 0 | |
| 0.0125 | 0.0125 | 0.0125 | 96 | 3 |
| 0.0250 | 0.0125 | 0.0125 | 100 | 8 |
| B7.5: *Septoria tritici*: | | | | |
| 0.0016 | | | 53 | |
| | 0.0031 | 0.0031 | 42 | |
| 0.0016 | 0.0031 | 0.0031 | 89 | 72 |

TABLE B8

The abbreviations are defined as follows:
1.001 = compound No. 1.001
STL = compound of formula VII
FDL = fludioxonil

| Solution of 1.001 ppm | Solution of STL + FDL (1:4) | | observed % activity | expected action (colby) |
|---|---|---|---|---|
| | ppm | ppm | | |
| B8.1: *Gaeumannomyces graminis* | | | | |
| 0.0250 | | | 0 | |
| 0.0500 | | | 0 | |
| 0.1000 | | | 0 | |
| 0.2000 | | | 0 | |
| | 0.0100 | 0.0400 | 16 | |
| | 0.0200 | 0.0800 | 52 | |
| 0.0250 | 0.0200 | 0.0800 | 100 | 52 |
| 0.0500 | 0.0200 | 0.0800 | 100 | 52 |
| 0.1000 | 0.0200 | 0.0800 | 100 | 52 |
| 0.2000 | 0.0100 | 0.0400 | 61 | 16 |
| 0.2000 | 0.0200 | 0.0800 | 96 | 52 |
| B8.2: *Alternaria solani* | | | | |
| 0.0008 | | | 19 | |
| 0.0016 | | | 42 | |
| 0.0031 | | | 68 | |
| | 0.0006 | 0.0025 | 0 | |
| | 0.0013 | 0.0050 | 0 | |
| | 0.0025 | 0.0100 | 0 | |
| 0.0008 | 0.0006 | 0.0025 | 40 | 19 |
| 0.0016 | 0.0013 | 0.0050 | 60 | 42 |
| 0.0031 | 0.0025 | 0.0100 | 80 | 68 |
| B8.3: *Fusarium culmorum*: | | | | |
| 0.0250 | | | 18 | |
| 0.0500 | | | 51 | |
| 0.2000 | | | 55 | |
| | 0.0100 | 0.0400 | 9 | |
| | 0.0200 | 0.0800 | 15 | |
| 0.0250 | 0.0100 | 0.0400 | 42 | 25 |
| 0.0250 | 0.0200 | 0.0800 | 76 | 30 |
| 0.0500 | 0.0200 | 0.0800 | 91 | 58 |
| 0.2000 | 0.0200 | 0.0800 | 71 | 62 |

TABLE B9

The abbreviations are defined as follows:
1.001 = compound No. 1.001
STL = compound of formula VII
CPL = cyprodinil

| Solution of 1.001 ppm | Solution of STL + CPL (1:4) | | observed % activity | expected action (colby) |
|---|---|---|---|---|
| | ppm | ppm | | |
| B9.1: *Gaeumannomyces graminis* | | | | |
| 0.0125 | | | 0 | |
| 0.0250 | | | 0 | |
| 0.0500 | | | 0 | |
| 0.1000 | | | 0 | |
| 0.2000 | | | 0 | |
| | 0.0100 | 0.0400 | 0 | |
| | 0.0200 | 0.0800 | 30 | |
| 0.0125 | 0.0100 | 0.0400 | 39 | 0 |
| 0.0250 | 0.0200 | 0.0800 | 88 | 30 |
| 0.0500 | 0.0200 | 0.0800 | 56 | 30 |
| 0.1000 | 0.0200 | 0.0800 | 55 | 30 |
| 0.2000 | 0.0200 | 0.0800 | 66 | 30 |
| B9.2: *Alternaria solani*: | | | | |
| 0.0016 | | | 37 | |
| 0.0031 | | | 67 | |
| | 0.0002 | 0.0006 | 0 | |
| | 0.0013 | 0.0050 | 0 | |
| | 0.0025 | 0.0100 | 0 | |
| 0.0016 | 0.0002 | 0.0006 | 41 | 37 |
| 0.0016 | 0.0013 | 0.0050 | 43 | 37 |
| 0.0031 | 0.0025 | 0.0100 | 75 | 67 |
| B9.3: *Rhizoctonia solani*: | | | | |
| 0.0500 | | | 0 | |
| 0.2000 | | | 6 | |
| | 0.0200 | 0.0800 | 0 | |
| 0.0500 | 0.0200 | 0.0800 | 99 | 0 |
| 0.2000 | 0.0200 | 0.0800 | 69 | 6 |

TABLE B10

The abbreviations are defined as follows:
1.001 = compound No. 1.001
STL = compound of formula VII
FLN = fluazinam

| Solution of 1.001 ppm | Solution of STL + FLN (1:6) | | observed % activity | expected action (colby) |
|---|---|---|---|---|
| | ppm | ppm | | |
| B10.1: *Gaeumannomyces graminis* | | | | |
| 0.0125 | | | 0 | |
| 0.0250 | | | 0 | |
| 0.0500 | | | 0 | |
| 0.1000 | | | 0 | |
| 0.2000 | | | 0 | |
| | 0.0036 | 0.0214 | 3 | |
| | 0.0072 | 0.0428 | 40 | |
| | 0.0143 | 0.0857 | 91 | |
| | 0.0286 | 0.1714 | 90 | |
| 0.0125 | 0.0072 | 0.0428 | 83 | 40 |
| 0.0250 | 0.0072 | 0.0428 | 89 | 40 |
| 0.0250 | 0.0143 | 0.0857 | 100 | 91 |
| 0.0500 | 0.0286 | 0.1714 | 100 | 90 |
| 0.1000 | 0.0036 | 0.0214 | 51 | 3 |
| 0.1000 | 0.0286 | 0.1714 | 100 | 90 |
| 0.2000 | 0.0072 | 0.0428 | 76 | 40 |
| B10.2: *Alternaria solani*: | | | | |
| 0.0016 | | | 38 | |
| | 0.0001 | 0.0003 | 0 | |
| | 0.0009 | 0.0054 | 0 | |
| 0.0016 | 0.0001 | 0.0003 | 55 | 38 |
| 0.0016 | 0.0009 | 0.0054 | 52 | 38 |
| B10.3: *Monographella nivalis*: | | | | |
| 0.0063 | | | 0 | |
| 0.0125 | | | 0 | |
| 0.0250 | | | 0 | |
| 0.0500 | | | 16 | |
| 0.1000 | | | 61 | |
| 0.2000 | | | 85 | |
| | 0.0036 | 0.0214 | 8 | |
| | 0.0072 | 0.0428 | 37 | |
| 0.0063 | 0.0036 | 0.0214 | 26 | 8 |
| 0.0125 | 0.0072 | 0.0428 | 98 | 37 |
| 0.0250 | 0.0072 | 0.0428 | 95 | 38 |
| 0.0500 | 0.0072 | 0.0428 | 84 | 47 |
| 0.1000 | 0.0036 | 0.0214 | 82 | 64 |
| 0.1000 | 0.0072 | 0.0428 | 94 | 76 |
| 0.2000 | 0.0072 | 0.0428 | 100 | 90 |

TABLE B10-continued

The abbreviations are defined as follows:
1.001 = compound No. 1.001
STL = compound of formula VII
FLN = fluazinam

| Solution of 1.001 ppm | Solution of STL + FLN (1:6) ppm | ppm | observed % activity | expected action (colby) |
|---|---|---|---|---|
| B10.4: *Rhizoctonia solani*: | | | | |
| 0.0250 | | | 0 | |
| 0.0500 | | | 0 | |
| | 0.0143 | 0.0857 | 0 | |
| 0.0250 | 0.0143 | 0.0857 | 100 | 0 |
| 0.0500 | 0.0143 | 0.0857 | 71 | 0 |

TABLE B11

The abbreviations are defined as follows:
1.001 = compound No. 1.001
IZM = isopyrazam
DFZ: difenoconazole

| Solution of 1.001 ppm | Solution of IZM + DFZ (1:1) ppm | ppm | observed % activity | expected action (colby) |
|---|---|---|---|---|
| B11.1: *Gaeumannomyces graminis*: | | | | |
| 0.1000 | | | 0 | |
| | 0.0500 | 0.0500 | 0 | |
| 0.1000 | 0.0500 | 0.0500 | 57 | 0 |
| B11.2: *Alternaria solani*: | | | | |
| 0.0008 | | | 24 | |
| 0.0016 | | | 48 | |
| | 0.0016 | 0.0016 | 10 | |
| | 0.0031 | 0.0031 | 9 | |
| 0.0008 | 0.0016 | 0.0016 | 45 | 31 |
| 0.0016 | 0.0031 | 0.0031 | 63 | 53 |
| B11.3: *Monographella nivalis*: | | | | |
| 0.0500 | | | 36 | |
| 0.1000 | | | 69 | |
| | 0.0063 | 0.0063 | 0 | |
| | 0.0125 | 0.0125 | 0 | |
| | 0.1000 | 0.1000 | 2 | |
| 0.0500 | 0.0063 | 0.0063 | 54 | 36 |
| 0.1000 | 0.0125 | 0.0125 | 82 | 69 |
| 0.1000 | 0.1000 | 0.1000 | 89 | 70 |
| B11.4: *Rhizoctonia solani*: | | | | |
| 0.0125 | | | 0 | |
| 0.0250 | | | 8 | |
| 0.0500 | | | 0 | |
| 0.2000 | | | 0 | |
| | 0.0250 | 0.0250 | 17 | |
| | 0.0500 | 0.0500 | 36 | |
| 0.0125 | 0.0250 | 0.0250 | 37 | 17 |
| 0.0250 | 0.0500 | 0.0500 | 52 | 41 |
| 0.0500 | 0.0500 | 0.0500 | 72 | 36 |
| 0.2000 | 0.0250 | 0.0250 | 44 | 17 |
| 0.2000 | 0.0500 | 0.0500 | 56 | 36 |

TABLE B12

The abbreviations are defined as follows:
1.001 = compound No. 1.001
IZM = isopyrazam
AZO: azoxystrobin

| Solution of 1.001 ppm | Solution of IZM + AZO (1:1) ppm | ppm | observed % activity | expected action (colby) |
|---|---|---|---|---|
| B12.1: *Gaeumannomyces graminis*: | | | | |
| 0.0016 | | | 0 | |
| 0.0031 | | | 0 | |
| 0.0063 | | | 0 | |
| 0.0125 | | | 0 | |
| | 0.0031 | 0.0031 | 45 | |
| 0.0016 | 0.0031 | 0.0031 | 79 | 45 |
| 0.0031 | 0.0031 | 0.0031 | 92 | 45 |
| 0.0063 | 0.0031 | 0.0031 | 68 | 45 |
| 0.0125 | 0.0031 | 0.0031 | 80 | 45 |
| B12.2: *Alternaria solani*: | | | | |
| 0.0008 | | | 33 | |
| 0.0016 | | | 46 | |
| | 0.0002 | 0.0002 | 5 | |
| | 0.0016 | 0.0016 | 8 | |
| | 0.0031 | 0.0031 | 14 | |
| 0.0008 | 0.0016 | 0.0016 | 58 | 38 |
| 0.0016 | 0.0002 | 0.0002 | 78 | 48 |
| 0.0016 | 0.0031 | 0.0031 | 77 | 53 |
| B12.3: *Monographella nivalis*: | | | | |
| 0.0031 | | | 1 | |
| 0.0063 | | | 1 | |
| 0.0250 | | | 0 | |
| 0.0500 | | | 29 | |
| | 0.0063 | 0.0063 | 79 | |
| 0.0031 | 0.0063 | 0.0063 | 100 | 79 |
| 0.0063 | 0.0063 | 0.0063 | 93 | 79 |
| 0.0250 | 0.0063 | 0.0063 | 100 | 79 |
| 0.0500 | 0.0063 | 0.0063 | 98 | 85 |
| B12.4: *Rhizoctonia solani*: | | | | |
| 0.0063 | | | 0 | |
| 0.0125 | | | 0 | |
| 0.0250 | | | 0 | |
| 0.0500 | | | 0 | |
| 0.1000 | | | 3 | |
| 0.2000 | | | 17 | |
| | 0.0125 | 0.0125 | 54 | |
| | 0.0250 | 0.0250 | 69 | |
| | 0.0500 | 0.0500 | 85 | |
| 0.0063 | 0.0125 | 0.0125 | 91 | 54 |
| 0.0125 | 0.0250 | 0.0250 | 88 | 69 |
| 0.0250 | 0.0250 | 0.0250 | 96 | 69 |
| 0.0250 | 0.0500 | 0.0500 | 100 | 85 |
| 0.0500 | 0.0125 | 0.0125 | 60 | 54 |
| 0.0500 | 0.0250 | 0.0250 | 76 | 69 |
| 0.0500 | 0.0500 | 0.0500 | 95 | 85 |
| 0.1000 | 0.0250 | 0.0250 | 84 | 70 |
| 0.1000 | 0.0500 | 0.0500 | 100 | 85 |
| 0.2000 | 0.0250 | 0.0250 | 87 | 74 |
| 0.2000 | 0.0500 | 0.0500 | 99 | 87 |

TABLE B13

The abbreviations are defined as follows:
1.001 = compound No. 1.001
IZM = isopyrazam
PTC: prothioconazole

| Solution of 1.001 ppm | Solution of IZM + PTC (1:1) ppm | ppm | observed % activity | expected action (colby) |
|---|---|---|---|---|
| B13.1: *Alternaria solani*: | | | | |
| 0.0008 | | | 20 | |
| 0.0016 | | | 51 | |
| 0.0031 | | | 78 | |
| | 0.0004 | 0.0004 | 16 | |
| | 0.0008 | 0.0008 | 5 | |
| | 0.0016 | 0.0016 | 10 | |
| | 0.0031 | 0.0031 | 12 | |
| 0.0008 | 0.0004 | 0.0004 | 45 | 32 |
| 0.0008 | 0.0008 | 0.0008 | 48 | 23 |
| 0.0008 | 0.0016 | 0.0016 | 60 | 27 |
| 0.0016 | 0.0016 | 0.0016 | 65 | 56 |
| 0.0016 | 0.0031 | 0.0031 | 65 | 57 |
| 0.0031 | 0.0004 | 0.0004 | 96 | 82 |
| B13.2: *Monographella nivalis*: | | | | |
| 0.0250 | | | 8 | |
| 0.1000 | | | 61 | |
| | 0.0125 | 0.0125 | 0 | |
| | 0.0500 | 0.0500 | 21 | |
| 0.0250 | 0.0500 | 0.0500 | 51 | 27 |
| 0.1000 | 0.0125 | 0.0125 | 87 | 61 |
| B13.3: *Rhizoctonia solani*: | | | | |
| 0.0250 | | | 0 | |
| 0.0500 | | | 0 | |
| 0.2000 | | | 0 | |
| | 0.0500 | 0.0500 | 37 | |
| 0.0250 | 0.0500 | 0.0500 | 55 | 37 |
| 0.0500 | 0.0500 | 0.0500 | 58 | 37 |
| 0.2000 | 0.0500 | 0.0500 | 61 | 37 |

TABLE B14

The abbreviations are defined as follows:
1.001 = compound No. 1.001
IZM = isopyrazam
TCZ: tebuconazole

| Solution of 1.001 ppm | Solution of IZM + TCZ (1:1) ppm | ppm | observed % activity | expected action (colby) |
|---|---|---|---|---|
| B14.1: *Gaeumannomyces graminis*: | | | | |
| 0.1000 | | | 12 | |
| 0.2000 | | | 0 | |
| | 0.1000 | 0.1000 | 0 | |
| | 0.1000 | 0.1000 | 51 | |
| 0.1000 | 0.1000 | 0.1000 | 76 | 57 |
| 0.2000 | 0.1000 | 0.1000 | 100 | 51 |
| B14.2: *Alternaria solani*: | | | | |
| 0.0004 | | | 9 | |
| 0.0008 | | | 24 | |
| 0.0016 | | | 52 | |
| 0.0031 | | | 83 | |
| | 0.0002 | 0.0002 | 7 | |
| | 0.0004 | 0.0004 | 7 | |
| | 0.0008 | 0.0008 | 9 | |
| | 0.0016 | 0.0016 | 6 | |
| | 0.0031 | 0.0031 | 17 | |
| 0.0004 | 0.0004 | 0.0004 | 24 | 15 |
| 0.0008 | 0.0008 | 0.0008 | 37 | 31 |
| 0.0008 | 0.0016 | 0.0016 | 49 | 29 |
| 0.0016 | 0.0002 | 0.0002 | 73 | 56 |
| 0.0016 | 0.0016 | 0.0016 | 62 | 55 |
| 0.0016 | 0.0031 | 0.0031 | 80 | 61 |
| 0.0031 | 0.0004 | 0.0004 | 94 | 84 |
| B14.3: *Monographella nivalis*: | | | | |
| 0.0500 | | | 17 | |
| 0.1000 | | | 67 | |
| | 0.0063 | 0.0063 | 0 | |
| | 0.0125 | 0.0125 | 0 | |
| 0.0500 | 0.0063 | 0.0063 | 34 | 17 |
| 0.1000 | 0.0125 | 0.0125 | 81 | 67 |
| B14.4: *Rhizoctonia solani*: | | | | |
| 0.0125 | | | 0 | |
| 0.0250 | | | 0 | |
| 0.0500 | | | 3 | |
| 0.1000 | | | 7 | |
| | 0.0250 | 0.0250 | 28 | |
| | 0.0500 | 0.0500 | 76 | |
| | 0.1000 | 0.1000 | 78 | |
| 0.0125 | 0.0250 | 0.0250 | 57 | 28 |
| 0.0250 | 0.0500 | 0.0500 | 87 | 76 |
| 0.0500 | 0.1000 | 0.1000 | 97 | 78 |
| 0.1000 | 0.1000 | 0.1000 | 89 | 79 |

TABLE B15

The abbreviations are defined as follows:
1.001 = compound No. 1.001
IZM = isopyrazam
PYS: pyraclostrobin

| Solution of 1.001 ppm | Solution of IZM + PYS (2:1) ppm | ppm | observed % activity | expected action (colby) |
|---|---|---|---|---|
| B15.1: *Alternaria solani*: | | | | |
| 0.0008 | | | 36 | |
| 0.0016 | | | 56 | |
| 0.0031 | | | 82 | |
| | 0.0005 | 0.0003 | 2 | |
| | 0.0010 | 0.0005 | 11 | |
| | 0.0021 | 0.0010 | 0 | |
| | 0.0042 | 0.0021 | 10 | |
| 0.0008 | 0.0021 | 0.0010 | 65 | 36 |
| 0.0016 | 0.0005 | 0.0003 | 79 | 57 |
| 0.0016 | 0.0010 | 0.0005 | 79 | 61 |
| 0.0016 | 0.0021 | 0.0010 | 78 | 56 |
| 0.0016 | 0.0042 | 0.0021 | 82 | 60 |
| 0.0031 | 0.0042 | 0.0021 | 94 | 84 |
| B15.2: *Monographella nivalis*: | | | | |
| 0.0500 | | | 17 | |
| 0.1000 | | | 63 | |
| | 0.0168 | 0.0083 | 27 | |
| 0.0500 | 0.0168 | 0.0083 | 54 | 40 |
| 0.1000 | 0.0168 | 0.0083 | 94 | 73 |
| B15.3: *Rhizoctonia solani*: | | | | |
| 0.0031 | | | 5 | |
| 0.0063 | | | 0 | |
| 0.0125 | | | 0 | |
| 0.0250 | | | 0 | |
| 0.0500 | | | 9 | |

TABLE B15-continued

The abbreviations are defined as follows:
1.001 = compound No. 1.001
IZM = isopyrazam
PYS: pyraclostrobin

| Solution of 1.001 | Solution of IZM + PYS (2:1) | | observed | expected action |
|---|---|---|---|---|
| ppm | ppm | ppm | % activity | (colby) |
|  | 0.0084 | 0.0041 | 11 |  |
|  | 0.0168 | 0.0083 | 58 |  |
| 0.0031 | 0.0084 | 0.0041 | 37 | 15 |
| 0.0063 | 0.0084 | 0.0041 | 49 | 11 |
| 0.0063 | 0.0168 | 0.0083 | 72 | 58 |
| 0.0125 | 0.0084 | 0.0041 | 43 | 11 |
| 0.0125 | 0.0168 | 0.0083 | 87 | 58 |
| 0.0250 | 0.0084 | 0.0041 | 50 | 11 |
| 0.0250 | 0.0168 | 0.0083 | 72 | 58 |
| 0.0500 | 0.0084 | 0.0041 | 40 | 19 |
| 0.0500 | 0.0168 | 0.0083 | 77 | 62 |

TABLE B16

The abbreviations are defined as follows:
1.001 = compound No. 1.001
IZM = isopyrazam
TFS: trifloxystrobin

| Solution of 1.001 | Solution of IZM + TFS (2:1) | | observed | expected action |
|---|---|---|---|---|
| ppm | ppm | ppm | % activity | (colby) |
| B16.1: *Gaeumannomyces graminis*: | | | | |
| 0.2000 |  |  | 16 |  |
|  | 0.0670 | 0.0330 | 14 |  |
|  | 0.1340 | 0.0660 | 14 |  |
| 0.2000 | 0.0670 | 0.0330 | 75 | 28 |
| 0.2000 | 0.1340 | 0.0660 | 85 | 60 |
| B16.2: *Alternaria solani*: | | | | |
| 0.0008 |  |  | 40 |  |
|  | 0.0005 | 0.0003 | 0 |  |
|  | 0.0010 | 0.0005 | 0 |  |
|  | 0.0021 | 0.0010 | 12 |  |
| 0.0008 | 0.0005 | 0.0003 | 50 | 40 |
| 0.0008 | 0.0010 | 0.0005 | 52 | 40 |
| 0.0008 | 0.0021 | 0.0010 | 60 | 47 |
| B16.3: *Fusarium culmorum*: | | | | |
| 0.0250 |  |  | 26 |  |
| 0.0500 |  |  | 46 |  |
| 0.1000 |  |  | 50 |  |
| 0.2000 |  |  | 56 |  |
|  | 0.0084 | 0.0041 | 6 |  |
|  | 0.0335 | 0.0165 | 9 |  |
|  | 0.0670 | 0.0330 | 4 |  |
|  | 0.1340 | 0.0660 | 4 |  |
|  | 0.1340 | 0.0660 | 2 |  |
| 0.0250 | 0.0084 | 0.0041 | 41 | 30 |
| 0.0250 | 0.0335 | 0.0165 | 46 | 32 |
| 0.0250 | 0.0670 | 0.0330 | 68 | 28 |
| 0.0500 | 0.0335 | 0.0165 | 58 | 51 |
| 0.0500 | 0.0670 | 0.0330 | 70 | 48 |
| 0.0500 | 0.1340 | 0.0660 | 78 | 47 |
| 0.1000 | 0.0670 | 0.0330 | 62 | 52 |
| 0.1000 | 0.1340 | 0.0660 | 77 | 51 |
| 0.2000 | 0.0335 | 0.0165 | 67 | 60 |
| 0.2000 | 0.0670 | 0.0330 | 66 | 57 |
| 0.2000 | 0.1340 | 0.0660 | 75 | 57 |
| B16.4: *Monographella nivalis*: | | | | |
| 0.0004 |  |  | 2 |  |
|  | 0.0010 | 0.0005 | 42 |  |
| 0.0004 | 0.0010 | 0.0005 | 64 | 44 |

TABLE B16-continued

The abbreviations are defined as follows:
1.001 = compound No. 1.001
IZM = isopyrazam
TFS: trifloxystrobin

| Solution of 1.001 | Solution of IZM + TFS (2:1) | | observed | expected action |
|---|---|---|---|---|
| ppm | ppm | ppm | % activity | (colby) |
| B16.5: *Rhizoctonia solani*: | | | | |
| 0.0063 |  |  | 0 |  |
| 0.0125 |  |  | 0 |  |
| 0.0250 |  |  | 0 |  |
| 0.0500 |  |  | 11 |  |
| 0.1000 |  |  | 0 |  |
|  | 0.0084 | 0.0041 | 0 |  |
|  | 0.0168 | 0.0083 | 3 |  |
| 0.0063 | 0.0168 | 0.0083 | 88 | 3 |
| 0.0125 | 0.0084 | 0.0041 | 35 | 0 |
| 0.0250 | 0.0168 | 0.0083 | 74 | 3 |
| 0.0500 | 0.0168 | 0.0083 | 45 | 14 |
| 0.1000 | 0.0168 | 0.0083 | 64 | 3 |

TABLE B17

The abbreviations are defined as follows:
1.001 = compound No. 1.001
IZM = isopyrazam
FDL: fludioxonil

| Solution of 1.001 | Solution of IZM + FDL (1:2) | | observed | expected action |
|---|---|---|---|---|
| ppm | ppm | ppm | % activity | (colby) |
| B17.1: *Alternaria solani* | | | | |
| 0.0008 |  |  | 25 |  |
| 0.0016 |  |  | 57 |  |
|  | 0.0001 | 0.0003 | 0 |  |
|  | 0.0003 | 0.0005 | 9 |  |
|  | 0.0010 | 0.0021 | 1 |  |
|  | 0.0021 | 0.0042 | 0 |  |
| 0.0008 | 0.0001 | 0.0003 | 49 | 25 |
| 0.0008 | 0.0003 | 0.0005 | 42 | 32 |
| 0.0008 | 0.0010 | 0.0021 | 44 | 26 |
| 0.0016 | 0.0001 | 0.0003 | 79 | 57 |
| 0.0016 | 0.0010 | 0.0021 | 78 | 57 |
| 0.0016 | 0.0021 | 0.0042 | 76 | 57 |
| B17.2: *Fusarium culmorum*: | | | | |
| 0.0063 |  |  | 9 |  |
| 0.0125 |  |  | 16 |  |
| 0.0250 |  |  | 27 |  |
| 0.0500 |  |  | 46 |  |
| 0.2000 |  |  | 54 |  |
|  | 0.0041 | 0.0084 | 3 |  |
|  | 0.0083 | 0.0168 | 6 |  |
|  | 0.0165 | 0.0335 | 0 |  |
|  | 0.0330 | 0.0670 | 2 |  |
|  | 0.0660 | 0.1340 | 2 |  |
|  | 0.0660 | 0.1340 | 48 |  |
| 0.0063 | 0.0083 | 0.0168 | 48 | 15 |
| 0.0125 | 0.0165 | 0.0335 | 28 | 16 |
| 0.0250 | 0.0165 | 0.0335 | 96 | 27 |
| 0.0250 | 0.0330 | 0.0670 | 60 | 28 |
| 0.0500 | 0.0041 | 0.0084 | 55 | 48 |
| 0.0500 | 0.0330 | 0.0670 | 79 | 47 |
| 0.0500 | 0.0660 | 0.1340 | 100 | 72 |
| 0.2000 | 0.0660 | 0.1340 | 100 | 76 |
| B17.3: *Monographella nivalis*: | | | | |
| 0.1000 |  |  | 73 |  |
|  | 0.0083 | 0.0168 | 0 |  |
| 0.1000 | 0.0083 | 0.0168 | 80 | 73 |

TABLE B17-continued

The abbreviations are defined as follows:
1.001 = compound No. 1.001
IZM = isopyrazam
FDL: fludioxonil

| Solution of 1.001 | Solution of IZM + FDL (1:2) | | observed | expected action |
|---|---|---|---|---|
| ppm | ppm | ppm | % activity | (colby) |

B17.4: *Rhizoctonia solani*:

| | | | | |
|---|---|---|---|---|
| 0.0250 | | | 0 | |
| 0.0500 | | | 6 | |
| 0.1000 | | | 0 | |
| | 0.0330 | 0.0670 | 81 | |
| 0.0250 | 0.0330 | 0.0670 | 96 | 81 |
| 0.0500 | 0.0330 | 0.0670 | 96 | 82 |
| 0.1000 | 0.0330 | 0.0670 | 96 | 81 |

TABLE B18

The abbreviations are defined as follows:
1.001 = compound No. 1.001
IZM = isopyrazam
CPL: cyprodinil

| Solution of 1.001 | Solution of IZM + CPL (1:2) | | observed | expected action |
|---|---|---|---|---|
| ppm | ppm | ppm | % activity | (colby) |

B18.1: *Alternaria solani*

| | | | | |
|---|---|---|---|---|
| 0.0016 | | | 60 | |
| | 0.0001 | 0.0003 | 12 | |
| | 0.0003 | 0.0005 | 1 | |
| | 0.0010 | 0.0021 | 1 | |
| | 0.0021 | 0.0042 | 8 | |
| 0.0016 | 0.0001 | 0.0003 | 73 | 65 |
| 0.0016 | 0.0003 | 0.0005 | 67 | 61 |
| 0.0016 | 0.0010 | 0.0021 | 68 | 60 |
| 0.0016 | 0.0021 | 0.0042 | 72 | 63 |

B18.2: *Monographella nivalis*:

| | | | | |
|---|---|---|---|---|
| 0.0031 | | | 0 | |
| 0.0063 | | | 0 | |
| | 0.0041 | 0.0084 | 24 | |
| 0.0031 | 0.0041 | 0.0084 | 78 | 24 |
| 0.0063 | 0.0041 | 0.0084 | 51 | 24 |

B18.3: *Rhizoctonia solani*:

| | | | | |
|---|---|---|---|---|
| 0.0125 | | | 20 | |
| 0.0250 | | | 0 | |
| 0.0500 | | | 0 | |
| | 0.0165 | 0.0335 | 47 | |
| 0.0125 | 0.0165 | 0.0335 | 77 | 58 |
| 0.0250 | 0.0165 | 0.0335 | 71 | 47 |
| 0.0500 | 0.0165 | 0.0335 | 54 | 47 |

B18.4: *Septoria tritici*:

| | | | | |
|---|---|---|---|---|
| 0.0016 | | | 62 | |
| | 0.0001 | 0.0003 | 0 | |
| 0.0016 | 0.0001 | 0.0003 | 69 | 62 |

TABLE B19

The abbreviations are defined as follows:
1.001 = compound No. 1.001
IZM = isopyrazam
FLN: fluazinam

| Solution of 1.001 | Solution of IZM + FLN (1:3) | | observed | expected action |
|---|---|---|---|---|
| ppm | ppm | ppm | % activity | (colby) |

B19.1: *Gaeumannomyces graminis*:

| | | | | |
|---|---|---|---|---|
| 0.0500 | | | 0 | |
| 0.1000 | | | 1 | |
| 0.2000 | | | 0 | |
| | 0.0500 | 0.1500 | 76 | |
| | 0.0500 | 0.1500 | 30 | |
| 0.0500 | 0.0500 | 0.1500 | 95 | 30 |
| 0.1000 | 0.0500 | 0.1500 | 83 | 31 |
| 0.2000 | 0.0500 | 0.1500 | 90 | 30 |

B19.2: *Alternaria solani*:

| | | | | |
|---|---|---|---|---|
| 0.0004 | | | 11 | |
| 0.0008 | | | 29 | |
| 0.0016 | | | 65 | |
| | 0.0001 | 0.0003 | 5 | |
| | 0.0002 | 0.0006 | 0 | |
| | 0.0004 | 0.0012 | 16 | |
| | 0.0008 | 0.0023 | 16 | |
| | 0.0016 | 0.0047 | 10 | |
| 0.0004 | 0.0001 | 0.0003 | 28 | 15 |
| 0.0008 | 0.0001 | 0.0003 | 47 | 33 |
| 0.0008 | 0.0004 | 0.0012 | 46 | 40 |
| 0.0008 | 0.0008 | 0.0023 | 46 | 40 |
| 0.0016 | 0.0002 | 0.0006 | 72 | 65 |
| 0.0016 | 0.0016 | 0.0047 | 78 | 69 |

B19.3: *Monographella nivalis*:

| | | | | |
|---|---|---|---|---|
| 0.0250 | | | 3 | |
| 0.0500 | | | 12 | |
| 0.1000 | | | 63 | |
| 0.2000 | | | 90 | |
| | 0.0063 | 0.0188 | 3 | |
| | 0.0250 | 0.0750 | 8 | |
| 0.0250 | 0.0250 | 0.0750 | 95 | 10 |
| 0.0500 | 0.0250 | 0.0750 | 55 | 19 |
| 0.1000 | 0.0063 | 0.0188 | 80 | 65 |
| 0.1000 | 0.0250 | 0.0750 | 92 | 66 |
| 0.2000 | 0.0250 | 0.0750 | 100 | 90 |

TABLE B20

The abbreviations are defined as follows:
1.001 = compound No. 1.001
DFZ = difenoconazole
AZO: azoxystrobin

| Solution of 1.001 | Solution of DFZ + AZO (1:1) | | observed | expected action |
|---|---|---|---|---|
| ppm | ppm | ppm | % activity | (colby) |

B20.1: *Gaeumannomyces graminis*:

| | | | | |
|---|---|---|---|---|
| 0.0125 | | | 0 | |
| 0.0250 | | | 0 | |
| 0.0500 | | | 0 | |
| 0.2000 | | | 0 | |
| | 0.0125 | 0.0125 | 54 | |
| | 0.0250 | 0.0250 | 42 | |
| 0.0125 | 0.0125 | 0.0125 | 60 | 54 |
| 0.0125 | 0.0250 | 0.0250 | 72 | 42 |
| 0.0250 | 0.0250 | 0.0250 | 76 | 42 |
| 0.0500 | 0.0250 | 0.0250 | 79 | 42 |
| 0.2000 | 0.0250 | 0.0250 | 63 | 42 |

TABLE B20-continued

The abbreviations are defined as follows:
1.001 = compound No. 1.001
DFZ = difenoconazole
AZO: azoxystrobin

| Solution of 1.001 | Solution of DFZ + AZO (1:1) | | observed | expected action |
|---|---|---|---|---|
| ppm | ppm | ppm | % activity | (colby) |

B20.2: *Monographella nivalis*:

| | | | | |
|---|---|---|---|---|
| 0.0500 | | | 6 | |
| | 0.0063 | 0.0063 | 39 | |
| 0.0500 | 0.0063 | 0.0063 | 79 | 42 |

B20.3: *Rhizoctonia solani*:

| | | | | |
|---|---|---|---|---|
| 0.0500 | | | 0 | |
| | 0.0500 | 0.0500 | 33 | |
| 0.0500 | 0.0500 | 0.0500 | 52 | 33 |

B20.4: *Septoria tritici*:

| | | | | |
|---|---|---|---|---|
| 0.0016 | | | 35 | |
| | 0.0004 | 0.0004 | 5 | |
| 0.0016 | 0.0004 | 0.0004 | 47 | 38 |

TABLE B21

The abbreviations are defined as follows:
1.001 = compound No. 1.001
DFZ = difenoconazole
PTC = prothioconazole
B21.1: *Rhizoctonia solani*:

| Solution of 1.001 | Solution of DFZ + PTC (1:1) | | observed | expected action |
|---|---|---|---|---|
| ppm | ppm | ppm | % activity | (colby) |
| 0.0500 | | | 0 | |
| | 0.1000 | 0.1000 | 15 | |
| 0.0500 | 0.1000 | 0.1000 | 52 | 15 |

TABLE B22

The abbreviations are defined as follows:
1.001 = compound No. 1.001
DFZ = difenoconazole
TCZ = tebuconazole
B22.1: *Monographella nivalis*:

| Solution of 1.001 | Solution of DFZ + TCZ (1:1) | | observed | expected action |
|---|---|---|---|---|
| ppm | ppm | ppm | % activity | (colby) |
| 0.1000 | | | 46 | |
| | 0.0125 | 0.0125 | 1 | |
| 0.1000 | 0.0125 | 0.0125 | 59 | 46 |

TABLE B23

The abbreviations are defined as follows:
1.001 = compound No. 1.001
DFZ = difenoconazole
PYS = pyraclostrobin
B23.1: *Monographella nivalis*:

| Solution of 1.001 | Solution of DFZ + PYS (2:1) | | observed % | expected action |
|---|---|---|---|---|
| ppm | ppm | ppm | activity | (colby) |
| 0.0250 | | | 0 | |
| 0.0500 | | | 6 | |
| | 0.0670 | 0.0330 | 58 | |
| 0.0250 | 0.0670 | 0.0330 | 85 | 58 |
| 0.0500 | 0.0670 | 0.0330 | 87 | 61 |

TABLE B24

The abbreviations are defined as follows:
1.001 = compound No. 1.001
DFZ = difenoconazole
TFS = trifloxystrobin

| Solution of 1.001 | Solution of DFZ + TFS (2:1) | | observed | expected action |
|---|---|---|---|---|
| ppm | ppm | ppm | % activity | (colby) |

B24.1: *Alternaria solani*

| | | | | |
|---|---|---|---|---|
| 0.0016 | | | 40 | |
| | 0.0003 | 0.0001 | 0 | |
| 0.0016 | 0.0003 | 0.0001 | 66 | 40 |

B24.2: *Monographella nivalis*:

| | | | | |
|---|---|---|---|---|
| 0.0008 | | | 0 | |
| 0.0016 | | | 0 | |
| 0.0031 | | | 0 | |
| 0.0063 | | | 0 | |
| | 0.0010 | 0.0005 | 15 | |
| | 0.0021 | 0.0010 | 49 | |
| | 0.0042 | 0.0021 | 79 | |
| 0.0008 | 0.0010 | 0.0005 | 27 | 15 |
| 0.0016 | 0.0021 | 0.0010 | 64 | 49 |
| 0.0016 | 0.0042 | 0.0021 | 92 | 79 |
| 0.0031 | 0.0042 | 0.0021 | 90 | 79 |
| 0.0063 | 0.0042 | 0.0021 | 94 | 79 |

B24.3: *Botrytis cinerea*:

| | | | | |
|---|---|---|---|---|
| 0.0063 | | | 69 | |
| 0.0125 | | | 83 | |
| | 0.0168 | 0.0083 | 24 | |
| 0.0063 | 0.0168 | 0.0083 | 85 | 77 |
| 0.0125 | 0.0168 | 0.0083 | 98 | 87 |

TABLE B25

The abbreviations are defined as follows:
1.001 = compound No. 1.001
DFZ = difenoconazole
FDL = Fludioxonil

| Solution of 1.001 | Solution of DFZ + FDL (1:2) | | observed % | expected action |
|---|---|---|---|---|
| ppm | ppm | ppm | activity | (colby) |

B25.1: *Fusarium culmorum*

| | | | | |
|---|---|---|---|---|
| 0.0250 | | | 27 | |
| 0.0500 | | | 50 | |
| | 0.0165 | 0.0335 | 8 | |
| | 0.0330 | 0.0670 | 10 | |
| | 0.0660 | 0.1340 | 75 | |

TABLE B25-continued

The abbreviations are defined as follows:
1.001 = compound No. 1.001
DFZ = difenoconazole
FDL = Fludioxonil

| Solution of 1.001 | Solution of DFZ + FDL (1:2) | | observed % activity | expected action (colby) |
|---|---|---|---|---|
| ppm | ppm | ppm | | |
| 0.0250 | 0.0165 | 0.0335 | 51 | 33 |
| 0.0500 | 0.0330 | 0.0670 | 88 | 55 |
| 0.0500 | 0.0660 | 0.1340 | 99 | 87 |

B25.2. *Botrytis cinera*

| Solution of 1.001 | Solution of DFZ + FDL (1:2) | | observed % activity | expected action (colby) |
|---|---|---|---|---|
| 0.0031 | | | 54 | |
| 0.0063 | | | 69 | |
| 0.0125 | | | 84 | |
| | 0.0041 | 0.0084 | 11 | |
| | 0.0083 | 0.0168 | 22 | |
| 0.0031 | 0.0041 | 0.0084 | 65 | 59 |
| 0.0063 | 0.0041 | 0.0084 | 91 | 72 |
| 0.0063 | 0.0083 | 0.0168 | 100 | 76 |
| 0.0125 | 0.0041 | 0.0084 | 96 | 86 |
| 0.0125 | 0.0083 | 0.0168 | 100 | 88 |

TABLE B26

The abbreviations are defined as follows:
1.001 = compound No. 1.001
DFZ = difenoconazole
CPL = Cyprodinil

| Solution of 1.001 | Solution of DFZ + CPL (1:2) | | observed % activity | expected action (colby) |
|---|---|---|---|---|
| ppm | ppm | ppm | | |

B26.1: *Alternaria solani*

| Solution of 1.001 | Solution of DFZ + CPL (1:2) | | observed % activity | expected action (colby) |
|---|---|---|---|---|
| 0.0016 | | | 57 | |
| | 0.0001 | 0.0003 | 0 | |
| 0.0016 | 0.0001 | 0.0003 | 67 | 57 |

B26.2: *Fusarium culmorum*

| Solution of 1.001 | Solution of DFZ + CPL (1:2) | | observed % activity | expected action (colby) |
|---|---|---|---|---|
| 0.0250 | | | 29 | |
| | 0.0021 | 0.0042 | 4 | |
| 0.0250 | 0.0021 | 0.0042 | 47 | 32 |

TABLE B27

The abbreviations are defined as follows:
1.001 = compound No. 1.001
DFZ = difenoconazole
FLN = Fluazinam

| Solution of 1.001 | Solution of DFZ + FLN (1:3) | | observed % activity | expected action (colby) |
|---|---|---|---|---|
| ppm | ppm | ppm | | |

B27.1: *Fusarium culmorum*

| Solution of 1.001 | Solution of DFZ + FLN (1:3) | | observed % activity | expected action (colby) |
|---|---|---|---|---|
| 0.0250 | | | 27 | |
| 0.0500 | | | 49 | |
| | 0.0016 | 0.0047 | 6 | |
| | 0.0031 | 0.0094 | 4 | |
| 0.0250 | 0.0016 | 0.0047 | 41 | 32 |
| 0.0500 | 0.0031 | 0.0094 | 57 | 51 |

B27.2: *Monographella nivalis*

| Solution of 1.001 | Solution of DFZ + FLN (1:3) | | observed % activity | expected action (colby) |
|---|---|---|---|---|
| 0.0500 | | | 6 | |
| 0.1000 | | | 27 | |

TABLE B27-continued

The abbreviations are defined as follows:
1.001 = compound No. 1.001
DFZ = difenoconazole
FLN = Fluazinam

| Solution of 1.001 | Solution of DFZ + FLN (1:3) | | observed % activity | expected action (colby) |
|---|---|---|---|---|
| ppm | ppm | ppm | | |
| 0.2000 | | | 87 | |
| | 0.0500 | 0.1500 | 0 | |
| 0.0500 | 0.0500 | 0.1500 | 78 | 6 |
| 0.1000 | 0.0500 | 0.1500 | 83 | 27 |
| 0.2000 | 0.0500 | 0.1500 | 97 | 87 |

B27.3: *Botrytis cinerea*

| Solution of 1.001 | Solution of DFZ + FLN (1:3) | | observed % activity | expected action (colby) |
|---|---|---|---|---|
| 0.0016 | | | 49 | |
| 0.0031 | | | 57 | |
| 0.0063 | | | 63 | |
| 0.0125 | | | 89 | |
| | 0.0004 | 0.0012 | 3 | |
| | 0.0016 | 0.0047 | 2 | |
| | 0.0031 | 0.0094 | 2 | |
| | 0.0063 | 0.0188 | 5 | |
| | 0.0125 | 0.0375 | 6 | |
| 0.0016 | 0.0016 | 0.0047 | 74 | 50 |
| 0.0031 | 0.0031 | 0.0094 | 84 | 58 |
| 0.0063 | 0.0004 | 0.0012 | 74 | 65 |
| 0.0063 | 0.0031 | 0.0094 | 85 | 64 |
| 0.0063 | 0.0063 | 0.0188 | 100 | 65 |
| 0.0125 | 0.0063 | 0.0188 | 99 | 89 |
| 0.0125 | 0.0125 | 0.0375 | 100 | 89 |

TABLE B28

The abbreviations are defined as follows:
1.001 = compound No. 1.001
AZ = azoxystrobin
PTC = Prothioconazole

| Solution of 1.001 | Solution of AZO + PTC (1:1) | | observed % activity | expected action (colby) |
|---|---|---|---|---|
| ppm | ppm | ppm | | |

B28.1: *Gäumannomyces graminis*

| Solution of 1.001 | Solution of AZO + PTC (1:1) | | observed % activity | expected action (colby) |
|---|---|---|---|---|
| 0.0031 | | | 0 | |
| 0.0125 | | | 0 | |
| 0.0250 | | | 0 | |
| 0.0500 | | | 0 | |
| 0.1000 | | | 0 | |
| 0.2000 | | | 0 | |
| | 0.0063 | 0.0063 | 17 | |
| | 0.0250 | 0.0250 | 60 | |
| | 0.0500 | 0.0500 | 66 | |
| | 0.1000 | 0.1000 | 66 | |
| | 0.1000 | 0.1000 | 66 | |
| 0.0031 | 0.0063 | 0.0063 | 40 | 17 |
| 0.0125 | 0.0250 | 0.0250 | 67 | 60 |
| 0.0250 | 0.0063 | 0.0063 | 41 | 17 |
| 0.0250 | 0.0500 | 0.0500 | 76 | 66 |
| 0.0500 | 0.1000 | 0.1000 | 77 | 66 |
| 0.1000 | 0.0250 | 0.0250 | 71 | 60 |
| 0.1000 | 0.1000 | 0.1000 | 75 | 66 |
| 0.2000 | 0.1000 | 0.1000 | 78 | 66 |

B28.2: *Alternaria solani*

| Solution of 1.001 | Solution of AZO + PTC (1:1) | | observed % activity | expected action (colby) |
|---|---|---|---|---|
| 0.0016 | | | 24 | |
| | 0.0002 | 0.0002 | 5 | |
| | 0.0016 | 0.0016 | 6 | |
| 0.0016 | 0.0002 | 0.0002 | 40 | 28 |
| 0.0016 | 0.0016 | 0.0016 | 44 | 29 |

TABLE B28-continued

The abbreviations are defined as follows:
1.001 = compound No. 1.001
AZ = azoxystrobin
PTC = Prothioconazole

| Solution of 1.001 ppm | Solution of AZO + PTC (1:1) ppm | ppm | observed % activity | expected action (colby) |
|---|---|---|---|---|
| B28.3: *Fusarium culmorum* | | | | |
| 0.0500 | | | 55 | |
| 0.1000 | | | 56 | |
| | 0.1000 | 0.1000 | 55 | |
| 0.0500 | 0.1000 | 0.1000 | 100 | 80 |
| 0.1000 | 0.1000 | 0.1000 | 97 | 80 |
| B28.4: *Monographella nivalis* | | | | |
| 0.0016 | | | 0 | |
| 0.0031 | | | 2 | |
| 0.0125 | | | 2 | |
| 0.0500 | | | 6 | |
| | 0.0031 | 0.0031 | 18 | |
| | 0.0063 | 0.0063 | 63 | |
| 0.0016 | 0.0031 | 0.0031 | 45 | 18 |
| 0.0031 | 0.0063 | 0.0063 | 93 | 64 |
| 0.0125 | 0.0063 | 0.0063 | 73 | 64 |
| 0.0500 | 0.0063 | 0.0063 | 95 | 65 |

TABLE B29

The abbreviations are defined as follows:
1.001 = compound No. 1.001
AZ = azoxystrobin
TCZ = Tebuconazole

| Solution of 1.001 ppm | Solution of AZO + TCZ (1:1) ppm | ppm | observed % activity | expected action (colby) |
|---|---|---|---|---|
| B29.1: *Gäumannomyces graminis* | | | | |
| 0.0250 | | | 2 | |
| 0.0500 | | | 0 | |
| 0.1000 | | | 0 | |
| 0.2000 | | | 0 | |
| | 0.0031 | 0.0031 | 4 | |
| | 0.0250 | 0.0250 | 44 | |
| | 0.0500 | 0.0500 | 69 | |
| 0.0250 | 0.0031 | 0.0031 | 41 | 6 |
| 0.0250 | 0.0250 | 0.0250 | 58 | 45 |
| 0.0500 | 0.0250 | 0.0250 | 66 | 44 |
| 0.0500 | 0.0500 | 0.0500 | 79 | 69 |
| 0.1000 | 0.0500 | 0.0500 | 78 | 69 |
| 0.2000 | 0.0250 | 0.0250 | 53 | 44 |
| B29.2: *Monographella nivalis* | | | | |
| 0.0250 | | | 0 | |
| | 0.0063 | 0.0063 | 62 | |
| 0.0250 | 0.0063 | 0.0063 | 73 | 62 |
| B29.3: *Septoria tritici* | | | | |
| 0.0008 | | | 17 | |
| 0.0016 | | | 40 | |
| 0.0031 | | | 88 | |
| | 0.0016 | 0.0016 | 0 | |
| | 0.0031 | 0.0031 | 12 | |
| | 0.0063 | 0.0063 | 3 | |
| 0.0008 | 0.0016 | 0.0016 | 22 | 17 |
| 0.0016 | 0.0031 | 0.0031 | 68 | 47 |
| 0.0031 | 0.0063 | 0.0063 | 95 | 89 |

TABLE B30

The abbreviations are defined as follows:
1.001 = compound No. 1.001
AZ = azoxystrobin
PYS = Pyraclostrobin

| Solution of 1.001 ppm | Solution of AZO + PYS (2:1) ppm | ppm | observed % activity | expected action (colby) |
|---|---|---|---|---|
| B30.1: *Gäumannomyces graminis* | | | | |
| 0.0031 | | | 7 | |
| 0.0125 | | | 0 | |
| 0.0250 | | | 0 | |
| 0.0500 | | | 1 | |
| 0.1000 | | | 4 | |
| 0.2000 | | | 0 | |
| | 0.0084 | 0.0041 | 40 | |
| | 0.0168 | 0.0083 | 51 | |
| | 0.0335 | 0.0165 | 55 | |
| | 0.0670 | 0.0330 | 53 | |
| | 0.1340 | 0.0660 | 53 | |
| | 0.1340 | 0.0660 | 62 | |
| 0.0031 | 0.0084 | 0.0041 | 52 | 45 |
| 0.0125 | 0.0168 | 0.0083 | 60 | 51 |
| 0.0125 | 0.0335 | 0.0165 | 66 | 55 |
| 0.0250 | 0.0084 | 0.0041 | 53 | 40 |
| 0.0250 | 0.0335 | 0.0165 | 72 | 55 |
| 0.0250 | 0.0670 | 0.0330 | 80 | 53 |
| 0.0500 | 0.0335 | 0.0165 | 64 | 56 |
| 0.0500 | 0.0670 | 0.0330 | 66 | 54 |
| 0.1000 | 0.0335 | 0.0165 | 72 | 57 |
| 0.1000 | 0.0670 | 0.0330 | 69 | 55 |
| 0.1000 | 0.1340 | 0.0660 | 75 | 63 |
| 0.2000 | 0.0335 | 0.0165 | 64 | 55 |
| 0.2000 | 0.0670 | 0.0330 | 61 | 53 |
| 0.2000 | 0.1340 | 0.0660 | 68 | 62 |
| B30.2: *Alternaria solani* | | | | |
| 0.0016 | | | 31 | |
| | 0.0021 | 0.0010 | 11 | |
| | 0.0042 | 0.0021 | 7 | |
| 0.0016 | 0.0021 | 0.0010 | 58 | 38 |
| 0.0016 | 0.0042 | 0.0021 | 58 | 36 |
| B30.3: *Fusarium culmorum* | | | | |
| 0.0250 | | | 28 | |
| 0.0500 | | | 55 | |
| 0.1000 | | | 56 | |
| | 0.0670 | 0.0330 | 0 | |
| | 0.1340 | 0.0660 | 8 | |
| 0.0250 | 0.0670 | 0.0330 | 43 | 28 |
| 0.0500 | 0.0670 | 0.0330 | 61 | 55 |
| 0.0500 | 0.1340 | 0.0660 | 66 | 58 |
| 0.1000 | 0.1340 | 0.0660 | 69 | 60 |
| B30.4: *Monographella nivalis* | | | | |
| 0.0016 | | | 0 | |
| 0.0031 | | | 0 | |
| | 0.0021 | 0.0010 | 31 | |
| | 0.0042 | 0.0021 | 52 | |
| 0.0016 | 0.0021 | 0.0010 | 61 | 31 |
| 0.0016 | 0.0042 | 0.0021 | 61 | 52 |
| 0.0031 | 0.0042 | 0.0021 | 82 | 52 |

TABLE B31

The abbreviations are defined as follows:
1.001 = compound No. 1.001
AZ = azoxystrobin
TFS = Trifloxystrobin

| Solution of 1.001 ppm | Solution of AZO + TFS (2:1) ppm | | observed % activity | expected action (colby) |
|---|---|---|---|---|
| \multicolumn{5}{c}{B31.1: Gäumannomyces graminis} | | | | |
| 0.0063 | | | 0 | |
| 0.0125 | | | 0 | |
| 0.0250 | | | 4 | |
| 0.0500 | | | 0 | |
| 0.2000 | | | 3 | |
| | 0.0084 | 0.0041 | 41 | |
| | 0.0168 | 0.0083 | 61 | |
| | 0.0335 | 0.0165 | 44 | |
| 0.0063 | 0.0084 | 0.0041 | 51 | 41 |
| 0.0063 | 0.0168 | 0.0083 | 67 | 61 |
| 0.0125 | 0.0084 | 0.0041 | 56 | 41 |
| 0.0125 | 0.0168 | 0.0083 | 69 | 61 |
| 0.0125 | 0.0335 | 0.0165 | 76 | 44 |
| 0.0250 | 0.0335 | 0.0165 | 75 | 46 |
| 0.0500 | 0.0335 | 0.0165 | 53 | 44 |
| 0.2000 | 0.0335 | 0.0165 | 72 | 46 |
| \multicolumn{5}{c}{B31.2: Alternaria solani} | | | | |
| 0.0008 | | | 1 | |
| | 0.0003 | 0.0001 | 0 | |
| | 0.0005 | 0.0003 | 5 | |
| | 0.0010 | 0.0005 | 0 | |
| 0.0008 | 0.0003 | 0.0001 | 39 | 1 |
| 0.0008 | 0.0005 | 0.0003 | 34 | 5 |
| 0.0008 | 0.0010 | 0.0005 | 42 | 1 |
| \multicolumn{5}{c}{B31.3: Fusarium culmorum} | | | | |
| 0.0125 | | | 11 | |
| 0.0250 | | | 29 | |
| 0.0500 | | | 52 | |
| 0.1000 | | | 52 | |
| 0.2000 | | | 59 | |
| | 0.0335 | 0.0165 | 11 | |
| | 0.0670 | 0.0330 | 7 | |
| | 0.1340 | 0.0660 | 7 | |
| 0.0125 | 0.0335 | 0.0165 | 42 | 20 |
| 0.0250 | 0.0335 | 0.0165 | 58 | 36 |
| 0.0250 | 0.0670 | 0.0330 | 73 | 34 |
| 0.0500 | 0.0335 | 0.0165 | 64 | 57 |
| 0.0500 | 0.0670 | 0.0330 | 74 | 56 |
| 0.0500 | 0.1340 | 0.0660 | 77 | 56 |
| 0.1000 | 0.0670 | 0.0330 | 72 | 55 |
| 0.1000 | 0.1340 | 0.0660 | 78 | 55 |
| 0.2000 | 0.0670 | 0.0330 | 71 | 62 |
| 0.2000 | 0.1340 | 0.0660 | 75 | 62 |
| \multicolumn{5}{c}{B31.4: Monographella nivalis} | | | | |
| 0.0004 | | | 0 | |
| 0.0008 | | | 0 | |
| | 0.0010 | 0.0005 | 37 | |
| 0.0004 | 0.0010 | 0.0005 | 64 | 37 |
| 0.0008 | 0.0010 | 0.0005 | 55 | 37 |
| \multicolumn{5}{c}{B31.5: Septoria tritici} | | | | |
| 0.0016 | | | 44 | |
| | 0.0042 | 0.0021 | 65 | |
| 0.0016 | 0.0042 | 0.0021 | 95 | 80 |
| \multicolumn{5}{c}{B31.6: Botrytis cinerea} | | | | |
| 0.0008 | | | 29 | |
| 0.0016 | | | 51 | |
| | 0.0021 | 0.0010 | 18 | |
| | 0.0042 | 0.0021 | 34 | |
| 0.0008 | 0.0021 | 0.0010 | 65 | 42 |
| 0.0016 | 0.0042 | 0.0021 | 76 | 68 |

TABLE B32

The abbreviations are defined as follows:
1.001 = compound No. 1.001
AZ = azoxystrobin
FDL = Fludioxonil

| Solution of 1.001 ppm | Solution of AZO + FDL (1:2) ppm | | observed % activity | expected action (colby) |
|---|---|---|---|---|
| \multicolumn{5}{c}{B32.1: Gäumannomyces graminis} | | | | |
| 0.0063 | | | 10 | |
| 0.0125 | | | 1 | |
| 0.0250 | | | 6 | |
| 0.0500 | | | 0 | |
| 0.1000 | | | 0 | |
| 0.2000 | | | 0 | |
| | 0.0041 | 0.0084 | 11 | |
| | 0.0083 | 0.0168 | 34 | |
| | 0.0165 | 0.0335 | 55 | |
| | 0.0660 | 0.1340 | 63 | |
| 0.0063 | 0.0041 | 0.0084 | 35 | 20 |
| 0.0125 | 0.0041 | 0.0084 | 38 | 11 |
| 0.0125 | 0.0083 | 0.0168 | 63 | 35 |
| 0.0250 | 0.0083 | 0.0168 | 48 | 38 |
| 0.0500 | 0.0660 | 0.1340 | 70 | 63 |
| 0.1000 | 0.0083 | 0.0168 | 49 | 34 |
| 0.1000 | 0.0165 | 0.0335 | 63 | 55 |
| 0.2000 | 0.0165 | 0.0335 | 66 | 55 |
| \multicolumn{5}{c}{B32.2: Alternaria solani} | | | | |
| 0.0016 | | | 38 | |
| 0.0031 | | | 69 | |
| | 0.0003 | 0.0005 | 0 | |
| | 0.0005 | 0.0010 | 0 | |
| | 0.0010 | 0.0021 | 1 | |
| | 0.0021 | 0.0042 | 0 | |
| 0.0016 | 0.0003 | 0.0005 | 69 | 38 |
| 0.0016 | 0.0005 | 0.0010 | 45 | 38 |
| 0.0016 | 0.0021 | 0.0042 | 74 | 38 |
| 0.0031 | 0.0010 | 0.0021 | 77 | 69 |
| \multicolumn{5}{c}{B32.3: Fusarium culmorum} | | | | |
| 0.0250 | | | 24 | |
| 0.0500 | | | 51 | |
| 0.1000 | | | 55 | |
| 0.2000 | | | 57 | |
| | 0.0330 | 0.0670 | 0 | |
| | 0.0660 | 0.1340 | 0 | |
| | 0.0660 | 0.1340 | 10 | |
| 0.0250 | 0.0330 | 0.0670 | 47 | 24 |
| 0.0500 | 0.0330 | 0.0670 | 84 | 51 |
| 0.0500 | 0.0660 | 0.1340 | 83 | 56 |
| 0.1000 | 0.0330 | 0.0670 | 71 | 55 |
| 0.1000 | 0.0660 | 0.1340 | 95 | 59 |
| 0.2000 | 0.0330 | 0.0670 | 65 | 57 |
| 0.2000 | 0.0660 | 0.1340 | 91 | 61 |
| \multicolumn{5}{c}{B32.4: Rhizoctonia solani} | | | | |
| 0.0500 | | | 11 | |
| 0.1000 | | | 10 | |
| | 0.0330 | 0.0670 | 0 | |
| | 0.0660 | 0.1340 | 20 | |
| 0.0500 | 0.0330 | 0.0670 | 58 | 11 |
| 0.0500 | 0.0660 | 0.1340 | 76 | 29 |
| 0.1000 | 0.0660 | 0.1340 | 94 | 28 |
| \multicolumn{5}{c}{B32.5: Botrytis cinerea} | | | | |
| 0.0031 | | | 63 | |
| 0.0063 | | | 85 | |
| | 0.0041 | 0.0084 | 10 | |
| | 0.0083 | 0.0168 | 36 | |
| 0.0031 | 0.0041 | 0.0084 | 79 | 66 |
| 0.0063 | 0.0083 | 0.0168 | 100 | 90 |

TABLE B33

The abbreviations are defined as follows:
1.001 = compound No. 1.001
AZ = azoxystrobin
CPL = Cyprodinil

| Solution of 1.001 ppm | Solution of AZO + CPL (1:2) ppm | ppm | observed % activity | expected action (colby) |
|---|---|---|---|---|
| 0.0125 | | | 0 | |
| 0.0250 | | | 0 | |
| 0.0500 | | | 0 | |
| 0.1000 | | | 0 | |
| 0.2000 | | | 2 | |
| | 0.0083 | 0.0168 | 50 | |
| | 0.0165 | 0.0335 | 43 | |
| | 0.0330 | 0.0670 | 56 | |
| 0.0125 | 0.0083 | 0.0168 | 65 | 50 |
| 0.0125 | 0.0165 | 0.0335 | 81 | 43 |
| 0.0250 | 0.0165 | 0.0335 | 65 | 43 |
| 0.0250 | 0.0330 | 0.0670 | 83 | 56 |
| 0.0500 | 0.0330 | 0.0670 | 73 | 56 |
| 0.1000 | 0.0165 | 0.0335 | 61 | 43 |
| 0.2000 | 0.0330 | 0.0670 | 64 | 57 |

B33.2: *Alternaria solani*

| 0.0008 | | | 9 | |
| 0.0016 | | | 44 | |
| | 0.0001 | 0.0003 | 0 | |
| | 0.0003 | 0.0005 | 3 | |
| 0.0008 | 0.0001 | 0.0003 | 26 | 9 |
| 0.0008 | 0.0003 | 0.0005 | 35 | 11 |
| 0.0016 | 0.0003 | 0.0005 | 53 | 45 |

B33.3: *Monographella nivalis*

| 0.0031 | | | 0 | |
| 0.0063 | | | 0 | |
| 0.0125 | | | 0 | |
| | 0.0041 | 0.0084 | 29 | |
| 0.0031 | 0.0041 | 0.0084 | 61 | 29 |
| 0.0063 | 0.0041 | 0.0084 | 58 | 29 |
| 0.0125 | 0.0041 | 0.0084 | 43 | 29 |

TABLE B34

The abbreviations are defined as follows:
1.001 = compound No. 1.001
AZ = azoxystrobin
FLN = Fluazinam

| Solution of 1.001 ppm | Solution of AZO + FLN (1:3) ppm | ppm | observed % activity | expected action (colby) |
|---|---|---|---|---|

B34.1: *Gäumannomyces graminis*

| 0.0063 | | | 0 | |
| 0.0125 | | | 0 | |
| 0.0250 | | | 4 | |
| 0.0500 | | | 0 | |
| 0.2000 | | | 0 | |
| | 0.0063 | 0.0188 | 20 | |
| | 0.0125 | 0.0375 | 48 | |
| | 0.0250 | 0.0750 | 57 | |
| 0.0063 | 0.0063 | 0.0188 | 55 | 20 |
| 0.0125 | 0.0063 | 0.0188 | 50 | 20 |
| 0.0125 | 0.0125 | 0.0375 | 71 | 48 |
| 0.0250 | 0.0250 | 0.0750 | 77 | 59 |
| 0.0500 | 0.0250 | 0.0750 | 74 | 57 |
| 0.2000 | 0.0250 | 0.0750 | 81 | 57 |

TABLE B34-continued

The abbreviations are defined as follows:
1.001 = compound No. 1.001
AZ = azoxystrobin
FLN = Fluazinam

| Solution of 1.001 ppm | Solution of AZO + FLN (1:3) ppm | ppm | observed % activity | expected action (colby) |
|---|---|---|---|---|

B34.2: *Monographella nivalis*

| 0.0031 | | | 0 | |
| 0.0063 | | | 0 | |
| 0.0125 | | | 0 | |
| 0.0250 | | | 0 | |
| | 0.0031 | 0.0094 | 17 | |
| 0.0031 | 0.0031 | 0.0094 | 98 | 17 |
| 0.0063 | 0.0031 | 0.0094 | 71 | 17 |
| 0.0125 | 0.0031 | 0.0094 | 51 | 17 |
| 0.0250 | 0.0031 | 0.0094 | 42 | 17 |

B34.3: *Septoria tritici*

| 0.0008 | | | 36 | |
| 0.0016 | | | 53 | |
| | 0.0008 | 0.0023 | 2 | |
| | 0.0016 | 0.0047 | 6 | |
| 0.0008 | 0.0008 | 0.0023 | 54 | 37 |
| 0.0016 | 0.0016 | 0.0047 | 75 | 56 |

B34.4: *Botrytis cinerea*

| 0.0031 | | | 73 | |
| | 0.0031 | 0.0094 | 2 | |
| 0.0031 | 0.0031 | 0.0094 | 90 | 74 |

TABLE B35

The abbreviations are defined as follows:
1.001 = compound No. 1.001
PTC = Prothioconazole
TCZ = Tebuconazole

| Solution of 1.001 ppm | Solution of PTC + TCZ 1:1 ppm | ppm | observed % activity | expected action (colby) |
|---|---|---|---|---|

B35.1: *Gäumannomyces graminis*

| 0.0250 | | | 7 | |
| 0.0500 | | | 9 | |
| 0.1000 | | | 17 | |
| | 0.0500 | 0.0500 | 0 | |
| | 0.1000 | 0.1000 | 53 | |
| 0.0250 | 0.0500 | 0.0500 | 57 | 7 |
| 0.0500 | 0.1000 | 0.1000 | 88 | 58 |
| 0.1000 | 0.1000 | 0.1000 | 100 | 61 |

B35.2: *Alternaria solani*

| 0.0016 | | | 7 | |
| 0.0063 | | | 75 | |
| | 0.0031 | 0.0031 | 13 | |
| | 0.0063 | 0.0063 | 6 | |
| 0.0016 | 0.0031 | 0.0031 | 44 | 19 |
| 0.0063 | 0.0031 | 0.0031 | 87 | 78 |
| 0.0063 | 0.0063 | 0.0063 | 89 | 76 |

B35.3: *Fusarium culmorum*

| 0.0125 | | | 7 | |
| 0.0250 | | | 46 | |
| | 0.0250 | 0.0250 | 31 | |
| | 0.0500 | 0.0500 | 40 | |
| 0.0125 | 0.0250 | 0.0250 | 59 | 36 |
| 0.0250 | 0.0500 | 0.0500 | 100 | 67 |

TABLE B35-continued

The abbreviations are defined as follows:
1.001 = compound No. 1.001
PTC = Prothioconazole
TCZ = Tebuconazole

| Solution of 1.001 ppm | Solution of PTC + TCZ 1:1 ppm | | observed % activity | expected action (colby) |
|---|---|---|---|---|
| B35.4: *Monographella nivalis* | | | | |
| 0.0125 | | | 0 | |
| | 0.0250 | 0.0250 | 0 | |
| 0.0125 | 0.0250 | 0.0250 | 91 | 0 |

TABLE B36

| Solution of 1.001 ppm | Solution of PTC + PYS 2:1 ppm | | observed % activity | expected action (colby) |
|---|---|---|---|---|
| B36.1: *Gäumannomyces graminis* | | | | |
| 0.0500 | | | 7 | |
| | 0.1340 | 0.0660 | 41 | |
| 0.0500 | 0.1340 | 0.0660 | 100 | 46 |
| B36.2: *Fusarium culmorum* | | | | |
| 0.0250 | | | 29 | |
| | 0.0042 | 0.0021 | 1 | |
| 0.0250 | 0.0042 | 0.0021 | 46 | 30 |
| B36.3: *Monographella nivalis* | | | | |
| 0.0031 | | | 2 | |
| 0.0063 | | | 0 | |
| | 0.0084 | 0.0041 | 30 | |
| | 0.0168 | 0.0083 | 90 | |
| 0.0031 | 0.0084 | 0.0041 | 51 | 32 |
| 0.0063 | 0.0084 | 0.0041 | 39 | 30 |
| 0.0063 | 0.0168 | 0.0083 | 99 | 90 |

The abbreviations are defined as follows:
1.001 = compound No. 1.001
PTC = Prothioconazole
PYS = Pyraclostrobin

TABLE B37

| Solution of 1.001 ppm | Solution of PTC + TFS 2:1 ppm | | observed % activity | expected action (colby) |
|---|---|---|---|---|
| B37.1 *Fusarium culmorum* | | | | |
| 0.0125 | | | 10 | |
| 0.0250 | | | 27 | |
| | 0.0335 | 0.0165 | 16 | |
| | 0.0670 | 0.0330 | 41 | |
| 0.0125 | 0.0335 | 0.0165 | 39 | 24 |
| 0.0250 | 0.0670 | 0.0330 | 96 | 57 |
| B37.2: *Monographella nivalis* | | | | |
| 0.0004 | | | 0 | |
| | 0.0005 | 0.0003 | 81 | |
| 0.0004 | 0.0005 | 0.0003 | 95 | 81 |

The abbreviations are defined as follows:
1.001 = compound No. 1.001
PTC = Prothioconazole
TFS = Trifloxystrobin

TABLE B38

| Solution of 1.001 ppm | Solution of PTC + FDL 1:2 ppm | | observed % activity | expected action (colby) |
|---|---|---|---|---|
| B38.1: *Alternaria solani* | | | | |
| 0.0008 | | | 4 | |
| 0.0016 | | | 14 | |
| 0.0031 | | | 46 | |
| | 0.0005 | 0.0010 | 0 | |
| | 0.0010 | 0.0021 | 0 | |
| | 0.0021 | 0.0042 | 6 | |
| 0.0008 | 0.0005 | 0.0010 | 27 | 4 |
| 0.0008 | 0.0010 | 0.0021 | 25 | 4 |
| 0.0016 | 0.0021 | 0.0042 | 42 | 18 |
| 0.0031 | 0.0021 | 0.0042 | 75 | 49 |
| B38.2: *Fusarium culmorum* | | | | |
| 0.0125 | | | 9 | |
| 0.0250 | | | 28 | |
| 0.0500 | | | 52 | |
| | 0.0165 | 0.0335 | 9 | |
| | 0.0330 | 0.0670 | 12 | |
| 0.0125 | 0.0165 | 0.0335 | 34 | 17 |
| 0.0250 | 0.0165 | 0.0335 | 44 | 35 |
| 0.0250 | 0.0330 | 0.0670 | 62 | 37 |
| 0.0500 | 0.0330 | 0.0670 | 64 | 57 |
| B38.3: *Botrytis cinerea* | | | | |
| 0.0016 | | | 21 | |
| 0.0031 | | | 42 | |
| 0.0063 | | | 64 | |
| | 0.0021 | 0.0042 | 4 | |
| | 0.0041 | 0.0084 | 1 | |
| | 0.0083 | 0.0168 | 25 | |
| 0.0016 | 0.0021 | 0.0042 | 29 | 24 |
| 0.0031 | 0.0041 | 0.0084 | 69 | 43 |
| 0.0063 | 0.0041 | 0.0084 | 77 | 64 |
| 0.0063 | 0.0083 | 0.0168 | 96 | 73 |

The abbreviations are defined as follows:
1.001 = compound No. 1.001
PTC = Prothioconazole
FDL = Fludioxonil

TABLE B39

| Solution of 1.001 ppm | Solution of PTC + CPL 1:2 ppm | | observed % activity | expected action (colby) |
|---|---|---|---|---|
| B39.1: *Monographella nivalis* | | | | |
| 0.0031 | | | 0 | |
| 0.0063 | | | 0 | |
| 0.0125 | | | 2 | |
| | 0.0041 | 0.0084 | 18 | |
| | 0.0083 | 0.0168 | 68 | |
| 0.0031 | 0.0041 | 0.0084 | 45 | 18 |
| 0.0063 | 0.0041 | 0.0084 | 39 | 18 |
| 0.0063 | 0.0083 | 0.0168 | 86 | 68 |
| 0.0125 | 0.0083 | 0.0168 | 81 | 68 |
| B39.2: *Septoria tritici* | | | | |
| 0.0016 | | | 59 | |
| | 0.0001 | 0.0003 | 3 | |
| 0.0016 | 0.0001 | 0.0003 | 78 | 60 |
| B39.3: *Botrytis cinerea* | | | | |
| 0.0031 | | | 39 | |
| 0.0063 | | | 64 | |
| | 0.0003 | 0.0005 | 0 | |
| | 0.0010 | 0.0021 | 0 | |
| | 0.0021 | 0.0042 | 0 | |
| | 0.0041 | 0.0084 | 0 | |
| 0.0031 | 0.0003 | 0.0005 | 54 | 39 |

TABLE B39-continued

| Solution of 1.001 ppm | Solution of PTC + CPL 1:2 ppm | ppm | observed % activity | expected action (colby) |
|---|---|---|---|---|
| 0.0031 | 0.0010 | 0.0021 | 46 | 39 |
| 0.0031 | 0.0041 | 0.0084 | 68 | 39 |
| 0.0063 | 0.0021 | 0.0042 | 76 | 64 |
| 0.0063 | 0.0041 | 0.0084 | 73 | 64 |

The abbreviations are defined as follows:
1.001 = compound No. 1.001
PTC = Prothioconazole
CPL = Cyprodinil

TABLE B40

| Solution of 1.001 ppm | Solution of PTC + FLN 1:3 ppm | ppm | observed % activity | expected action (colby) |
|---|---|---|---|---|
| B40.1: *Alternaria solani* | | | | |
| 0.0016 | | | 25 | |
| 0.0031 | | | 50 | |
| | 0.0016 | 0.0047 | 5 | |
| | 0.0031 | 0.0094 | 5 | |
| 0.0016 | 0.0016 | 0.0047 | 45 | 29 |
| 0.0031 | 0.0016 | 0.0047 | 62 | 53 |
| 0.0031 | 0.0031 | 0.0094 | 64 | 53 |
| B40.2: *Monographella nivalis* | | | | |
| 0.0031 | | | 2 | |
| 0.0063 | | | 0 | |
| 0.0125 | | | 2 | |
| 0.0250 | | | 3 | |
| 0.0500 | | | 0 | |
| | 0.0031 | 0.0094 | 13 | |
| | 0.0063 | 0.0188 | 38 | |
| 0.0031 | 0.0031 | 0.0094 | 28 | 14 |
| 0.0063 | 0.0063 | 0.0188 | 98 | 38 |
| 0.0125 | 0.0063 | 0.0188 | 84 | 39 |
| 0.0250 | 0.0063 | 0.0188 | 61 | 40 |
| 0.0500 | 0.0063 | 0.0188 | 66 | 38 |
| B40.3: *Septoria tritici* | | | | |
| 0.0016 | | | 60 | |
| 0.0031 | | | 89 | |
| | 0.0001 | 0.0003 | 0 | |
| | 0.0031 | 0.0094 | 0 | |
| 0.0016 | 0.0001 | 0.0003 | 70 | 60 |
| 0.0031 | 0.0031 | 0.0094 | 99 | 89 |
| B40.4: *Botrytis cinerea* | | | | |
| 0.0016 | | | 26 | |
| 0.0031 | | | 48 | |
| 0.0063 | | | 66 | |
| 0.0125 | | | 88 | |
| | 0.0016 | 0.0047 | 6 | |
| | 0.0031 | 0.0094 | 9 | |
| | 0.0063 | 0.0188 | 20 | |
| 0.0016 | 0.0016 | 0.0047 | 60 | 30 |
| 0.0031 | 0.0016 | 0.0047 | 57 | 51 |
| 0.0031 | 0.0031 | 0.0094 | 96 | 52 |
| 0.0063 | 0.0031 | 0.0094 | 91 | 69 |
| 0.0063 | 0.0063 | 0.0188 | 100 | 73 |
| 0.0125 | 0.0063 | 0.0188 | 99 | 90 |

The abbreviations are defined as follows:
1.001 = compound No. 1.001
PTC = Prothioconazole
FLN = Fluazinam

TABLE B41

| Solution of 1.001 ppm | Solution of TCZ + PYS 2:1 ppm | ppm | observed % activity | expected action (colby) |
|---|---|---|---|---|
| B41.1: *Alternaria solani* | | | | |
| 0.0016 | | | 49 | |
| 0.0031 | | | 81 | |
| | 0.0042 | 0.0021 | 5 | |
| | 0.0084 | 0.0041 | 17 | |
| 0.0016 | 0.0042 | 0.0021 | 78 | 52 |
| 0.0031 | 0.0084 | 0.0041 | 94 | 84 |
| B41.2: *Monographella nivalis* | | | | |
| 0.0031 | | | 10 | |
| 0.0063 | | | 14 | |
| 0.0125 | | | 4 | |
| 0.0250 | | | 23 | |
| 0.0500 | | | 40 | |
| 0.1000 | | | 67 | |
| | 0.0042 | 0.0021 | 23 | |
| | 0.0084 | 0.0041 | 10 | |
| | 0.0168 | 0.0083 | 32 | |
| 0.0031 | 0.0042 | 0.0021 | 48 | 31 |
| 0.0031 | 0.0084 | 0.0041 | 64 | 19 |
| 0.0063 | 0.0084 | 0.0041 | 100 | 22 |
| 0.0063 | 0.0168 | 0.0083 | 90 | 42 |
| 0.0125 | 0.0168 | 0.0083 | 100 | 35 |
| 0.0250 | 0.0168 | 0.0083 | 66 | 48 |
| 0.0500 | 0.0084 | 0.0041 | 51 | 46 |
| 0.0500 | 0.0168 | 0.0083 | 77 | 59 |
| 0.1000 | 0.0168 | 0.0083 | 96 | 78 |
| B41.3: *Botrytis cinerea* | | | | |
| 0.0008 | | | 33 | |
| 0.0016 | | | 54 | |
| 0.0031 | | | 73 | |
| 0.0063 | | | 88 | |
| | 0.0005 | 0.0003 | 3 | |
| | 0.0021 | 0.0010 | 0 | |
| | 0.0042 | 0.0021 | 0 | |
| | 0.0084 | 0.0041 | 7 | |
| 0.0008 | 0.0021 | 0.0010 | 52 | 33 |
| 0.0016 | 0.0021 | 0.0010 | 78 | 54 |
| 0.0016 | 0.0042 | 0.0021 | 96 | 54 |
| 0.0031 | 0.0005 | 0.0003 | 81 | 74 |
| 0.0031 | 0.0021 | 0.0010 | 80 | 73 |
| 0.0031 | 0.0042 | 0.0021 | 98 | 73 |
| 0.0031 | 0.0084 | 0.0041 | 100 | 75 |
| 0.0063 | 0.0042 | 0.0021 | 97 | 88 |
| 0.0063 | 0.0084 | 0.0041 | 99 | 89 |

The abbreviations as follows: are defined
1.001 = compound No. 1.001
TCZ = Tebuconazole
PYS = Pyraclostrobin

TABLE B42

| Solution of 1.001 ppm | Solution of TCZ + TFS 2:1 ppm | ppm | observed % activity | expected action (colby) |
|---|---|---|---|---|
| B42.1: *Alternaria solani* | | | | |
| 0.0004 | | | 10 | |
| 0.0008 | | | 30 | |
| 0.0016 | | | 54 | |
| | 0.0010 | 0.0005 | 10 | |
| | 0.0021 | 0.0010 | 17 | |
| | 0.0042 | 0.0021 | 9 | |
| 0.0004 | 0.0010 | 0.0005 | 30 | 19 |
| 0.0008 | 0.0021 | 0.0010 | 44 | 42 |
| 0.0016 | 0.0042 | 0.0021 | 74 | 58 |

TABLE B42-continued

| Solution of 1.001 ppm | Solution of TCZ + TFS 2:1 ppm | ppm | observed % activity | expected action (colby) |
|---|---|---|---|---|
| B42.2: *Fusarium culmorum* | | | | |
| 0.0125 | | | 16 | |
| 0.0250 | | | 34 | |
| 0.0500 | | | 54 | |
| 0.1000 | | | 58 | |
| 0.2000 | | | 59 | |
| | 0.0042 | 0.0021 | 1 | |
| | 0.0168 | 0.0083 | 1 | |
| | 0.0335 | 0.0165 | 2 | |
| | 0.0670 | 0.0330 | 6 | |
| | 0.1340 | 0.0660 | 6 | |
| | 0.1340 | 0.0660 | 8 | |
| 0.0125 | 0.0168 | 0.0083 | 42 | 17 |
| 0.0125 | 0.0335 | 0.0165 | 58 | 18 |
| 0.0250 | 0.0042 | 0.0021 | 51 | 35 |
| 0.0250 | 0.0168 | 0.0083 | 51 | 35 |
| 0.0250 | 0.0335 | 0.0165 | 66 | 36 |
| 0.0250 | 0.0670 | 0.0330 | 71 | 39 |
| 0.0500 | 0.0168 | 0.0083 | 60 | 54 |
| 0.0500 | 0.0335 | 0.0165 | 69 | 55 |
| 0.0500 | 0.0670 | 0.0330 | 78 | 57 |
| 0.0500 | 0.1340 | 0.0660 | 75 | 57 |
| 0.1000 | 0.0335 | 0.0165 | 72 | 59 |
| 0.1000 | 0.0670 | 0.0330 | 78 | 61 |
| 0.1000 | 0.1340 | 0.0660 | 80 | 61 |
| 0.2000 | 0.0335 | 0.0165 | 75 | 60 |
| 0.2000 | 0.0670 | 0.0330 | 76 | 62 |
| 0.2000 | 0.1340 | 0.0660 | 83 | 63 |
| B42.3: *Rhizoctonia solani* | | | | |
| 0.0250 | | | 0 | |
| 0.0500 | | | 0 | |
| 0.1000 | | | 15 | |
| | 0.0670 | 0.0330 | 35 | |
| | 0.1340 | 0.0660 | 13 | |
| 0.0250 | 0.0670 | 0.0330 | 51 | 35 |
| 0.0500 | 0.1340 | 0.0660 | 68 | 13 |
| 0.1000 | 0.1340 | 0.0660 | 52 | 26 |
| B42.4: *Septoria tritici* | | | | |
| 0.0004 | | | 9 | |
| 0.0008 | | | 24 | |
| 0.0016 | | | 64 | |
| | 0.0010 | 0.0005 | 10 | |
| | 0.0021 | 0.0010 | 34 | |
| 0.0004 | 0.0010 | 0.0005 | 27 | 17 |
| 0.0008 | 0.0010 | 0.0005 | 65 | 32 |
| 0.0008 | 0.0021 | 0.0010 | 80 | 50 |
| 0.0016 | 0.0010 | 0.0005 | 88 | 67 |
| 0.0016 | 0.0021 | 0.0010 | 86 | 76 |
| B42.5: *Botrytis cinerea* | | | | |
| 0.0008 | | | 24 | |
| 0.0016 | | | 45 | |
| 0.0031 | | | 76 | |
| | 0.0021 | 0.0010 | 15 | |
| | 0.0042 | 0.0021 | 32 | |
| 0.0008 | 0.0021 | 0.0010 | 72 | 35 |
| 0.0016 | 0.0021 | 0.0010 | 88 | 53 |
| 0.0016 | 0.0042 | 0.0021 | 98 | 62 |
| 0.0031 | 0.0021 | 0.0010 | 89 | 79 |
| 0.0031 | 0.0042 | 0.0021 | 99 | 83 |

The abbreviations are defined as follows:
1.001 = compound No. 1.001
TCZ = Tebuconazole
TFS = Trifloxystrobin

TABLE B43

| Solution of 1.001 ppm | Solution of TCZ + FDL 1:2 ppm | ppm | observed % activity | expected action (colby) |
|---|---|---|---|---|
| B43.1: *Alternaria solani* | | | | |
| 0.0016 | | | 45 | |
| | 0.0001 | 0.0003 | 0 | |
| | 0.0021 | 0.0042 | 0 | |
| 0.0016 | 0.0001 | 0.0003 | 54 | 45 |
| 0.0016 | 0.0021 | 0.0042 | 78 | 45 |
| B43.2: *Fusarium culmorum* | | | | |
| 0.0250 | | | 34 | |
| 0.0500 | | | 55 | |
| 0.1000 | | | 55 | |
| 0.2000 | | | 61 | |
| | 0.0330 | 0.0670 | 1 | |
| | 0.0660 | 0.1340 | 1 | |
| | 0.0660 | 0.1340 | 25 | |
| 0.0250 | 0.0330 | 0.0670 | 56 | 34 |
| 0.0500 | 0.0330 | 0.0670 | 89 | 56 |
| 0.0500 | 0.0660 | 0.1340 | 100 | 67 |
| 0.1000 | 0.0330 | 0.0670 | 81 | 56 |
| 0.1000 | 0.0660 | 0.1340 | 97 | 66 |
| 0.2000 | 0.0330 | 0.0670 | 76 | 61 |
| 0.2000 | 0.0660 | 0.1340 | 98 | 71 |
| B43.3: *Monographella nivalis* | | | | |
| 0.0063 | | | 1 | |
| 0.0125 | | | 4 | |
| 0.0250 | | | 14 | |
| 0.0500 | | | 11 | |
| | 0.0041 | 0.0084 | 24 | |
| | 0.0083 | 0.0168 | 70 | |
| 0.0063 | 0.0083 | 0.0168 | 95 | 70 |
| 0.0125 | 0.0083 | 0.0168 | 98 | 71 |
| 0.0250 | 0.0041 | 0.0084 | 55 | 35 |
| 0.0250 | 0.0083 | 0.0168 | 100 | 74 |
| 0.0500 | 0.0041 | 0.0084 | 59 | 33 |
| B43.4: *Botrytis cinerea* | | | | |
| 0.0008 | | | 36 | |
| 0.0016 | | | 51 | |
| 0.0031 | | | 80 | |
| | 0.0005 | 0.0010 | 0 | |
| | 0.0010 | 0.0021 | 12 | |
| | 0.0021 | 0.0042 | 37 | |
| | 0.0041 | 0.0084 | 22 | |
| 0.0008 | 0.0005 | 0.0010 | 42 | 36 |
| 0.0016 | 0.0021 | 0.0042 | 91 | 69 |
| 0.0031 | 0.0010 | 0.0021 | 94 | 82 |
| 0.0031 | 0.0041 | 0.0084 | 100 | 84 |

The abbreviations are defined as follows:
1.001 = compound No. 1.001
TCZ = Tebuconazole
FDL = Fludioxonil

TABLE B44

| Solution of 1.001 ppm | Solution of TCZ + CPL 1:2 ppm | ppm | observed % activity | expected action (colby) |
|---|---|---|---|---|
| B44.1: *Alternaria solani* | | | | |
| 0.0016 | | | 35 | |
| | 0.0001 | 0.0003 | 8 | |
| | 0.0003 | 0.0005 | 0 | |
| | 0.0005 | 0.0010 | 0 | |
| | 0.0010 | 0.0021 | 4 | |
| | 0.0021 | 0.0042 | 5 | |
| 0.0016 | 0.0001 | 0.0003 | 57 | 40 |
| 0.0016 | 0.0003 | 0.0005 | 52 | 35 |
| 0.0016 | 0.0005 | 0.0010 | 47 | 35 |

TABLE B44-continued

| Solution of 1.001 ppm | Solution of TCZ + CPL 1:2 ppm | ppm | observed % activity | expected action (colby) |
|---|---|---|---|---|
| 0.0016 | 0.0010 | 0.0021 | 64 | 38 |
| 0.0016 | 0.0021 | 0.0042 | 52 | 39 |
| B44.2: *Monographella nivalis* | | | | |
| 0.0016 | | | 4 | |
| 0.0031 | | | 0 | |
| 0.0063 | | | 3 | |
| | 0.0021 | 0.0042 | 10 | |
| | 0.0041 | 0.0084 | 52 | |
| 0.0016 | 0.0021 | 0.0042 | 35 | 14 |
| 0.0031 | 0.0041 | 0.0084 | 97 | 52 |
| 0.0063 | 0.0041 | 0.0084 | 91 | 53 |

The abbreviations are defined as follows:

1.001 = compound No. 1.001

TCZ = Tebuconazole

CPL = Cyprodinil

TABLE B45

| Solution of 1.001 ppm | Solution of TCZ + FLN 1:3 ppm | ppm | observed % activity | expected action (colby) |
|---|---|---|---|---|
| B45.1: *Alternaria solani* | | | | |
| 0.0008 | | | 10 | |
| 0.0016 | | | 40 | |
| 0.0031 | | | 76 | |
| | 0.0001 | 0.0003 | 0 | |
| | 0.0002 | 0.0006 | 0 | |
| | 0.0004 | 0.0012 | 0 | |
| | 0.0008 | 0.0023 | 5 | |
| | 0.0016 | 0.0047 | 10 | |
| | 0.0031 | 0.0094 | 22 | |
| 0.0008 | 0.0004 | 0.0012 | 27 | 10 |
| 0.0016 | 0.0001 | 0.0003 | 50 | 40 |
| 0.0016 | 0.0008 | 0.0023 | 46 | 43 |
| 0.0016 | 0.0016 | 0.0047 | 66 | 45 |
| 0.0031 | 0.0002 | 0.0006 | 88 | 76 |
| 0.0031 | 0.0016 | 0.0047 | 90 | 78 |
| 0.0031 | 0.0031 | 0.0094 | 92 | 81 |
| B45.2: *Monographella nivalis* | | | | |
| 0.0016 | | | 2 | |
| 0.0031 | | | 0 | |
| 0.0063 | | | 5 | |
| 0.0125 | | | 5 | |
| 0.0250 | | | 6 | |
| 0.0500 | | | 9 | |
| | 0.0016 | 0.0047 | 0 | |
| | 0.0031 | 0.0094 | 45 | |
| 0.0016 | 0.0016 | 0.0047 | 31 | 2 |
| 0.0031 | 0.0031 | 0.0094 | 90 | 45 |
| 0.0063 | 0.0031 | 0.0094 | 73 | 48 |
| 0.0125 | 0.0031 | 0.0094 | 79 | 48 |
| 0.0250 | 0.0016 | 0.0047 | 29 | 6 |
| 0.0500 | 0.0031 | 0.0094 | 84 | 50 |
| B45.3: *Botrytis cinerea* | | | | |
| 0.0008 | | | 36 | |
| 0.0016 | | | 68 | |
| 0.0031 | | | 86 | |
| | 0.0004 | 0.0012 | 3 | |
| | 0.0008 | 0.0023 | 8 | |
| | 0.0016 | 0.0047 | 6 | |
| | 0.0031 | 0.0094 | 10 | |
| 0.0008 | 0.0004 | 0.0012 | 59 | 38 |
| 0.0008 | 0.0008 | 0.0023 | 85 | 41 |

TABLE B45-continued

| Solution of 1.001 ppm | Solution of TCZ + FLN 1:3 ppm | ppm | observed % activity | expected action (colby) |
|---|---|---|---|---|
| 0.0016 | 0.0008 | 0.0023 | 94 | 71 |
| 0.0016 | 0.0016 | 0.0047 | 99 | 70 |
| 0.0031 | 0.0016 | 0.0047 | 99 | 87 |
| 0.0031 | 0.0031 | 0.0094 | 100 | 88 |

The abbreviations are defined as follows:

1.001 = compound No. 1.001

TCZ = Tebuconazole

FLN = Fluazinam

TABLE B46

| Solution of 1.001 ppm | Solution of PYS + TFS 1:1 ppm | ppm | observed % activity | expected action (colby) |
|---|---|---|---|---|
| B46.1: *Alternaria solani* | | | | |
| 0.0016 | | | 53 | |
| 0.0031 | | | 73 | |
| | 0.0002 | 0.0002 | 0 | |
| | 0.0008 | 0.0008 | 0 | |
| | 0.0031 | 0.0031 | 13 | |
| | 0.0063 | 0.0063 | 20 | |
| 0.0016 | 0.0002 | 0.0002 | 65 | 53 |
| 0.0016 | 0.0031 | 0.0031 | 67 | 59 |
| 0.0031 | 0.0008 | 0.0008 | 80 | 73 |
| 0.0031 | 0.0031 | 0.0031 | 86 | 76 |
| 0.0031 | 0.0063 | 0.0063 | 89 | 78 |
| B46.2: *Monographella nivalis* | | | | |
| 0.0016 | | | 1 | |
| 0.0031 | | | 2 | |
| 0.0063 | | | 0 | |
| 0.0250 | | | 7 | |
| | 0.0031 | 0.0031 | 25 | |
| | 0.0063 | 0.0063 | 66 | |
| 0.0016 | 0.0031 | 0.0031 | 37 | 26 |
| 0.0031 | 0.0063 | 0.0063 | 98 | 67 |
| 0.0063 | 0.0031 | 0.0031 | 55 | 25 |
| 0.0063 | 0.0063 | 0.0063 | 76 | 66 |
| 0.0250 | 0.0063 | 0.0063 | 100 | 69 |
| B46.3: *Septoria tritici* | | | | |
| 0.0016 | | | 53 | |
| | 0.0004 | 0.0004 | 0 | |
| | 0.0016 | 0.0016 | 1 | |
| | 0.0031 | 0.0031 | 1 | |
| 0.0016 | 0.0004 | 0.0004 | 61 | 53 |
| 0.0016 | 0.0016 | 0.0016 | 60 | 54 |
| 0.0016 | 0.0031 | 0.0031 | 66 | 54 |
| B46.4: *Botrytis cinerea* | | | | |
| 0.0016 | | | 43 | |
| | 0.0002 | 0.0002 | 3 | |
| | 0.0008 | 0.0008 | 0 | |
| 0.0016 | 0.0002 | 0.0002 | 52 | 45 |
| 0.0016 | 0.0008 | 0.0008 | 51 | 43 |

The abbreviations are defined as follows:

1.001 = compound No. 1.001

PYS = Pyraclostrobin

TFS = Trifloxystrobin

TABLE B47

| Solution of 1.001 ppm | Solution of PYS + FDL 1:4 ppm | | observed % activity | expected action (colby) |
|---|---|---|---|---|
| | B47.1: *Alternia solani* | | | |
| 0.0016 | | | 53 | |
| | 0.0013 | 0.0050 | 2 | |
| 0.0016 | 0.0013 | 0.0050 | 71 | 54 |
| | B47.2: *Septoria tritici* | | | |
| 0.0008 | | | 15 | |
| 0.0016 | | | 53 | |
| | 0.0006 | 0.0025 | 14 | |
| | 0.0013 | 0.0050 | 39 | |
| 0.0008 | 0.0006 | 0.0025 | 48 | 26 |
| 0.0016 | 0.0013 | 0.0050 | 90 | 71 |
| | B47.3: *Botrytis cinerea* | | | |
| 0.0016 | | | 42 | |
| 0.0031 | | | 68 | |
| | 0.0013 | 0.0050 | 16 | |
| | 0.0025 | 0.0100 | 38 | |
| 0.0016 | 0.0013 | 0.0050 | 88 | 51 |
| 0.0031 | 0.0013 | 0.0050 | 93 | 73 |
| 0.0031 | 0.0025 | 0.0100 | 99 | 80 |

The abbreviations are defined as follows:
1.001 = compound No. 1.001
PYS = Pyraclostrobin
FDL = Fludioxonil

TABLE B48

| Solution of 1.001 ppm | Solution of PYS + CPL 1:4 ppm | | observed % activity | expected action (colby) |
|---|---|---|---|---|
| | B48.1: *Alternaria solani* | | | |
| 0.0008 | | | 24 | |
| 0.0016 | | | 46 | |
| | 0.0001 | 0.0003 | 8 | |
| | 0.0003 | 0.0013 | 1 | |
| | 0.0006 | 0.0025 | 2 | |
| | 0.0013 | 0.0050 | 2 | |
| 0.0008 | 0.0006 | 0.0025 | 34 | 26 |
| 0.0016 | 0.0001 | 0.0003 | 59 | 50 |
| 0.0016 | 0.0003 | 0.0013 | 55 | 47 |
| 0.0016 | 0.0006 | 0.0025 | 59 | 48 |
| 0.0016 | 0.0013 | 0.0050 | 70 | 48 |
| | B48.2: *Fusarium culmorum* | | | |
| 0.0125 | | | 10 | |
| 0.0250 | | | 32 | |
| 0.0500 | | | 59 | |
| 0.1000 | | | 56 | |
| 0.2000 | | | 60 | |
| | 0.0100 | 0.0400 | 12 | |
| | 0.0200 | 0.0800 | 8 | |
| | 0.0400 | 0.1600 | 8 | |
| | 0.0400 | 0.1600 | 35 | |
| 0.0125 | 0.0100 | 0.0400 | 36 | 20 |
| 0.0250 | 0.0100 | 0.0400 | 46 | 40 |
| 0.0250 | 0.0200 | 0.0800 | 56 | 37 |
| 0.0500 | 0.0400 | 0.1600 | 100 | 73 |
| 0.1000 | 0.0200 | 0.0800 | 73 | 60 |
| 0.1000 | 0.0400 | 0.1600 | 98 | 71 |
| 0.2000 | 0.0400 | 0.1600 | 98 | 74 |
| | B48.3: *Monographella nivalis* | | | |
| 0.0250 | | | 15 | |
| 0.0500 | | | 21 | |
| | 0.0050 | 0.0200 | 0 | |
| | 0.0200 | 0.0800 | 0 | |
| | 0.0400 | 0.1600 | 46 | |
| 0.0250 | 0.0200 | 0.0800 | 48 | 15 |
| 0.0500 | 0.0050 | 0.0200 | 58 | 21 |
| 0.0500 | 0.0400 | 0.1600 | 85 | 57 |
| | B48.4: *Rhizoctonia solani* | | | |
| 0.0500 | | | 0 | |
| 0.2000 | | | 0 | |
| | 0.0400 | 0.1600 | 16 | |
| | 0.0400 | 0.1600 | 61 | |
| 0.0500 | 0.0400 | 0.1600 | 76 | 61 |
| 0.2000 | 0.0400 | 0.1600 | 72 | 61 |
| | B48.5: *Septoria tritici* | | | |
| 0.0016 | | | 58 | |
| | 0.0013 | 0.0050 | 0 | |
| 0.0016 | 0.0013 | 0.0050 | 67 | 58 |
| | B48.6: *Botrytis cinerea* | | | |
| 0.0008 | | | 30 | |
| 0.0016 | | | 59 | |
| 0.0031 | | | 76 | |
| | 0.0002 | 0.0006 | 3 | |
| | 0.0006 | 0.0025 | 7 | |
| | 0.0013 | 0.0050 | 0 | |
| | 0.0025 | 0.0100 | 21 | |
| 0.0008 | 0.0002 | 0.0006 | 44 | 32 |
| 0.0008 | 0.0006 | 0.0025 | 41 | 35 |
| 0.0016 | 0.0013 | 0.0050 | 91 | 59 |
| 0.0031 | 0.0006 | 0.0025 | 91 | 78 |
| 0.0031 | 0.0013 | 0.0050 | 85 | 76 |
| 0.0031 | 0.0025 | 0.0100 | 99 | 81 |

The abbreviations are defined as follows:
1.001 = compound No. 1.001
PYS = Pyraclostrobin
CPL = Cyprodinil

TABLE B49

| Solution of 1.001 ppm | Solution of PYS + FLN 1:6 ppm | | observed % activity | expected action (colby) |
|---|---|---|---|---|
| | B49.1: *Monographella nivalis* | | | |
| 0.0031 | | | 6 | |
| | 0.0018 | 0.0107 | 13 | |
| 0.0031 | 0.0018 | 0.0107 | 86 | 18 |
| | B49.2: *Botrytis cinerea* | | | |
| 0.0016 | | | 48 | |
| | 0.0002 | 0.0013 | 0 | |
| | 0.0009 | 0.0054 | 0 | |
| 0.0016 | 0.0002 | 0.0013 | 53 | 48 |
| 0.0016 | 0.0009 | 0.0054 | 56 | 48 |

The abbreviations are defined as follows:
1.001 = compound No. 1.001
PYS = Pyraclostrobin
FLN = Fluazinam

TABLE B50

| Solution of 1.001 ppm | Solution of TFS + FDL 1:4 ppm | ppm | observed % activity | expected action (colby) |
|---|---|---|---|---|
| B50.1: *Fusarium culmorum* | | | | |
| 0.0125 | | | 11 | |
| 0.0250 | | | 33 | |
| 0.0500 | | | 56 | |
| 0.1000 | | | 59 | |
| 0.2000 | | | 65 | |
| | 0.0050 | 0.0200 | 2 | |
| | 0.0100 | 0.0400 | 20 | |
| | 0.0200 | 0.0800 | 29 | |
| 0.0125 | 0.0050 | 0.0200 | 51 | 12 |
| 0.0125 | 0.0100 | 0.0400 | 50 | 28 |
| 0.0250 | 0.0050 | 0.0200 | 50 | 34 |
| 0.0250 | 0.0100 | 0.0400 | 62 | 46 |
| 0.0250 | 0.0200 | 0.0800 | 100 | 53 |
| 0.0500 | 0.0200 | 0.0800 | 93 | 69 |
| 0.1000 | 0.0200 | 0.0800 | 88 | 71 |
| 0.2000 | 0.0200 | 0.0800 | 93 | 76 |
| B50.2: *Monographella nivalis* | | | | |
| 0.0004 | | | 0 | |
| 0.0008 | | | 3 | |
| | 0.0003 | 0.0013 | 44 | |
| 0.0004 | 0.0003 | 0.0013 | 67 | 44 |
| 0.0008 | 0.0003 | 0.0013 | 73 | 46 |
| B50.3: *Rhizoctonia solani* | | | | |
| 0.1000 | | | 0 | |
| 0.2000 | | | 0 | |
| | 0.0400 | 0.1600 | 30 | |
| | 0.0400 | 0.1600 | 65 | |
| 0.1000 | 0.0400 | 0.1600 | 99 | 65 |
| 0.2000 | 0.0400 | 0.1600 | 96 | 65 |
| B50.4: *Septoria tritici* | | | | |
| 0.0008 | | | 27 | |
| 0.0016 | | | 56 | |
| | 0.0006 | 0.0025 | 10 | |
| | 0.0013 | 0.0050 | 21 | |
| 0.0008 | 0.0006 | 0.0025 | 47 | 34 |
| 0.0016 | 0.0006 | 0.0025 | 78 | 60 |
| 0.0016 | 0.0013 | 0.0050 | 73 | 65 |
| B50.5: *Botrytis cinerea* | | | | |
| 0.0008 | | | 9 | |
| 0.0016 | | | 26 | |
| 0.0031 | | | 49 | |
| | 0.0006 | 0.0025 | 6 | |
| | 0.0013 | 0.0050 | 33 | |
| | 0.0025 | 0.0100 | 37 | |
| 0.0008 | 0.0006 | 0.0025 | 22 | 14 |
| 0.0016 | 0.0013 | 0.0050 | 78 | 50 |
| 0.0031 | 0.0025 | 0.0100 | 89 | 68 |

The abbreviations are defined as follows:
1.001 = compound No. 1.001
TFS = Trifloxystrobin
FDL = Fludioxonil

TABLE B51

| Solution of 1.001 ppm | Solution of TFS + CPL 1:4 ppm | ppm | observed % activity | expected action (colby) |
|---|---|---|---|---|
| B51.1: *Fusarium culmorum* | | | | |
| 0.0250 | | | 29 | |
| 0.0500 | | | 54 | |
| 0.1000 | | | 57 | |
| 0.2000 | | | 58 | |
| | 0.0100 | 0.0400 | 7 | |
| | 0.0200 | 0.0800 | 6 | |
| | 0.0400 | 0.1600 | 6 | |
| | 0.0400 | 0.1600 | 8 | |
| 0.0250 | 0.0100 | 0.0400 | 56 | 34 |
| 0.0250 | 0.0200 | 0.0800 | 70 | 33 |
| 0.0500 | 0.0100 | 0.0400 | 64 | 57 |
| 0.0500 | 0.0200 | 0.0800 | 77 | 56 |
| 0.0500 | 0.0400 | 0.1600 | 80 | 58 |
| 0.1000 | 0.0100 | 0.0400 | 67 | 60 |
| 0.1000 | 0.0200 | 0.0800 | 77 | 60 |
| 0.1000 | 0.0400 | 0.1600 | 84 | 61 |
| 0.2000 | 0.0200 | 0.0800 | 73 | 60 |
| 0.2000 | 0.0400 | 0.1600 | 83 | 62 |
| B51.2: *Monographella nivalis* | | | | |
| 0.0004 | | | 2 | |
| 0.0008 | | | 0 | |
| 0.0016 | | | 0 | |
| 0.0031 | | | 2 | |
| 0.0125 | | | 0 | |
| | 0.0003 | 0.0013 | 46 | |
| | 0.0006 | 0.0025 | 88 | |
| 0.0004 | 0.0003 | 0.0013 | 98 | 48 |
| 0.0008 | 0.0003 | 0.0013 | 93 | 46 |
| 0.0008 | 0.0006 | 0.0025 | 98 | 88 |
| 0.0016 | 0.0006 | 0.0025 | 98 | 88 |
| 0.0031 | 0.0006 | 0.0025 | 97 | 88 |
| 0.0125 | 0.0006 | 0.0025 | 97 | 88 |
| B51.3: *Septoria tritici* | | | | |
| 0.0008 | | | 18 | |
| 0.0016 | | | 47 | |
| | 0.0006 | 0.0025 | 10 | |
| | 0.0013 | 0.0050 | 25 | |
| 0.0008 | 0.0006 | 0.0025 | 34 | 26 |
| 0.0016 | 0.0013 | 0.0050 | 78 | 60 |

The abbreviations are defined as follows:
1.001 = compound No. 1.001
TFS = Trifloxystrobin
CPL = Cyprodinil

TABLE B52

| Solution of 1.001 ppm | Solution of TFS + FLN 1:6 ppm | ppm | observed % activity | expected action (colby) |
|---|---|---|---|---|
| B52.1: *Alternaria solani* | | | | |
| 0.0016 | | | 21 | |
| 0.0031 | | | 57 | |
| | 0.0009 | 0.0054 | 5 | |
| 0.0016 | 0.0009 | 0.0054 | 48 | 25 |
| 0.0031 | 0.0009 | 0.0054 | 82 | 59 |
| B52.2: *Fusarium culmorum* | | | | |
| 0.0125 | | | 6 | |
| 0.0250 | | | 26 | |
| | 0.0072 | 0.0428 | 23 | |
| | 0.0143 | 0.0857 | 30 | |
| 0.0125 | 0.0072 | 0.0428 | 40 | 28 |
| 0.0250 | 0.0143 | 0.0857 | 58 | 48 |
| B52.3: *Monographella nivalis* | | | | |
| 0.0004 | | | 3 | |
| 0.0063 | | | 2 | |
| | 0.0002 | 0.0013 | 38 | |
| 0.0004 | 0.0002 | 0.0013 | 97 | 40 |
| 0.0063 | 0.0002 | 0.0013 | 85 | 39 |

TABLE B52-continued

| Solution of 1.001 ppm | Solution of TFS + FLN 1:6 ppm | ppm | observed % activity | expected action (colby) |
|---|---|---|---|---|
| B52.4: *Botrytis cinerea* | | | | |
| 0.0016 | | | 29 | |
| 0.0031 | | | 58 | |
| 0.0063 | | | 74 | |
| | 0.0009 | 0.0054 | 18 | |
| | 0.0018 | 0.0107 | 76 | |
| 0.0016 | 0.0009 | 0.0054 | 84 | 42 |
| 0.0031 | 0.0009 | 0.0054 | 91 | 65 |
| 0.0031 | 0.0018 | 0.0107 | 100 | 90 |
| 0.0063 | 0.0009 | 0.0054 | 88 | 79 |

The abbreviations are defined as follows:
1.001 = compound No. 1.001
TFS = Trifloxystrobin
FLN = Fluazinam

TABLE B53

| Solution of 1.001 ppm | Solution of FDL + CPL (1:1) ppm | ppm | observed % activity | expected action (colby) |
|---|---|---|---|---|
| B53.1: *Fusarium culmorum* | | | | |
| 0.0500 | | | 49 | |
| 0.1000 | | | 59 | |
| 0.2000 | | | 55 | |
| | 0.1000 | 0.1000 | 8 | |
| | 0.1000 | 0.1000 | 6 | |
| 0.0500 | 0.1000 | 0.1000 | 81 | 51 |
| 0.1000 | 0.1000 | 0.1000 | 85 | 62 |
| 0.2000 | 0.1000 | 0.1000 | 84 | 58 |
| B53.2: *Monographella nivalis* | | | | |
| 0.0063 | | | 0 | |
| 0.0125 | | | 0 | |
| | 0.0125 | 0.0125 | 26 | |
| 0.0063 | 0.0125 | 0.0125 | 67 | 26 |
| 0.0125 | 0.0125 | 0.0125 | 46 | 26 |
| B53.3: *Botrytis cinerea* | | | | |
| 0.0016 | | | 49 | |
| 0.0031 | | | 71 | |
| 0.0063 | | | 87 | |
| | 0.0031 | 0.0031 | 3 | |
| | 0.0063 | 0.0063 | 4 | |
| | 0.0125 | 0.0125 | 16 | |
| 0.0016 | 0.0031 | 0.0031 | 61 | 50 |
| 0.0031 | 0.0063 | 0.0063 | 91 | 72 |
| 0.0063 | 0.0063 | 0.0063 | 97 | 87 |
| 0.0063 | 0.0125 | 0.0125 | 100 | 89 |

The abbreviations are defined as follows:
1.001 = compound No. 1.001
FDL = Fludioxonil
CPL = Cyprodinil

TABLE B54

| Solution of 1.001 ppm | Solution of FDL + FLN (2:3) ppm | ppm | observed % activity | expected action (colby) |
|---|---|---|---|---|
| B54.1: *Alternaria solani* | | | | |
| 0.0008 | | | 42 | |
| | 0.0002 | 0.0002 | 3 | |
| 0.0008 | 0.0002 | 0.0002 | 65 | 44 |

TABLE B54-continued

| Solution of 1.001 ppm | Solution of FDL + FLN (2:3) ppm | ppm | observed % activity | expected action (colby) |
|---|---|---|---|---|
| B54.2: *Fusarium culmorum* | | | | |
| 0.0500 | | | 51 | |
| 0.1000 | | | 55 | |
| 0.2000 | | | 60 | |
| | 0.0400 | 0.0600 | 0 | |
| | 0.0800 | 0.1200 | 0 | |
| | 0.0800 | 0.1200 | 15 | |
| 0.0500 | 0.0400 | 0.0600 | 64 | 51 |
| 0.0500 | 0.0800 | 0.1200 | 87 | 59 |
| 0.1000 | 0.0400 | 0.0600 | 61 | 55 |
| 0.1000 | 0.0800 | 0.1200 | 87 | 62 |
| 0.2000 | 0.0400 | 0.0600 | 75 | 60 |
| 0.2000 | 0.0800 | 0.1200 | 88 | 66 |
| B54.3: *Monographella nivalis* | | | | |
| 0.0500 | | | 3 | |
| 0.1000 | | | 22 | |
| | 0.0100 | 0.0150 | 5 | |
| | 0.0200 | 0.0300 | 0 | |
| | 0.0400 | 0.0600 | 1 | |
| | 0.0800 | 0.1200 | 67 | |
| 0.0500 | 0.0400 | 0.0600 | 38 | 4 |
| 0.0500 | 0.0800 | 0.1200 | 100 | 68 |
| 0.1000 | 0.0100 | 0.0150 | 39 | 26 |
| 0.1000 | 0.0200 | 0.0300 | 46 | 22 |
| 0.1000 | 0.0400 | 0.0600 | 68 | 23 |
| 0.1000 | 0.0800 | 0.1200 | 94 | 74 |
| B54.4: *Botrytis cinerea* | | | | |
| 0.0008 | | | 34 | |
| 0.0031 | | | 75 | |
| 0.0063 | | | 89 | |
| | 0.0002 | 0.0002 | 9 | |
| | 0.0050 | 0.0075 | 4 | |
| | 0.0100 | 0.0150 | 8 | |
| 0.0008 | 0.0002 | 0.0002 | 61 | 40 |
| 0.0031 | 0.0050 | 0.0075 | 89 | 76 |
| 0.0063 | 0.0050 | 0.0075 | 98 | 90 |
| 0.0063 | 0.0100 | 0.0150 | 100 | 90 |

The abbreviations are defined as follows:
1.001 = compound No. 1.001
FDL = Fludioxonil
FLN = Fluazinam

TABLE B55

| Solution of 1.001 ppm | Solution of CPL + FLN (2:3) ppm | ppm | observed % activity | expected action (colby) |
|---|---|---|---|---|
| B55.1: *Alternaria solani* | | | | |
| 0.0016 | | | 55 | |
| | 0.0002 | 0.0002 | 0 | |
| | 0.0003 | 0.0005 | 9 | |
| 0.0016 | 0.0002 | 0.0002 | 69 | 55 |
| 0.0016 | 0.0003 | 0.0005 | 69 | 59 |
| B55.2: *Fusarium culmorum* | | | | |
| 0.0250 | | | 16 | |
| 0.2000 | | | 51 | |
| | 0.0025 | 0.0038 | 0 | |
| | 0.0200 | 0.0300 | 0 | |
| 0.0250 | 0.0025 | 0.0038 | 44 | 16 |
| 0.2000 | 0.0200 | 0.0300 | 60 | 51 |
| B55.3: *Monographella nivalis* | | | | |
| 0.1000 | | | 19 | |
| 0.2000 | | | 79 | |
| | 0.0100 | 0.0150 | 2 | |

TABLE B55-continued

| Solution of 1.001 ppm | Solution of CPL + FLN (2:3) ppm | ppm | observed % activity | expected action (colby) |
|---|---|---|---|---|
|  | 0.0200 | 0.0300 | 28 |  |
| 0.1000 | 0.0100 | 0.0150 | 41 | 21 |
| 0.2000 | 0.0200 | 0.0300 | 90 | 85 |
| B55.4: *Septoria tritici* | | | | |
| 0.0016 |  |  | 63 |  |
|  | 0.0002 | 0.0002 | 5 |  |
| 0.0016 | 0.0002 | 0.0002 | 82 | 65 |
| B55.5: *Botrytis cinerea* | | | | |
| 0.0016 |  |  | 38 |  |
| 0.0031 |  |  | 53 |  |
| 0.0063 |  |  | 66 |  |
| 0.0125 |  |  | 83 |  |
|  | 0.0013 | 0.0019 | 1 |  |
|  | 0.0050 | 0.0075 | 4 |  |
|  | 0.0100 | 0.0150 | 4 |  |
| 0.0016 | 0.0013 | 0.0019 | 58 | 38 |
| 0.0031 | 0.0050 | 0.0075 | 76 | 55 |
| 0.0063 | 0.0050 | 0.0075 | 94 | 67 |
| 0.0063 | 0.0100 | 0.0150 | 100 | 67 |
| 0.0125 | 0.0013 | 0.0019 | 94 | 84 |
| 0.0125 | 0.0050 | 0.0075 | 97 | 84 |
| 0.0125 | 0.0100 | 0.0150 | 100 | 84 |

The abbreviations are defined as follows:
1.001 = compound No. 1.001
CPL = Cyprodinil
FLN = Fluazinam

What is claimed:

1. A composition suitable for control of diseases caused by phytopathogens comprising
   as component (A) 3-(difluoromethyl)-N-methoxy-1-methyl-N-[1-methyl-2-(2,4,6-trichlorophenyl)ethyl]pyrazole-4-carboxamide;
   and
   as component (B) the compound of formula VII

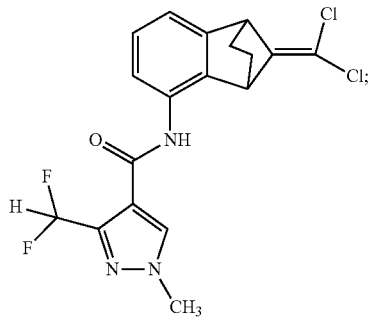

and as component (C)
   azoxystrobin; and
   wherein the weight ratio of (A) to (B+C) is from 4:1 to 1:4.

2. A method of controlling diseases on useful plants or on propagation material thereof caused by phytopathogens, which comprises applying to the useful plants, the locus thereof or propagation material thereof a composition according to claim 1.

3. A method of protecting natural substances of plant and/or animal origin, which have been taken from the natural life cycle, and/or their processed forms, which comprises applying to said natural substances of plant and/or animal origin or their processed forms a combination of components (A), (B) and (C) according to claim 1.

* * * * *